(12) United States Patent
Faruqi et al.

(10) Patent No.: US 12,370,369 B2
(45) Date of Patent: Jul. 29, 2025

(54) ESOPHAGEAL INTUBATION ASSEMBLIES FOR CARDIAC STIMULATION AND ACCESS TO GASTRIC CONTENTS

(71) Applicant: ENDEAVOR MED INC., Spring, TX (US)

(72) Inventors: Imran Ahmed Faruqi, Spring, TX (US); Bandula Wijay, Friendswood, TX (US)

(73) Assignee: ENDEAVOR MED INC., Spring, TX (US)

( * ) Notice: Subject to any disclaimer, the term of this patent is extended or adjusted under 35 U.S.C. 154(b) by 8 days.

(21) Appl. No.: 18/422,107

(22) Filed: Jan. 25, 2024

(65) Prior Publication Data

US 2024/0245919 A1   Jul. 25, 2024

Related U.S. Application Data

(60) Provisional application No. 63/440,940, filed on Jan. 25, 2023.

(51) Int. Cl.
| | | |
|---|---|---|
| *A61N 1/05* | (2006.01) | |
| *A61N 1/36* | (2006.01) | |
| *A61N 1/362* | (2006.01) | |
| *A61B 18/14* | (2006.01) | |

(52) U.S. Cl.
CPC ......... *A61N 1/3629* (2017.08); *A61N 1/0507* (2013.01); *A61N 1/0517* (2013.01); *A61B 18/1492* (2013.01); *A61M 2205/054* (2013.01); *A61M 2210/105* (2013.01)

(58) Field of Classification Search
CPC .. A61N 1/0517; A61N 1/0519; A61N 1/0507; A61B 18/1492; A61B 5/285; A61M 25/007
See application file for complete search history.

(56) References Cited

U.S. PATENT DOCUMENTS

| | | | |
|---|---|---|---|
| 4,574,807 | A | 3/1986 | Hewson et al. |
| 5,056,532 | A | 10/1991 | Hull et al. |
| 5,179,952 | A | 1/1993 | Buinevicius et al. |
| 5,199,433 | A | 4/1993 | Metzger et al. |
| 5,387,232 | A | 2/1995 | Trailer |
| 5,417,713 | A | 5/1995 | Cohen |
| 6,855,116 | B2 | 2/2005 | Atlee, III |
| 8,257,350 | B2 | 9/2012 | Marion |
| 8,401,650 | B2 | 3/2013 | Simon et al. |
| 2002/0032468 | A1 | 3/2002 | Hill et al. |

(Continued)

FOREIGN PATENT DOCUMENTS

| | | | |
|---|---|---|---|
| JP | 2022025437 A | 2/2022 | |
| RU | 2499616 C1 | 7/2012 | |
| WO | WO-2006060458 A1 * | 6/2006 | ......... A61B 1/00105 |

OTHER PUBLICATIONS

Website: https://www.cardiocommand.com/taptechnology.html, as captured on Jan. 24, 2024 (1 page).

(Continued)

*Primary Examiner* — Courtney B Fredrickson
(74) *Attorney, Agent, or Firm* — Van Court & Aldridge LLP

(57) ABSTRACT

Esophageal intubation assemblies, esophageal cardiac stimulation and gastric decompression assemblies, and methods for using and making the same are provided.

17 Claims, 29 Drawing Sheets

(56) References Cited

U.S. PATENT DOCUMENTS

| | | | |
|---|---|---|---|
| 2009/0054952 A1* | 2/2009 | Glukhovsky | A61N 1/36021 607/2 |
| 2009/0143651 A1 | 6/2009 | Kallback et al. | |
| 2010/0228202 A1* | 9/2010 | O'Dea | A61M 25/1027 156/60 |
| 2016/0184588 A1 | 6/2016 | Locke et al. | |
| 2020/0261024 A1 | 8/2020 | Heinke et al. | |

OTHER PUBLICATIONS

"An Esophageal and Gastric Approach to Ventricular Pacing", David J. Cochrane et al., Jan. 1995 (6 pages).

"Esophageal Electrical Cardioversion of Atrial Fibrillation: When Esophagus Gives a Help to Cardiologists", Luca Santini et al., Jul. 19, 2011 (3 pages).

"Cardioversion and Defibrillation: The Esophageal Approach", A. A.J. Adgey et al., 1991 (2 pages).

"ESOFLEX S Data Sheet: Esophageal Lead With Olive-Shaped Electrodes With Touch Proof Connection", 2023 (1 page).

"Transthoracic Versus Transesophageal Cardioversion of Atrial Fibrillation under Light Sedation: A Prospective Randomized Trial", Luca Santini et al., Dec. 2007 (7 pages).

"Transesophageal Defibrillation: Animal Studies and Preliminary Clinical Observations", Todd J. Cohen at al., Jun. 1993 (8 pages).

"Ventricular Pacing With a Novel Gastroesophageal Electrode: A Comparison With External Pacing", David J. McEneaney et al., Jun. 1997 (7 pages).

"Use of the Gastro-Oesophageal Route for the Rapid Establishment of Ventricular Pacing", D.J. McEneaney et al., May 25, 1994 (4 pages).

* cited by examiner

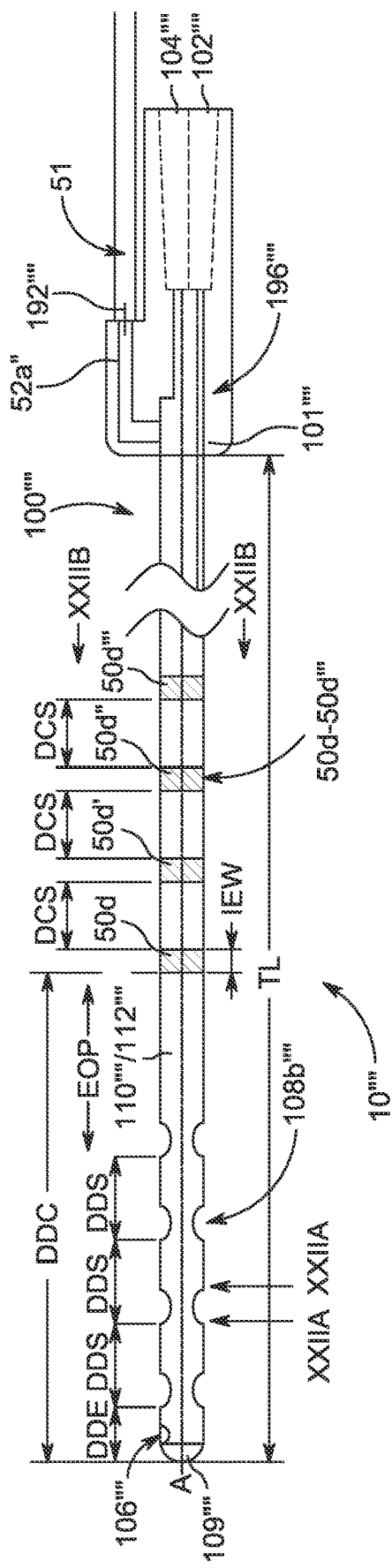
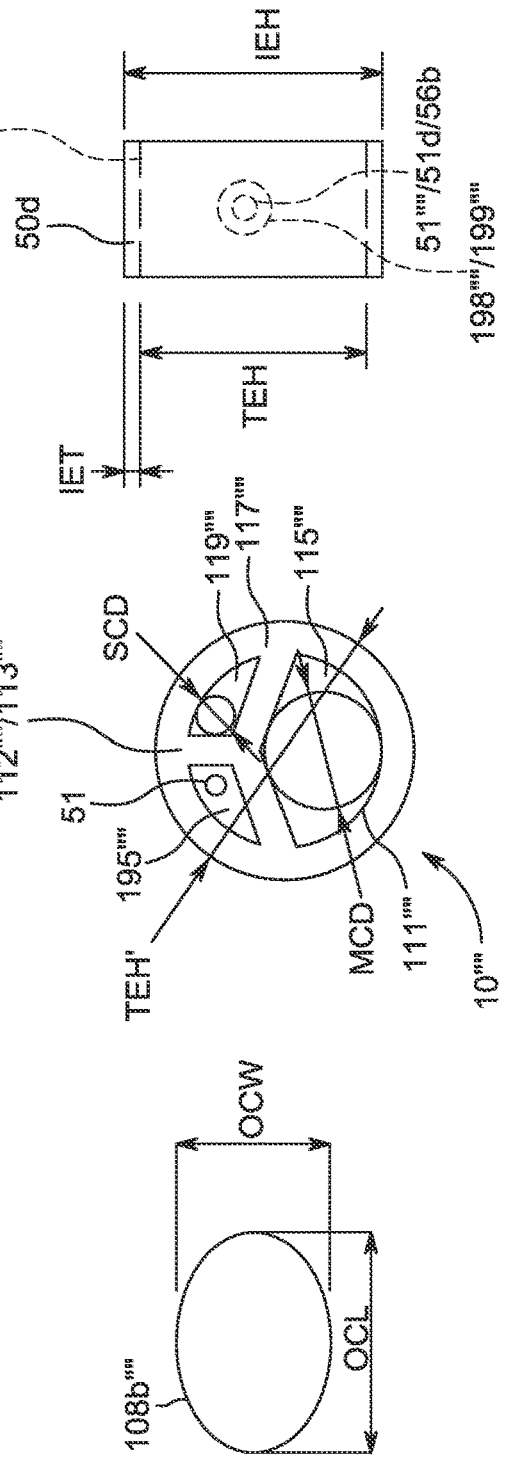
FIG. 22
FIG. 22A
FIG. 22B
FIG. 22C

ESOPHAGEAL INTUBATION ASSEMBLIES FOR CARDIAC STIMULATION AND ACCESS TO GASTRIC CONTENTS

CROSS-REFERENCE TO RELATED APPLICATION(S)

This application claims the benefit of prior filed U.S. Provisional Patent Application No. 63/440,940, filed Jan. 25, 2023, which is hereby incorporated by reference herein in its entirety.

COPYRIGHT NOTICE

At least a portion of the disclosure of this patent document contains material that is subject to copyright protection. The copyright owner has no objection to the facsimile reproduction by anyone of the patent document or patent disclosure as it appears in the Patent and Trademark Office patent file or records, but otherwise reserves all copyright rights whatsoever.

TECHNICAL FIELD

This disclosure relates to esophageal intubation assemblies and, more particularly, to esophageal cardiac stimulation and gastric decompression assemblies, and methods for using and making the same.

BACKGROUND OF THE DISCLOSURE

In patients presenting with critical bradycardia (e.g., low heart rate) or with unstable rhythms, it may be useful or necessary to provide parenteral electrical impulses to the heart to ensure the patient's heart beats at a safe rate and rhythm. Such critically ill patients simultaneously would benefit from gastric decompression to reduce aspiration risk.

SUMMARY OF THE DISCLOSURE

This document describes pacing intubation assemblies and methods for using and making the same.

For example, a pacing intubation assembly is provided.

As another example, a method for using a pacing intubation assembly is provided.

As yet another example, an esophageal intubation assembly is provided that may include a catheter including a body structure extending along a body structure length from a proximal body end to a distal body end, a passageway extending within the body structure and along at least a portion of the body structure length from a proximal passageway end to a distal passageway end, a proximal passageway opening passing through the body structure at a proximal passageway opening location for fluidly coupling the passageway with an ambient environment of the body structure at the proximal passageway opening location, and a distal passageway opening passing through the body structure at a distal passageway opening location for fluidly coupling the passageway with an ambient environment of the body structure at the distal passageway opening location, wherein the distal passageway opening location is distal of the proximal passageway opening location along the body structure length, and cardiac stimulation circuitry including a first electrode coupled to the body structure at a first electrode location, a second internal electrode coupled to the body structure at a second electrode location, and a communicative coupler assembly that electrically couples the first electrode and the second electrode in parallel.

As yet another example, an esophageal intubation assembly is provided that may include a catheter including a body structure extending along a body structure length from a proximal body end to a distal body end, a passageway extending within the body structure and along at least a portion of the body structure length from a proximal passageway end to a distal passageway end, a proximal passageway opening passing through the body structure at a proximal passageway opening location for fluidly coupling the passageway with an ambient environment of the body structure at the proximal passageway opening location, and a distal passageway opening passing through the body structure at a distal passageway opening location for fluidly coupling the passageway with an ambient environment of the body structure at the distal passageway opening location, wherein the distal passageway opening location is distal of the proximal passageway opening location along the body structure length, and cardiac stimulation circuitry including an electrode positioned about the body structure and a communicative coupler assembly electrically coupling the electrode to a coupler connector, wherein the coupler connector is configured to be removably coupled to a device connector of a pacing device and the electrode includes an electrode structure configured to expand and contract.

As yet another example, an esophageal intubation assembly is provided for use with a pacing device including a first pacing device connector and a second pacing device connector, the assembly may include a catheter including a body structure extending along a body structure length from a proximal body end to a distal body end, a passageway extending within the body structure and along at least a portion of the body structure length from a proximal passageway end to a distal passageway end, a proximal passageway opening passing through the body structure at a proximal passageway opening location for fluidly coupling the passageway with an ambient environment of the body structure at the proximal passageway opening location, and a distal passageway opening passing through the body structure at a distal passageway opening location for fluidly coupling the passageway with an ambient environment of the body structure at the distal passageway opening location, wherein the distal passageway opening location is distal of the proximal passageway opening location along the body structure length, a safety device including a first safety device connector configured to be removably coupled to the first pacing device connector, a second safety device connector configured to be removably coupled to the second pacing device connector, a third safety device connector, a fourth safety device connector, first safety circuitry electrically coupled between the first safety device connector and the third safety device connector, and second safety circuitry electrically coupled between the second safety device connector and the fourth safety device connector, and cardiac stimulation circuitry including a first electrode coupled to the body structure, a first communicative coupler assembly electrically coupling the first electrode to a first coupler connector, wherein the first coupler connector is configured to be coupled to the third safety device connector, a second electrode, and a second communicative coupler assembly electrically coupling the second electrode to a second coupler connector, wherein the second coupler connector is configured to be coupled to the fourth safety device connector, and wherein at least one of the following is true: the first safety circuitry includes a fuse configured to prevent a signal with an energy above a particular energy threshold from passing from the first safety device connector to the third safety device connector or the second safety circuitry includes a diode configured to prevent current from flowing from the second safety device connector to the fourth safety device connector.

This Summary is provided only to present some example embodiments, so as to provide a basic understanding of some aspects of the subject matter described in this document. Accordingly, it will be appreciated that the features described in this Summary are only examples and should not be construed to narrow the scope or spirit of the subject matter described herein in any way. Unless otherwise stated, features described in the context of one example may be combined or used with features described in the context of one or more other examples. Other features, aspects, and advantages of the subject matter described herein will become apparent from the following Detailed Description, Figures, and Claims.

BRIEF DESCRIPTION OF THE DRAWINGS

The discussion below makes reference to the following drawings, in which like reference characters refer to like parts throughout, and in which:

FIG. 22 is a side elevational view of a portion of another pacing intubation assembly, according to some embodiments of the disclosure;

FIG. 22A is another side elevational view of the pacing intubation assembly of FIG. 22, taken from line XXIIA-XXIIA of FIG. 22, according to some embodiments of the disclosure;

FIG. 22B is a cross-sectional view of the pacing intubation assembly of FIG. 22, taken from line XXIIB-XXIIB of FIG. 22, according to some embodiments of the disclosure; and FIG. 22C is side elevational view of a portion of the pacing intubation assembly of FIG. 22, according to some embodiments of the disclosure.

DETAILED DESCRIPTION OF THE DISCLOSURE

Figure 1:
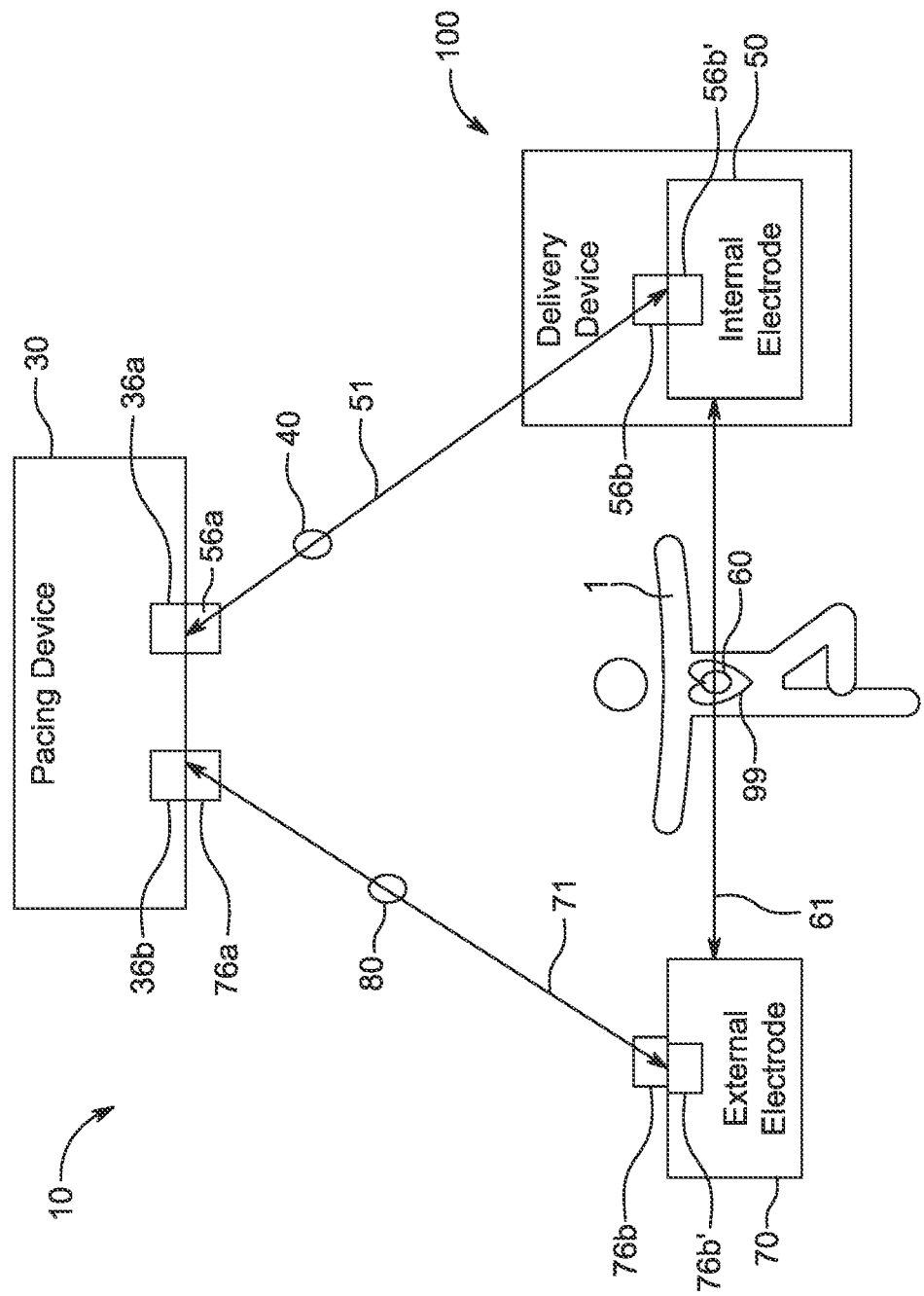
FIG. 1 is a schematic diagram illustrating a pacing intubation system, according to some embodiments of the disclosure.

Esophageal intubation assemblies with integrated capability for cardiac stimulation and gastric decompression/access and methods for using and making the same are provided.

Assemblies may be provided for enabling a healthcare provider to provide electrical pacing of a patient's ventricles (e.g., temporarily (e.g., until a permanent pacemaker can be implemented)). The assemblies may be configured to provide pacing (e.g., temporary electrical pacing) and, additionally or alternatively, access to gastric contents of a patient (e.g., intubation (e.g., esophageal intubation)) and/or cardioversion and/or defibrillation in a quick, reliable, comfortable, and/or non-invasive manner (e.g., for a patient with an instance of critical bradycardia (e.g., low and/or slow heart rate) and/or hypotension and/or cardiac electrical instability), such as until a more permanent device can be placed. In some embodiments, because certain patients may be critically ill and gastric distension may pose an aspiration risk to them and/or because certain patients may oftentimes be endotracheally intubated, gastric decompression may be useful if not a necessity. For example, such assemblies may be configured to incorporate the function of gastric decompression and/or cardiac stimulation. For a patient presenting with critical bradycardia, it may be useful if not necessary to provide parenteral electrical impulses to the patient's heart to help the patient's heartbeat at a safe rate. If a patient's heart beats too slowly, their blood pressure can drop and they can suffer cardiac arrest. This is a clinical scenario that emergency physicians or other healthcare providers may be well trained in recognizing and treating. Sometimes, treatment may involve placing pads on the patient's chest wall and administering electrical impulses across the thorax to stimulate the heart. This may be very painful for the patients, who are oftentimes awake during this time. A next step can be a technically challenging and invasive procedure that may involve the placement of a catheter through a large vein in the patient's neck, floating it into the heart, and providing electrical stimulus to the heart muscle directly. Therefore, an assembly that can be placed within a patient to provide cardiac pacing with minimal pain (e.g., non-invasively, quickly, etc.) would be beneficial. The assembly may be configured to apply electrical stimulus to the heart using an electrode that may be positioned within the patient (e.g., within any suitable passageway within the patient), such as through a catheter in the esophagus. Such an electrode may be delivered into the patient for providing cardiac pacing using any suitable device, such as a device that may additionally or alternatively be used to provide gastric decompression or any other suitable relief (e.g., an intubation or catheter assembly (e.g., for catheterization (e.g., gastric catheterization), nasogastric intubation, tracheal intubation, esophageal intubation, balloon tamponade, etc.), or any other suitable assembly for use in any suitable procedure with respect to any suitable patient), as a full or distended stomach can pose a significant vomiting and/or aspiration risk and therefore critically ill patients may be given a nasogastric tube for gastric decompression. Therefore, assemblies of this disclosure may incorporate features and/or functionality of an esophageal cardiac pacer (e.g., a pacer (e.g., a unipolar pacer) with an electrode to be positioned in the esophagus (e.g., esothoracic) and/or in the gastric fundus (e.g., gastrothoracic)) as well as a nasogastric decompression tube or any other suitable intubation tube assembly. The assembly may be provided as a nasogastric pacing catheter or as a unipolar esophageal pacing system that may be configured to include any suitable features to better integrate the unipolar design and internal electrode(s) with the functionality of a delivery assembly (e.g., an indwelling naso/orogastric tube assembly), including, but not limited to, (1) multiple internal electrodes (e.g., as electrically coupled in parallel) that may be positioned in different positions along the delivery assembly such that the different electrodes may distribute current equally between each internal electrode and an external (e.g., ground) electrode, (2) features that may augment or enhance contact (e.g., maintain contact and/or promote retention) between a patient's internal tissue (e.g., esophageal wall) and a delivery assembly and/or its coupled internal electrode(s), (3) features that may allow for a safe and seamless integration of the delivery assembly and associated electrode(s) with various types of pulse generators (e.g., different types of pacing devices 30 (e.g., biphasic pulse generators, monophasic pulse generators, etc. (e.g., biphasic defibrillators, monophasic defibrillators, etc.))), (4) features that may allow for a larger internal electrode array to integrate in such a way as to maintain the flexibility needed for a tube of the delivery assembly, and/or the like. A unipolar electrode configuration may be specifically integrated into this assembly as unipolar configurations are able to reliably and consistently provide pacing to the ventricles of the heart. Using a unipolar design for the purpose of ventricular pacing is beneficial as atrial pacing is often ineffective in the majority of critical bradycardias.

For example, the assembly may include an electrode delivery device that may include a tube that may be configured to enter the nasopharynx or oropharynx and travel into the esophagus, then potentially through into the stomach. The tube may include a hollow center and one or more distal fenestrations to allow for drainage of stomach contents or feeding to the stomach. For example, a center or other portion of the catheter or tube may be hollow, a distal tube end may include one or more fenestrations and/or a proximal tube end may include a port to enable gastric decompression. At least one electrode may be provided on the outside of the tube, such that, when the tube has been inserted into the patient to a functional position, the electrode may be positioned at the level of the heart and may be configured to administer electrical impulses to the heart. The assembly may also include an external electrode (e.g., a chest pad electrode) that may be positioned on the outside of the patient's chest and that may be configured to receive such electrical impulses (e.g., for directing these signals anteriorly through the heart tissue). The electrodes may be electrically coupled to any suitable pacing module (e.g., at the patient's bedside) that may be configured to provide and regulate pacing activity. The other end of the tube (e.g., proximal end) may be coupled to suction to allow continued gastric decompression and/or any other machinery to accomplish any other functionality (e.g., any suitable suction apparatus, ventilator apparatus, feeding apparatus, inflation/deflation apparatus, and/or the like (not shown) may be coupled to one or more proximal openings of one or more passageways of the assembly to accomplish any suitable functionality(ies) of the system).

As shown in FIG. 1, a pacing/intubating system or assembly 10 (e.g., a transesophageal ventricular pacing system) may include any suitable pacing generator or pacing device 30, any suitable electrode(s) 50 (e.g., any suitable internal electrode(s) that may be positioned within any suitable patient 1) that may be electrically coupled to pacing device 30, and any suitable electrode(s) 70 (e.g., any suitable external electrode(s) that may be positioned on the exterior of patient 1) that may be electrically coupled to pacing device 30, where any suitable electrical signals 40 may be communicated between pacing device 30 and internal electrode(s) 50 via any suitable electrical or communicative coupler assembly 51 (e.g., one or more electrical or communicative couplers (e.g., wires, electrical splitters (e.g., for parallel coupling), circuitry (e.g., for protecting or limiting signals (e.g., fuses, diodes, etc.)), connectors, and/or the like) that may electrically couple a proximate portion of coupler 51 (e.g., a coupler connector 56a that may be electrically coupled to a connector of pacing device 30) to one or more distal portions of coupler 51 (e.g., one or more coupler connectors 56*b* that may be electrically coupled to an internal electrode 50)), where any suitable electrical signals 60 may be communicated between internal electrode(s) 50 and external electrode(s) 70 via one or more paths 61 (e.g., a path that preferably is via heart 99 of patient 1 (e.g., to enable capture)), and/or where any suitable electrical signals 80 may be communicated between external electrode(s) 70 and pacing device 30 via any suitable electrical or communicative coupler assembly 71 (e.g., one or more electrical or communicative couplers (e.g., wires, electrical splitters (e.g., for parallel coupling), circuitry (e.g., for protecting or limiting signals (e.g., fuses, diodes, etc.)), connectors, and/or the like) that may electrically couple a proximate portion of coupler 71 (e.g., a coupler connector 76*a* that may be electrically coupled to a connector of pacing device 30) to one or more distal portions of coupler 71 (e.g., a coupler connector 76*b* that may be electrically coupled to an external electrode 70)). Additionally, as shown, assembly 10 may include any suitable delivery device 100 that may be configured to deliver internal electrode(s) 50 into a functional position within patient 1. The size and shapes of any portion(s) of delivery device assembly 100 and/or electrode(s) 50 and/or electrode(s) 70 may vary based on the size and/or age of the intended patient (e.g., smaller and/or shorter for pediatric patients). Moreover, assembly 10 may include other components not combined or included in FIG. 1 and/or several instances of the components shown in FIG. 1. For the sake of simplicity, only one of each of the components (e.g., electrodes) of assembly 10 is shown in FIG. 1. Cardiac stimulation circuitry of system 10 may include any suitable circuitry, including, but not limited to, electrode(s) 50, communicative coupler assembly 51, electrode(s) 70, communicative coupler assembly 71, pacing device 30, and/or the like (e.g., a safety device 20 and/or an adaptor device 90).

Figure 1A:
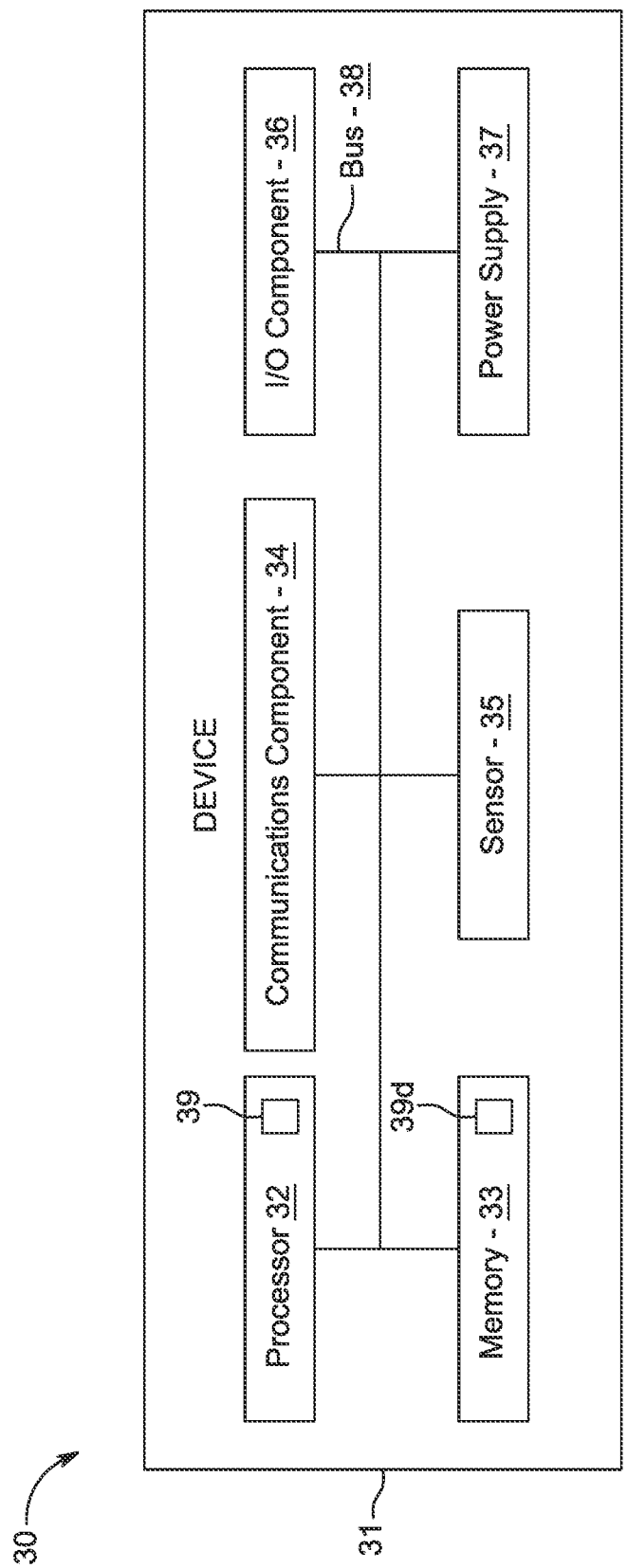
FIG. 1A is a more detailed schematic view of a device of the system of FIG. 1.

As shown in FIG. 1A, pacing device 30 may include a processor component 32, a memory component 33, a communications component 34, a sensor 35, an input/output ("I/O") component 36, a power supply component 37, a housing 31, and/or a bus 38 that may provide one or more wired or wireless communication links or paths for transferring data and/or power to, from, or between various other components of device 30 and/or to, from, or between various electrodes (e.g., electrode(s) 50 and/or electrode(s) 70). In some embodiments, one or more components of device 30 may be combined or omitted. Moreover, device 30 may include other components not combined or included in FIG. 1A and/or several instances of the components shown in FIG. 1A. For the sake of simplicity, only one of each of the components of device 30 is shown in FIG. 1A. I/O component 36 may include at least one input component (e.g., button, mouse, keyboard, etc.) to receive information from a user and/or at least one output component (e.g., audio speaker, video display, haptic component, etc.) to provide information to a user, such as a touch screen that may receive input information through a user's touch of a display screen and that may also provide visual information to a user via that same display screen. An I/O component 36 may also include any suitable electrode, such as electrode 50 and/or electrode 70. Memory 33 may include one or more storage mediums or media, including for example, a hard-drive, flash memory, permanent memory such as read-only memory ("ROM"), semi-permanent memory such as random access memory ("RAM"), any other suitable type of storage component, or any combination thereof (e.g., for storing any suitable data (e.g., data 39*d*)). Communications component 34 may be provided to allow device 30 to communicate with one or more other devices (e.g., EKG machine or any other suitable healthcare provider device or otherwise) using any suitable communications protocol. Communications component 34 can be operative to create or connect to a communication network or link of a network. Communications component 34 can provide wireless communications using any suitable short-range or long-range communications protocol, such as Wi-Fi (e.g., an 802.11 protocol), Bluetooth, ultra-wideband, radio frequency systems (e.g., 1200 MHZ, 2.4 GHz, and 5.6 GHz communication systems), near field communication ("NFC"), infrared, protocols used by wireless and cellular telephones and personal e-mail devices, or any other protocol supporting wireless communications. Communications component 34 can also be operative to connect to a wired communications link or directly to another data source wirelessly or via one or more wired connections or other suitable connection type(s). Communications component 34 may be a network interface that may include the mechanical, electrical, and/or signaling circuitry for communicating data over physical links that may be coupled to other devices of a network. Such network interface(s) may be configured to transmit and/or receive any suitable data using a variety of different communication protocols, including, but not limited to, TCP/IP, UDP, ATM, synchronous optical networks ("SONET"), any suitable wired protocols or wireless protocols now known or to be discovered, Frame Relay, Ethernet, Fiber Distributed Data Interface ("FDDI"), and/or the like. In some embodiments, one, some, or each of such network interfaces may be configured to implement one or more virtual network interfaces, such as for Virtual Private Network ("VPN") access.

Sensor 35 may be any suitable sensor that may be configured to sense any suitable data for device 30 (e.g., location-based data via a GPS sensor system, motion data, environmental data, biometric data, etc.). Sensor 35 may be a sensor assembly that may include any suitable sensor or any suitable combination of sensors operative to detect movements of device 30 and/or of any user thereof and/or any other characteristics of device 30 and/or of its environment (e.g., physical activity or other characteristics of a user of device 30, light content of the device environment, gas pollution content of the device environment, noise pollution content of the device environment, altitude of the device, etc.). Sensor 35 may include any suitable sensor(s), including, but not limited to, one or more of a GPS sensor, wireless communication sensor, accelerometer, directional sensor (e.g., compass), gyroscope, motion sensor, pedometer, passive infrared sensor, ultrasonic sensor, microwave sensor, a tomographic motion detector, a camera, a biometric sensor, a light sensor, a timer, or the like. One or more biometric sensors may be multi-modal biometric sensors and/or operative to detect long-lived biometrics, modern liveness (e.g., active, passive, etc.) biometric detection, and/or the like. Sensor 35 may include a microphone, camera, scanner (e.g., a barcode scanner or any other suitable scanner that may obtain product identifying information from a code, such as a linear barcode, a matrix barcode (e.g., a quick response ("QR") code), or the like), proximity sensor, light detector, temperature sensor, motion sensor, biometric sensor, line-in connector for data and/or power, and/or combinations thereof. In some examples, each sensor can be a separate device, while, in other examples, any combination of two or more of the sensors can be included within a single device. For example, a gyroscope, accelerometer, photoplethysmogram, galvanic skin response sensor, and temperature sensor can be included within a wearable electronic device, such as a smart watch, while a scale, blood pressure cuff, blood glucose monitor, SpO2 sensor, respiration sensor, posture sensor, stress sensor, and asthma inhaler can each be separate devices. While specific examples are provided, it should be appreciated that other sensors can be used and other combinations of sensors can be combined into a single device. Sensor 35 may be embedded in a body (e.g., housing 31) of device 30, such as along a bottom surface that may be operative to contact a user, or can be positioned at any other desirable location (e.g., one or more sensor(s) 35 may be embedded in an electrode (e.g., electrode 70)). In some examples, different sensors can be placed in different locations inside or on the surfaces of device 30 (e.g., some located inside housing 31 and some attached to an attachment mechanism (e.g., a wrist band coupled to a housing of a wearable device), or the like). In other examples, one or more sensors can be worn by a user separately as different parts of a single device 30 or as different devices. In such cases, the sensors can be configured to communicate with device 30 using a wired and/or wireless technology (e.g., via communications component 34). In some examples, sensors can be configured to communicate with each other and/or share data collected from one or more sensors.

Power supply 37 can include any suitable circuitry for receiving and/or generating power, and for providing such power to one or more of the other components of device 30. For example, power supply assembly 37 can be coupled to a power grid (e.g., when device 30 is not acting as a portable device or when a battery of the device is being charged at an electrical outlet with power generated by an electrical power plant). As another example, power supply assembly 37 may be configured to generate power from a natural source (e.g., solar power using solar cells). As another example, power supply assembly 37 can include one or more batteries for providing power (e.g., when device 30 is acting as a portable device). Device 30 may also be provided with a housing 31 that may at least partially enclose one or more of the components of device 30 for protection from debris and other degrading forces external to device 30. Each component of device 30 may be included in the same housing 31 (e.g., as a single unitary device, such as a portable media device or server) and/or different components may be provided in different housings (e.g., a keyboard input component may be provided in a first housing that may be communicatively coupled to a processor component and a display output component that may be provided in a second housing, such as in a desktop computer set-up). In some embodiments, device 30 may include other components not combined or included in those shown or several instances of the components shown.

Processor 32 may be used to run one or more applications, such as an application 39 that may be accessible from memory 33 (e.g., as a portion of data 39d) and/or any other suitable source (e.g., from any other device in its system). Application 39 may include, but is not limited to, one or more operating system applications, firmware applications, communication applications (e.g., for enabling communication of data between devices), third party service applications, internet browsing applications (e.g., for interacting with a website provided by a third party subsystem, application programming interfaces ("APIs"), software development kits ("SDKs"), proprietary applications (e.g., a web application or a native application) for enabling device 30 to interact with an online service and/or one or more other suitable devices and/or the like, which may include applications for generating any suitable pulses or other suitable heart treatment signals. For example, processor 32 may load an application 39 as an interface program to determine how instructions or data received via an input component of I/O component 36 or other component of device 30 (e.g., sensor 35 and/or communications component 34) may manipulate the way in which information may be stored (e.g., in memory 33) and/or provided via an output component of I/O component 36 and/or communicated to another system device via communications component 34. As one example, application 39 may be a third party application that may be running on device 30 that may be loaded on device 30 in any suitable manner, such as via an application market (e.g., using communications component 34), such as the Apple App Store or Google Play, or that may be accessed via an internet application or web browser (e.g., by Apple Safari or Google Chrome) that may be running on device 30 and that may be pointed to a uniform resource locator ("URL") whose target or web resource may be managed by or otherwise affiliated with any suitable entity. Application 39 (e.g., alone or in combination with any signal(s) 80 received from electrode 70) may dictate signal(s) 40 provided to electrode 50. For example, the internal and external electrodes may both be able to provide transmission of electrical impulse and sense the patient's cardiac activity, thereby informing the pacing generator as to the heart's activity.

Device 30 may be any portable, mobile, wearable, implantable, or hand-held electronic device configured to operate with assembly 10. Alternatively, device 30 may not be portable during use, but may instead be generally stationary. Device 30 can include, but is not limited to, a media player, video player, still image player, game player, other media player, music recorder, movie or video camera or recorder, still camera, other media recorder, radio, medical equipment, domestic appliance, smart appliance, transportation vehicle instrument, musical instrument, calculator, cellular telephone, other wireless communication device, personal digital assistant, remote control, pager, computer (e.g., a desktop, laptop, tablet, server, etc.), monitor, television, stereo equipment, set up box, set-top box, wearable device (e.g., an Apple Watch™ by Apple Inc.), boom box, modem, router, printer, kiosk, beacon, server, and any combinations thereof that may be useful as a patient treatment device.

Delivery device 100 may be any suitable device that may be configured to deliver internal electrode(s) 50 into a functional position within patient 1. FIGS. 2 and 2A-2D show an illustrative delivery device assembly 100 in various configurations or stages of use with respect to a patient 1. Assembly 100 may be an intubation or catheter assembly (e.g., for catheterization (e.g., gastric catheterization), nasogastric intubation, orogastric intubation, tracheal intubation, esophageal intubation, balloon tamponade, etc.), or any other suitable assembly for use in any suitable procedure with respect to any suitable patient 1 while also being a delivery device for positioning electrode(s) 50 in a functional position within patient 1. As shown in FIGS. 2 and 2A-2D, for example, assembly 100 may extend between a proximal or first assembly end 101, which may have an outer cross-sectional dimension (e.g., diameter) DP, and a distal or second assembly end 109, which may have an outer cross-sectional dimension (e.g., diameter) DD. Assembly 100 may include at least one tube or tube subassembly 110 providing a body structure 112 (e.g., catheter or tube) that may extend between ends 101 and 109. Tube subassembly 110 may include at least one tube wall 113 that may define at least one internal or intubation lumen or passageway 115 extending within and along at least a portion of assembly 100. Wall 113 may also include at least one proximal or first tube opening 102 that may provide access to passageway 115 (e.g., fluid communication between passageway 115 and an ambient environment of assembly 100) at or near end 101 of assembly 100 and at least one distal or second tube opening 108 that may provide access to passageway 115 (e.g., fluid communication between passageway 115 and an ambient environment of assembly 100) at or near end 109 of assembly 100 (e.g., a first opening 108 (e.g., opening 108a of FIGS. 3 and 4) may be an opening at the distal end of passageway 115 (e.g., through end 109 of body structure 112), while one or more other openings 108 (e.g., openings 108b of FIG. 5) may be provided through wall 113 along a side of body structure 112 (e.g., proximal of distal end 109)). Moreover, assembly 100 may also include an expander or expander subassembly 160 that may extend along at least a portion of tube subassembly 110, where expander subassembly 160 may include an external surface 163. Although expander subassembly 160 is described in detail herein, it is to be understood that assembly 100 need not include a distinct expander subassembly in order for assembly 100 to properly position and utilize system 10 as a unipolar esophageal pacing system. As also shown in FIGS. 2 and 2A-2D, for example, patient 1 may include a passageway wall 13 that may define a passageway 15 (e.g., throat, esophagus) that may extend between at least one proximal or first access opening 11 and a distal or second opening 19. Moreover, patient 1 may include a target wall 93 that may define at least a portion of a target space 95 (e.g., stomach, esophagus, gastric fundus, etc.), where a proximal or first target opening 91 of wall 93 may be coupled to opening 19 of passageway 15, such that passageway 15 may be fluidly coupled to target space 95. As shown in FIGS. 2 and 2A-2D, for example, at least a portion of passageway 15 and/or the coupling of opening 19 and opening 91 may have a cross-sectional dimension (e.g., diameter) DO, which may be a minimum dimension of patient 1 through which at least a portion of assembly 100 may pass or otherwise exist during any stage of use within patient 1.

Figure 2:
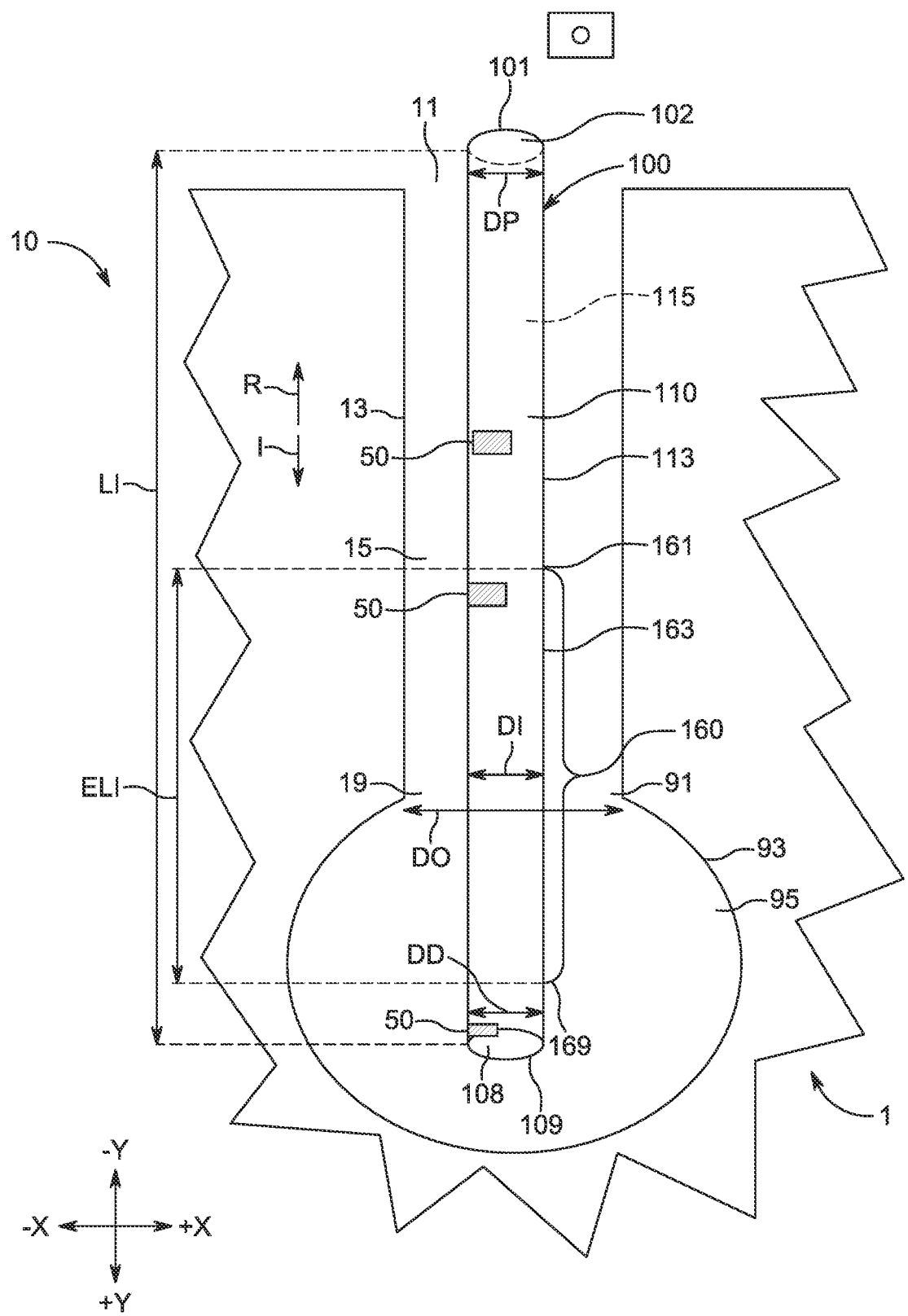
FIG. 2 is a cross-sectional view of a patient with a pacing intubation assembly in an insertion state, according to some embodiments of the disclosure.

When in an insertion state (see, e.g., FIG. 2), assembly 100 may be inserted into patient 1 to a particular position, and then assembly 100 may be re-configured into an expanded state (see, e.g., FIG. 2A and/or FIG. 2B and/or FIG. 2C) within patient 1 such that assembly 100 may be safely used within patient 1. After use of assembly 100 in its expanded state within patient 1, assembly 100 may be re-configured into a removal state (see, e.g., FIG. 2D) within patient 1 for removal of assembly 100 from patient 1. For example, as shown by FIG. 2, assembly 100 may first be configured in an insertion state or configuration such that assembly 100 may then be at least partially inserted into patient 1. In some embodiments, end 109 of assembly 100 in its insertion state may be inserted into patient 1 in the direction of arrow I through opening 11, through passageway 15, through opening 19, through opening 91, and into target space 95, such that at least one opening 108 of assembly 100 may be within space 95 and/or such that at least one opening 102 of assembly 100 may be accessible to an operator O of assembly 100 (e.g., a physician or nurse or perhaps even patient 1 itself), who may be external to at least passageway 15 of patient 1. Assembly 100 may be of a length LI that may extend between end 101 and end 109 of assembly 100 in its insertion state, and where such a length provided by assembly 100 in its insertion state may vary based on the size of patient 1 and the procedure to be performed. As shown in FIG. 2, when assembly 100 is in its insertion state, no portion of expander subassembly 160 may have a cross-sectional dimension (e.g., diameter) greater than dimension DI. In some embodiments, dimension DD of end 109 and dimension DI of expander subassembly 160 in the insertion state of assembly 100 may be less than dimension DO of patient 1 such that assembly 100 in its insertion state may be safely inserted into patient 1 without damaging wall 13 and/or wall 93 of patient 1.

Figure 2A:
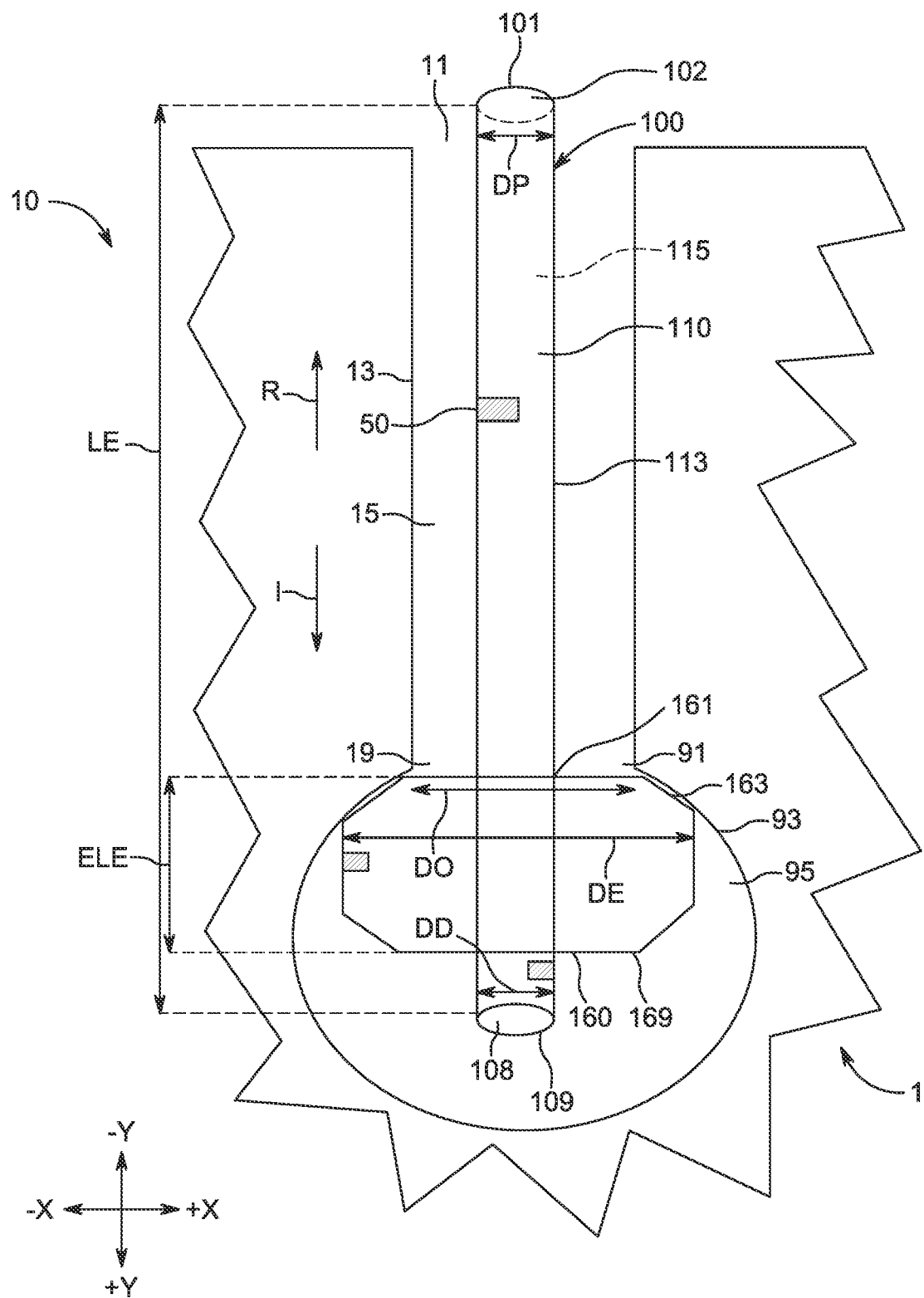
FIGS. 2A-2C are cross-sectional views, similar to FIG. 2, of the patient of FIG. 2 with the pacing intubation assembly of FIG. 2 in various illustrative expanded states, according to some embodiments of the disclosure.
Figure 2B:
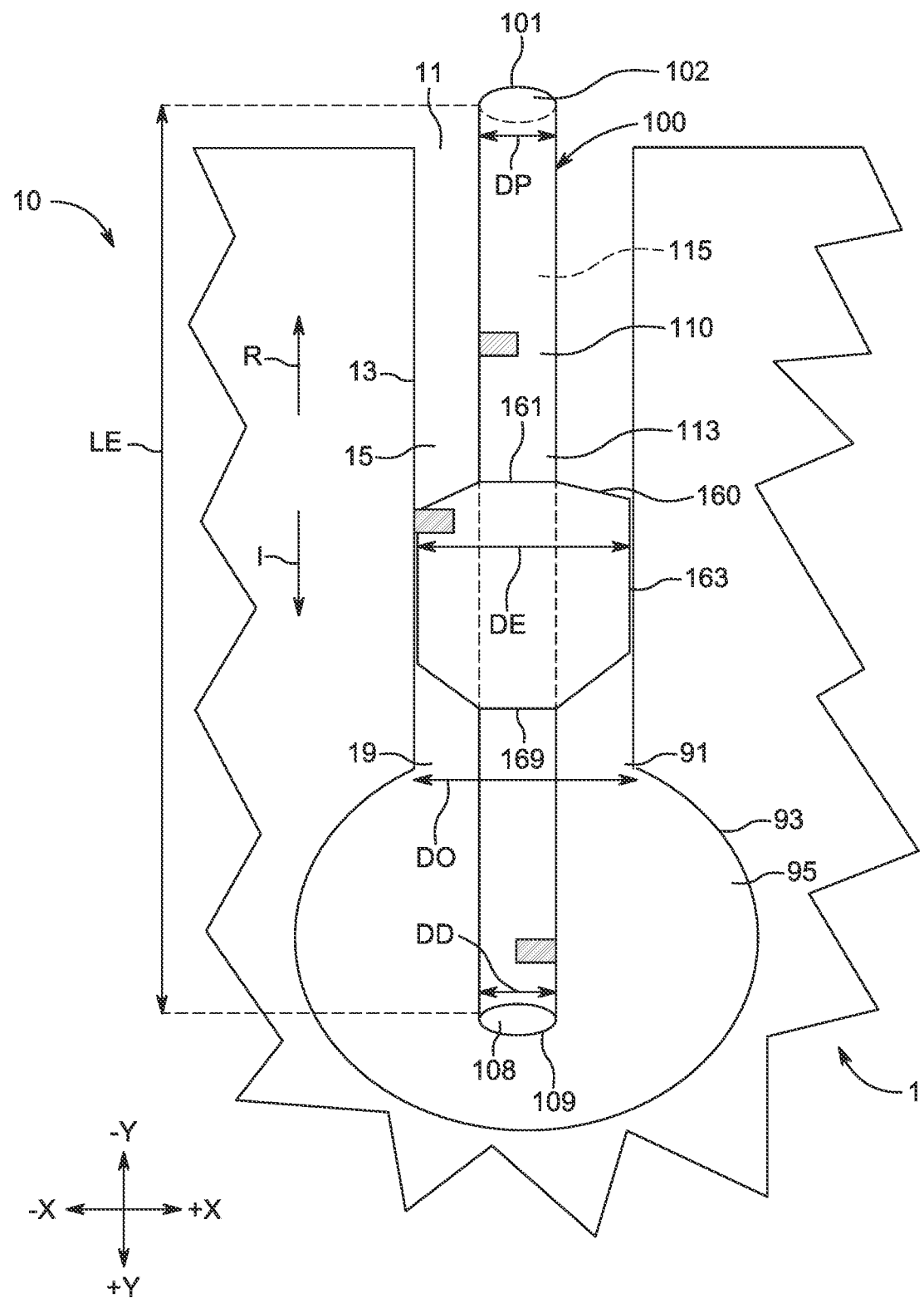
Figure 2C:
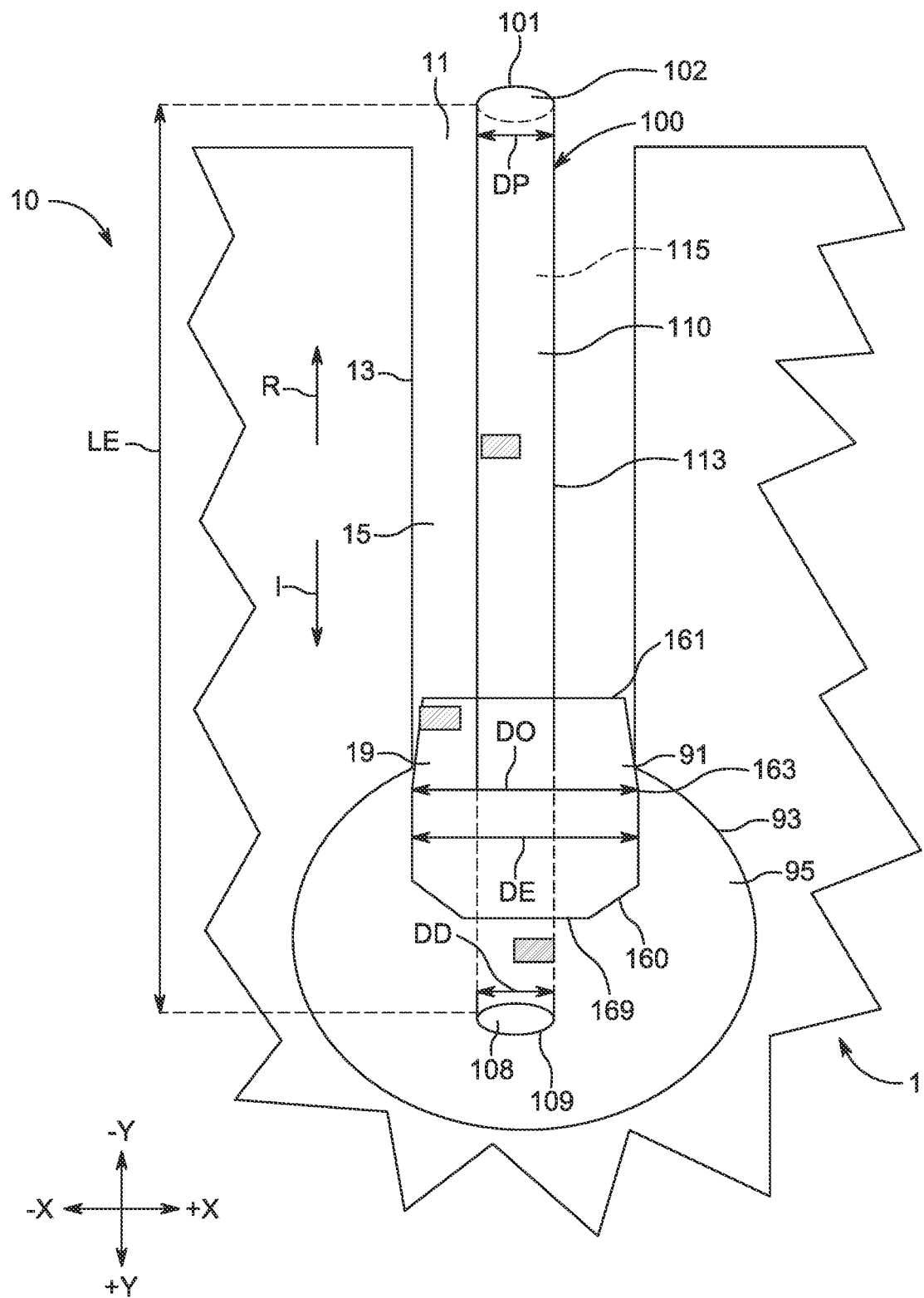

After assembly 100 has been inserted into patient 1 while assembly 100 is in its insertion state, assembly 100 may be re-configured into an expanded state within patient 1 such that assembly 100 may thereafter be safely used within patient 1. For example, as shown in each one of FIGS. 2A-2C, once assembly 100 in its insertion state has been inserted into its insertion position of FIG. 2 within patient 1, assembly 100 may be re-configured into an expanded state within patient 1 such that assembly 100 may thereafter be safely used in that expanded state within patient 1. As shown in each one of FIGS. 2A-2C, when assembly 100 is in its expanded state, at least a portion of expander subassembly 160 may have a maximum cross-sectional dimension (e.g., diameter) DE that may be at least equal to or greater than dimension DO of patient 1, such that at least a portion of wall 163 of expander subassembly 160 may contact or otherwise interact with at least a portion of wall 93 of target 95 and/or with at least a portion of wall 13 of passageway 15 for safely securing expanded assembly 100 at a particular position within patient 1 and/or for safely preventing certain material from traveling between wall 163 of expander subassembly 160 and at least a portion of wall 93 of target 95 and/or at least a portion of wall 13 of passageway 15. One or more of dimensions DE, DI, and DR may be widths defined by expander subassembly 160, where such a width may be perpendicular to a length of expander subassembly 160 (e.g., along the X-axis, which may be perpendicular to the length extending between ends 161 and 169 of an expander of expander subassembly 160 along the Y-axis). As shown in FIG. 2A, for example, all of expander subassembly 160 may be positioned within target space 95 when assembly 100 is re-configured from its insertion state into its expanded state, such that at least a portion of wall 163 of expander subassembly 160 may contact or otherwise interact with at least a portion of wall 93 of target 95. Alternatively, as shown in FIG. 2B, for example, all of expander subassembly 160 may be positioned within passageway 15 when assembly 100 is re-configured from its insertion state into its expanded state, such that at least a portion of wall 163 of expander subassembly 160 may contact or otherwise interact with at least a portion of wall 13 of passageway 15. Alternatively, as shown in FIG. 2C, for example, a first portion of expander subassembly 160 may be positioned within passageway 15 and a second portion of expander subassembly 160 may be positioned with target space 95 when assembly 100 is re-configured from its insertion state into its expanded state, such that at least a first portion of wall 163 of expander subassembly 160 may contact or otherwise interact with at least a portion of wall 13 of passageway 15 and such that at least a second portion of wall 163 of expander subassembly 160 may contact or otherwise interact with at least a portion of wall 93 of target 95. As shown in FIGS. 2A-2C, at least a portion of expander subassembly 160 may expand at least along the X-axis such that a maximum cross-sectional dimension (e.g., diameter) of expander subassembly 160 may expand from dimension DI to dimension DE when assembly 100 is reconfigured from its insertion state to its expanded state. As shown in FIGS. 2A-2C, assembly 100 may be of a length LE that may extend between end 101 and end 109 of assembly 100 in its expanded state, where such a length LE provided by assembly 100 may vary based on the size of patient 1 and may be greater than, less than, or equal to length LI of assembly 100 in its insertion state (e.g., the state of FIG. 2) and/or length LR of assembly 100 in its removal state (e.g., the state of FIG. 2D).

Once assembly 100 has been expanded into its expanded state within patient 1 (e.g., as shown in any one or more of FIGS. 2A-2C), assembly 100 may be safely used within patient 1 in any suitable way, such as in any suitable intubation and/or decompression and/or cardioversion process(es). For example, in some embodiments, expanded assembly 100 may be safely used within patient 1 for injecting material (e.g., treatment material, such as nutrients or medicine or oxygen or air) through opening 102, into and through passageway 115, then out of passageway 115 through opening 108, and into target space 95 and/or passageway 15 of patient 1, and/or for removing material (e.g., treatment material, such as waste) from target space 95 and/or passageway 15, through opening 108, into and through passageway 115, then out of passageway 115 through opening 102 away from patient 1. In certain embodiments, target space 95 may be a stomach, opening 91 may be a lower esophageal sphincter, passageway 15 may be an esophagus, pharynx, throat, and/or nasal cavity, and opening 11 may be a nostril or mouth of patient 1, where assembly 100 may be used during an intubation process. It is to be understood that assembly 100 may be used with respect to any suitable portions of any suitable patient 1 for any suitable process, where expander subassembly 160 may be expanded such that at least a portion of wall 163 of expander 160 may contact or otherwise interact with at least a portion of wall 93 of target 95 and/or with at least a portion of wall 13 of passageway 15 for safely securing expanded assembly 100 at a particular position within patient 1 (e.g., for preventing opening 108 and/or end 109 of assembly 100 from being inadvertently removed from target space 95 (e.g., in the direction of arrow R) and/or from being inadvertently inserted too far into space 95 (e.g., in the direction of arrow I)) and/or for safely preventing certain material from traveling between wall 163 of expander subassembly 160 and at least a portion of wall 93 of target 95 and/or between wall 163 of expander subassembly 160 and at least a portion of wall 13 of passageway 15 (e.g., for preventing contents of a stomach target 95 from escaping target 95 through passageway 15 about the exterior of wall 163 of expander subassembly 160 (i.e., not through assembly 100), such as towards a trachea or other portion of patient 1 between expander 160 and end 11 of passageway 15 that may cause infections and/or inflammation (e.g., in the direction of arrow R), such as when assembly 100 may be used as a nasogastric tube). Specifically, reflux of contents from the stomach back into the esophagus has been a persistent problem, especially in the presence of nasogastric tubes. Contents often attempt to travel back up from the stomach around the tube, thereby causing reflux esophagitis, aspiration pneumonitis, and/or pneumonias.

Figure 2D:
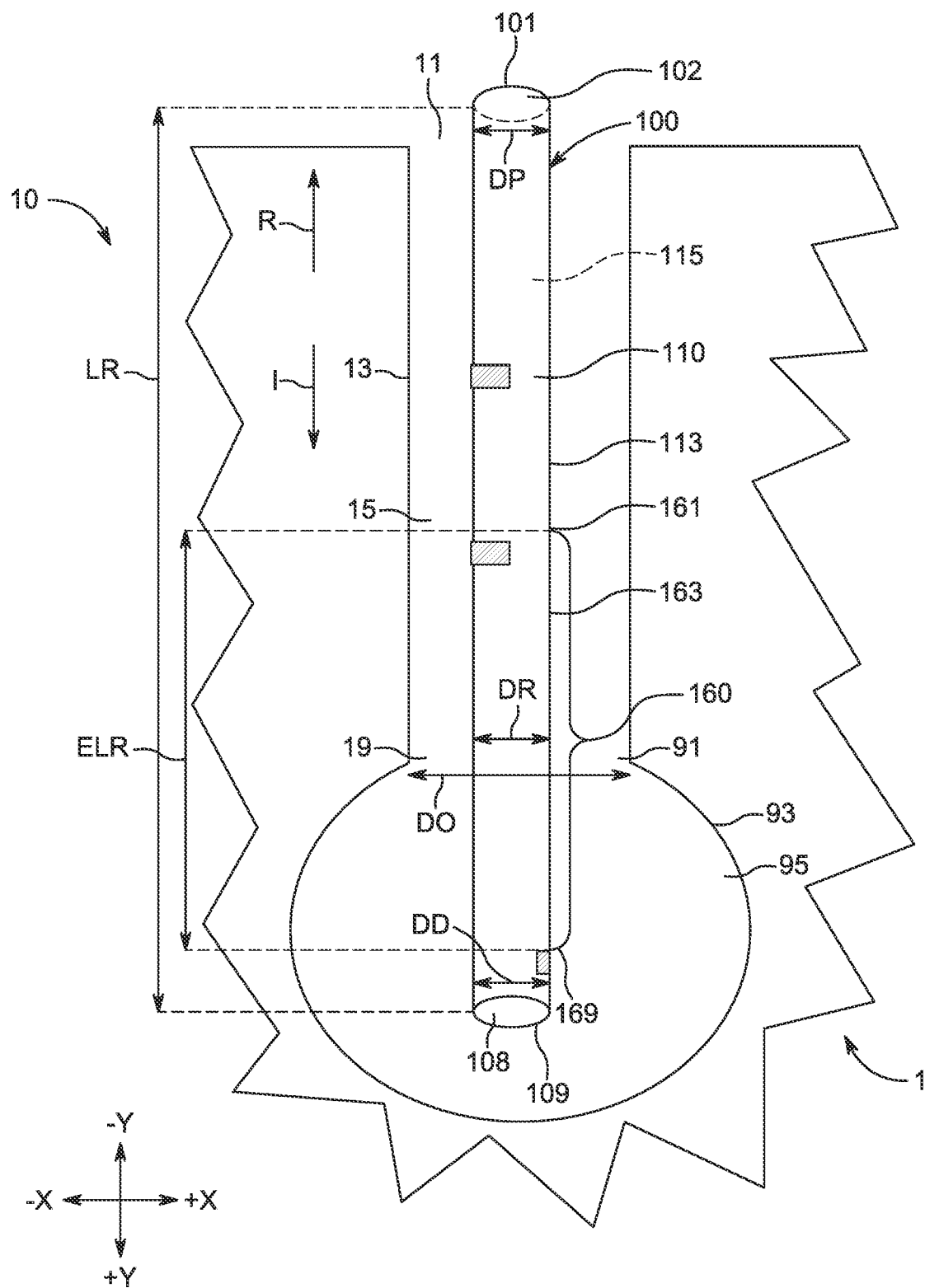
FIG. 2D is a cross-sectional view, similar to FIGS. 2 and 2A-2C, of the patient of FIGS. 2 and 2A-2C with the pacing intubation assembly of FIGS. 2 and 2A-2C in a removal state, according to some embodiments of the disclosure.

After assembly 100 has been used in its expanded state within patient 1, assembly 100 may be re-configured into a removal state such that assembly 100 may thereafter be safely removed from within patient 1 (e.g., in the direction of arrow R). For example, as shown in FIG. 2D, once assembly 100 has been used in its expanded state of any of FIGS. 2A-2C within patient 1, assembly 100 may be re-configured into a removal state within patient 1 such that assembly 100 may thereafter be safely removed in its removal state from within patient 1. For example, as shown in FIG. 2D, when assembly 100 is in its removal state, no portion of expander subassembly 160 may have a cross-sectional dimension (e.g., diameter) greater than dimension DR, where such a dimension DR provided by assembly 100 may vary based on the size of patient 1 and may be greater than, less than, or equal to dimension DI of the insertion state. In some embodiments, dimension DD of end 109 and dimension DR of expander subassembly 160 in the removal state of assembly 100 may be less than dimension DO of patient 1 such that assembly 100 in its removal state may be safely removed from patient 1 without damaging wall 13 and/or wall 93 of patient 1. In some embodiments, as shown in FIG. 2D, at least a portion of expander subassembly 160 may contract at least along the X-axis such that a maximum cross-sectional dimension (e.g., diameter) of expander 160 may contract from dimension DE to dimension DR when assembly 100 is reconfigured from its expanded state to its removal state. As shown in FIG. 2D, assembly 100 may be of a length LR that may extend between end 101 and end 109 of assembly 100 in its removal state, where such a length LR provided by assembly 100 may vary based on the size of patient 1 and may be greater than, less than, or equal to length LI of assembly 100 in its insertion state and/or length LE of assembly 100 in its expanded state. It is to be noted that, while "proximal" or "proximate" may be used herein to refer to a general direction or end of assembly 100 that may be closest to operator O of assembly 100 during use (e.g., external to patient 1), and while "distal" or "distant" may be used herein to refer to a general direction or end of assembly 100 that may be farthest from operator O of assembly 100 during use (e.g., within target 95), such directional and orientational terms may be used herein only for convenience, and that no fixed or absolute directional or orientational limitations are intended by the use of these words.

In some embodiments, expander subassembly 160 may include at least one balloon (e.g., a high volume, low pressure balloon) or any other suitable expander mechanism or component that may be inflatable by air or any other suitable fluid (e.g., gas or liquid or any other suitable substance that may be able to flow into and/or out of the expander mechanism) for enabling the expansion of at least a portion of expander subassembly 160 (e.g., from dimension DI to dimension DE), which may allow at least a portion of expander subassembly 160 to contact a wall of patient 1 for securing expanded assembly 100 at a particular position within patient 1 and/or for preventing certain material from traveling between expander subassembly 160 and a wall of patient 1.

Figure 3:
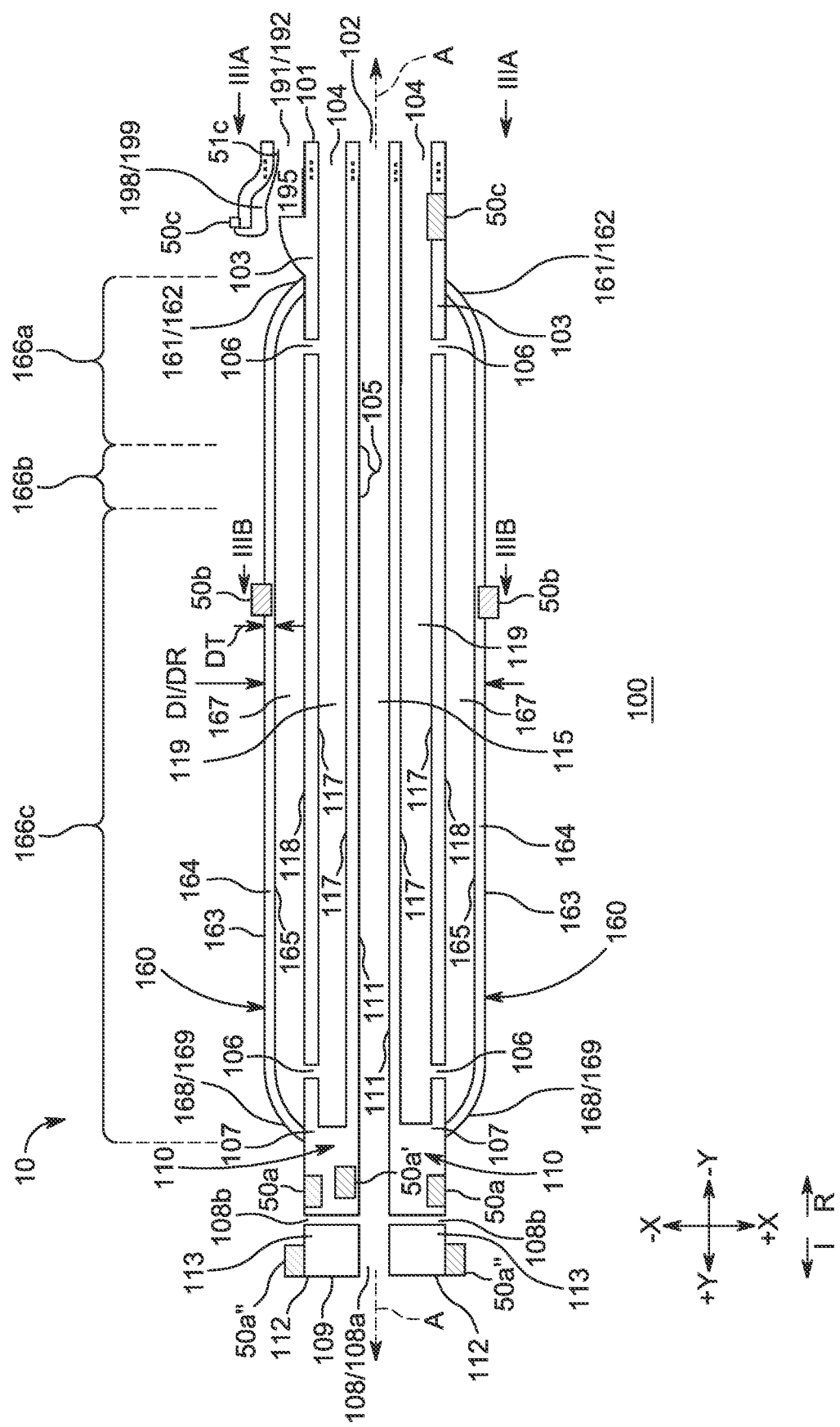
FIG. 3 is a cross-sectional view of a portion of the pacing intubation assembly of FIGS. 2 and 2A-2D in an insertion state, according to some embodiments of the disclosure.
Figure 3B:
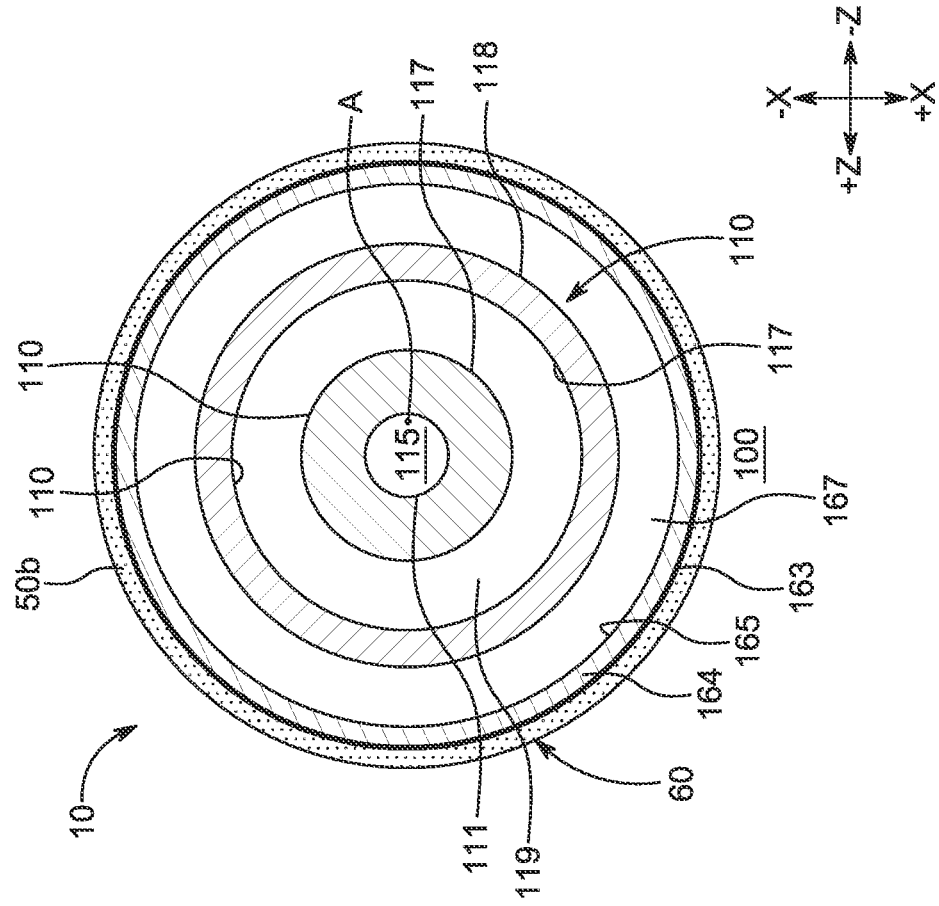
FIG. 3B is a cross-sectional view of the pacing intubation assembly of FIGS. 3 and 3A, taken from line IIIB-IIIB of FIG. 3, according to some embodiments of the disclosure.
Figure 3A:
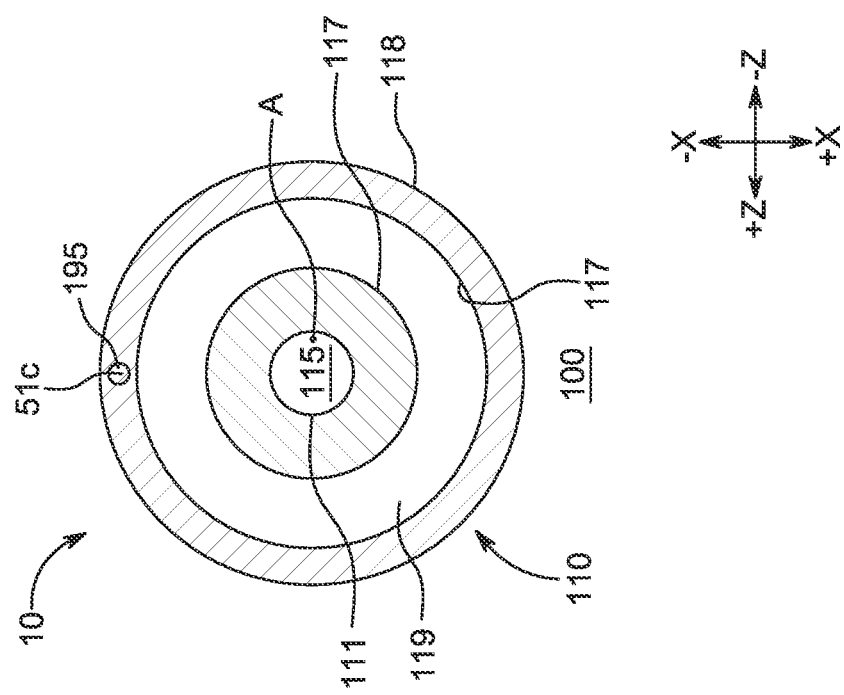
FIG. 3A is a cross-sectional view of the pacing intubation assembly of FIG. 3, taken from line IIIA-IIIA of FIG. 3, according to some embodiments of the disclosure.
Figure 4:
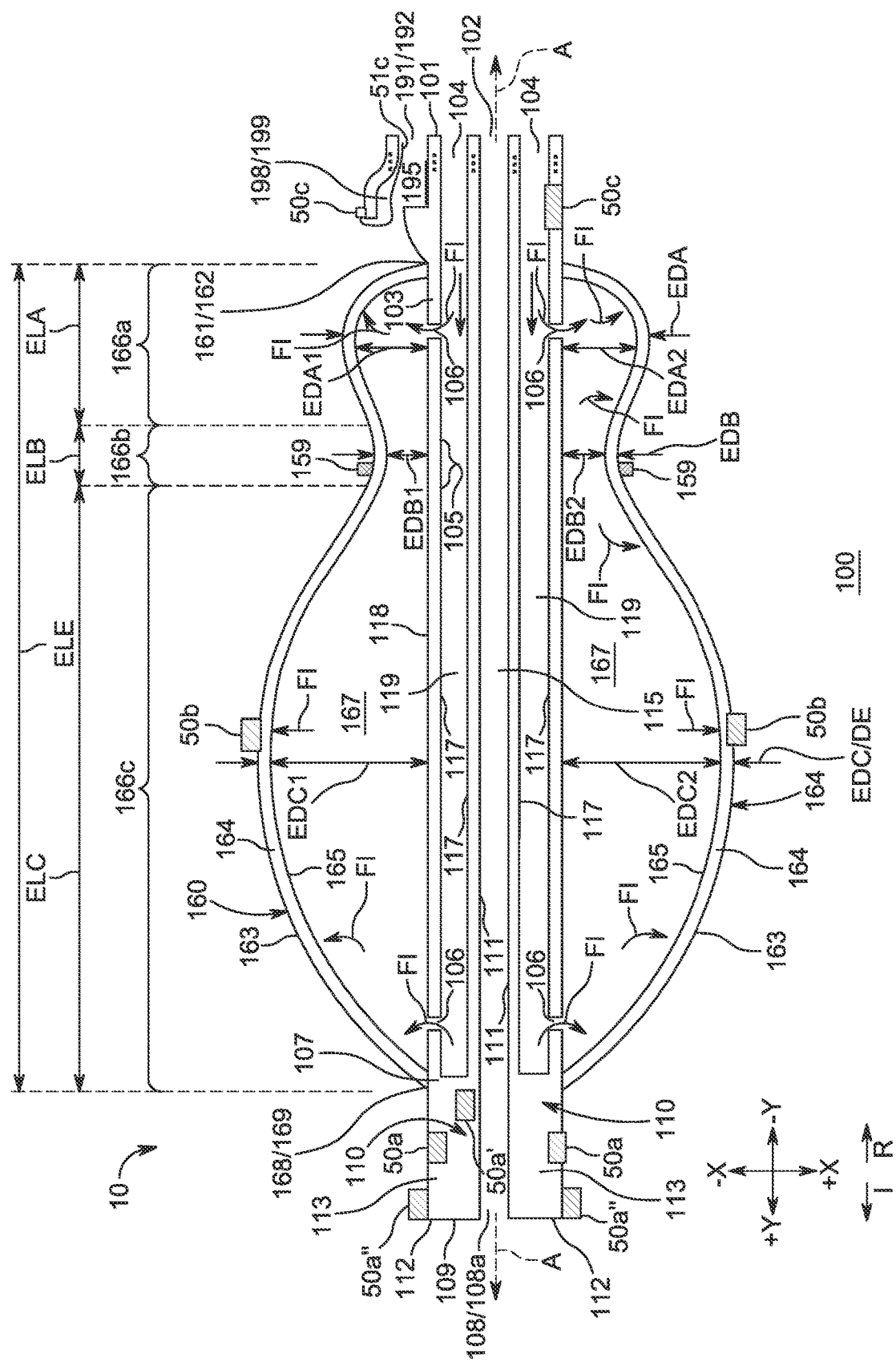
FIG. 4 is a cross-sectional view, similar to FIG. 3, of a portion of the pacing intubation assembly of FIGS. 3, 3A, and 3B in an equilibrium geometry of an expanded state, according to some embodiments of the disclosure.
Figure 5:
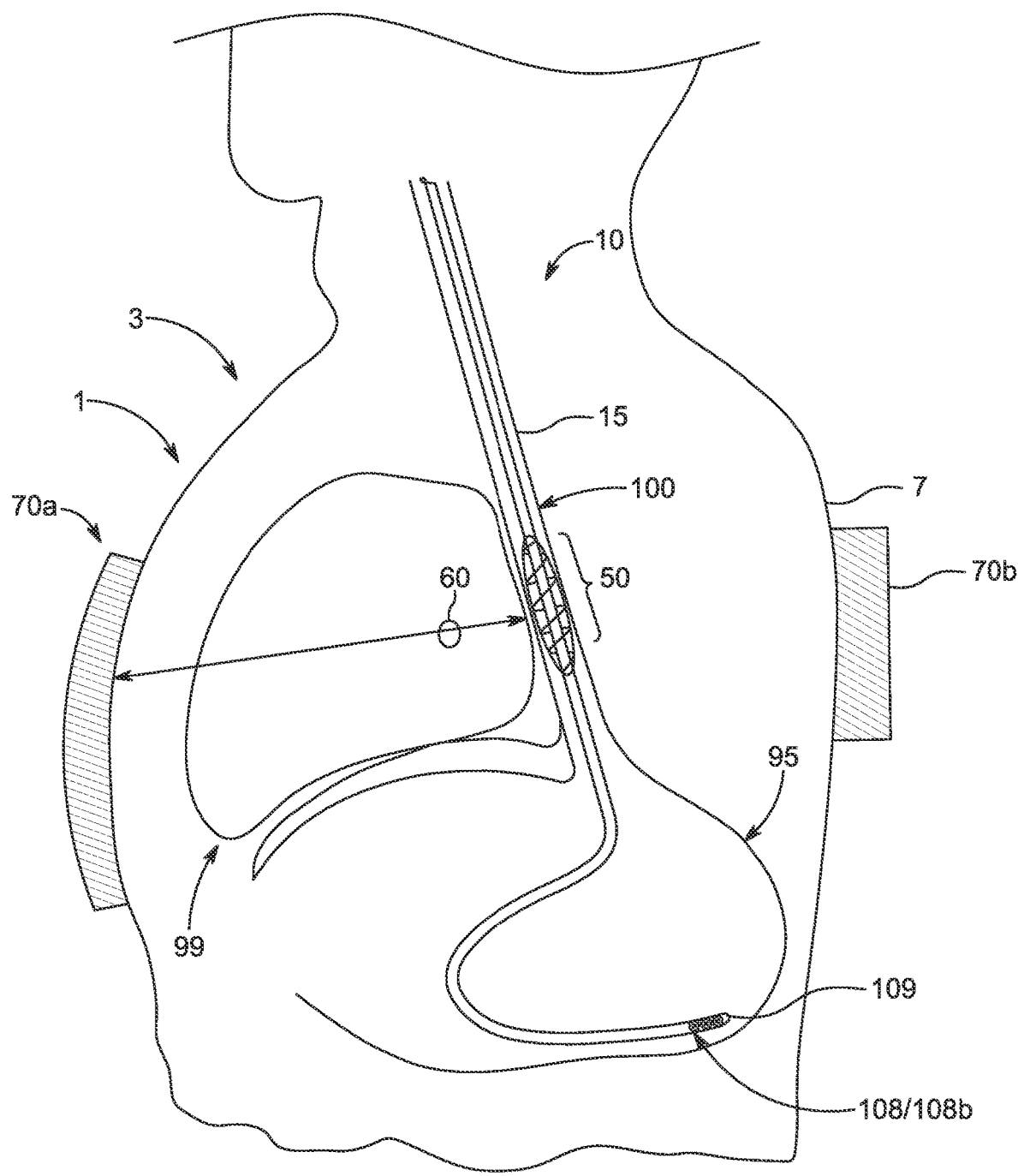
FIG. 5 is another cross-sectional view of a patient with a pacing intubation assembly in a functional state, according to some embodiments of the disclosure.
Figure 6:
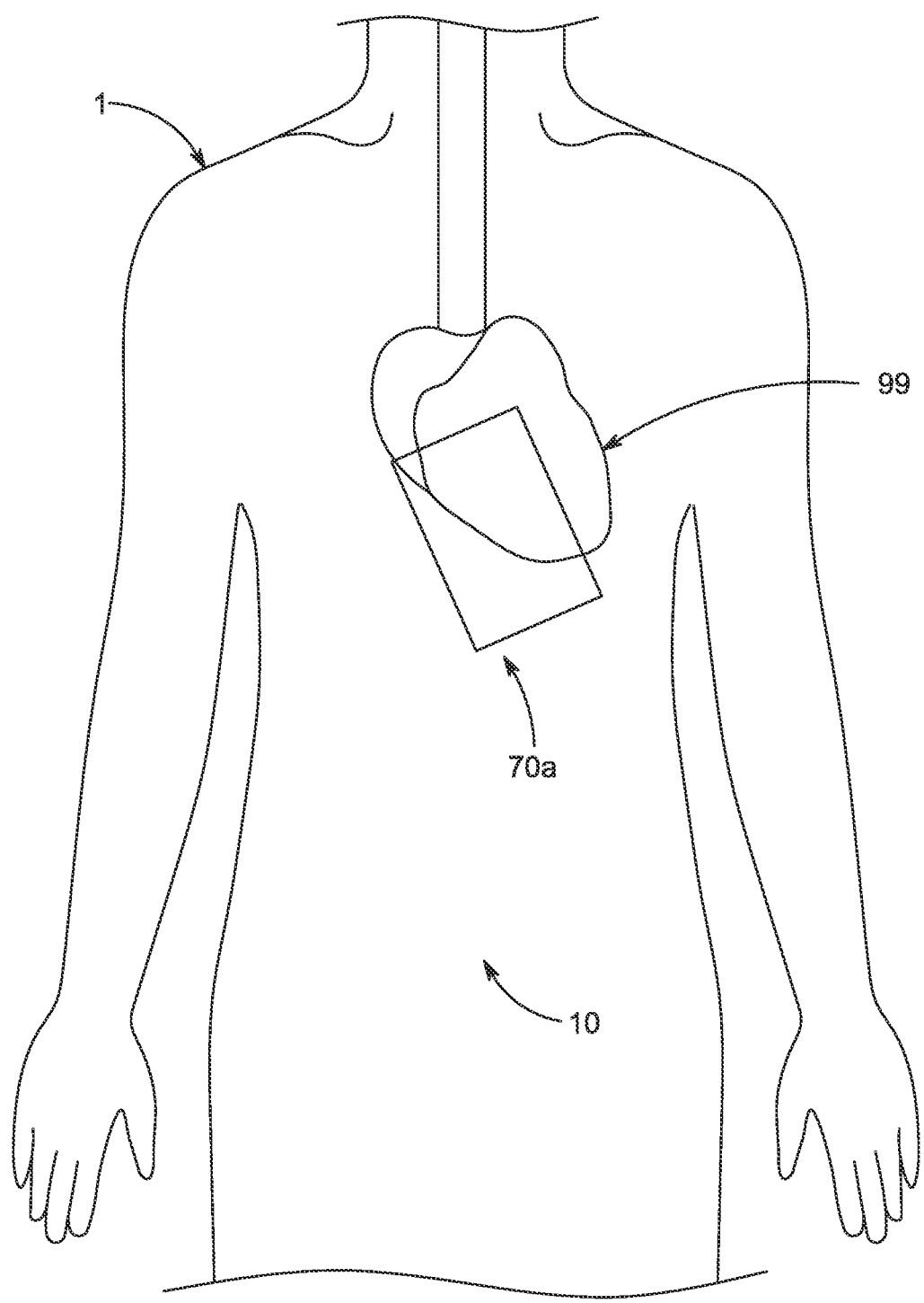
FIG. 6 is a front view of the patient with the pacing intubation system in the functional state of FIG. 5, according to some embodiments of the disclosure.

As shown in FIGS. 3, 3A, 3B, and 4, for example, assembly 100 may include tube subassembly 110 and expander subassembly 160 with an expander component 164. Tube subassembly 110 may provide a body structure 112 that may include tube wall(s) 113 that may provide one or more surfaces 111 that may define at least first passageway 115 for extending between at least first tube opening 102 that may provide access to passageway 115 at or near end 101 of assembly 100 and at least one distal or second tube opening 108 that may provide access to passageway 115 at or near end 109 of assembly 100, such that, when assembly 100 is appropriately positioned at least partially within patient 1, material may be injected through opening 102, into and through passageway 115, then out of passageway 115 through opening 108, and into target space 95 and/or passageway 15 of patient 1, and/or such that material may be removed from target space 95 and/or passageway 15, through opening 108, into and through passageway 115, then out of passageway 115 through opening 102 away from patient 1. For example, as shown in FIGS. 3 and 3A-4, passageway 115 may be a single passageway extending along a longitudinal axis of tube subassembly 110 (e.g., axis A that may extend along a Y-axis (e.g., when arranged in a straight manner, although it is to be understood that tube subassembly 110 may be configured to be flexible to bend in one or more ways (e.g., axis A may not always be completely linear along the entire length of the tube subassembly) such that the tube subassembly may navigate (e.g., be advanced through and/or retracted from) a complex anatomy))). Although, in other embodiments, passageway 115 may be provided by two or more passageways, at least one of which may at least partially not extend along a longitudinal axis of tube subassembly 110. In some embodiments, opening 102 may not be provided at end 101 of assembly 100 but may instead be provided along and/or through a side surface of tube wall(s) 113 proximal to end 101, and/or opening 108 may not be provided at end 109 of assembly 100 but may instead be provided along and/or through a side surface of tube wall(s) 113 proximal to end 109. Tube wall(s) 113 of subassembly 110 may also provide one or more exterior surfaces 118 of tube subassembly 110 along at least a portion of the length of tube subassembly 110 between ends 101 and 109.

Figure 9:
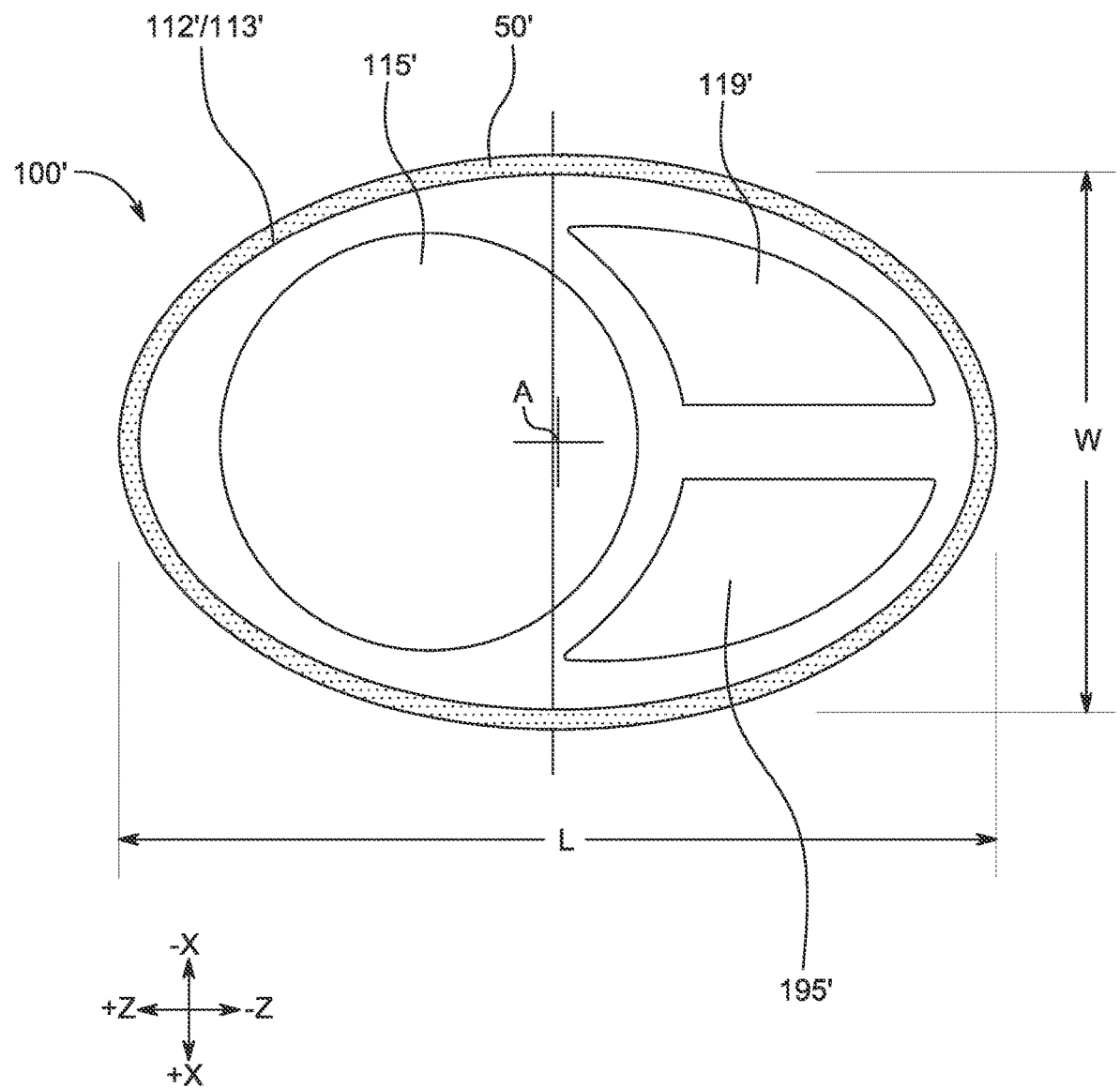
FIG. 9 is a cross-sectional view, similar to FIG. 3A, of a portion of another pacing intubation assembly, according to some embodiments of the disclosure.
Figure 11:
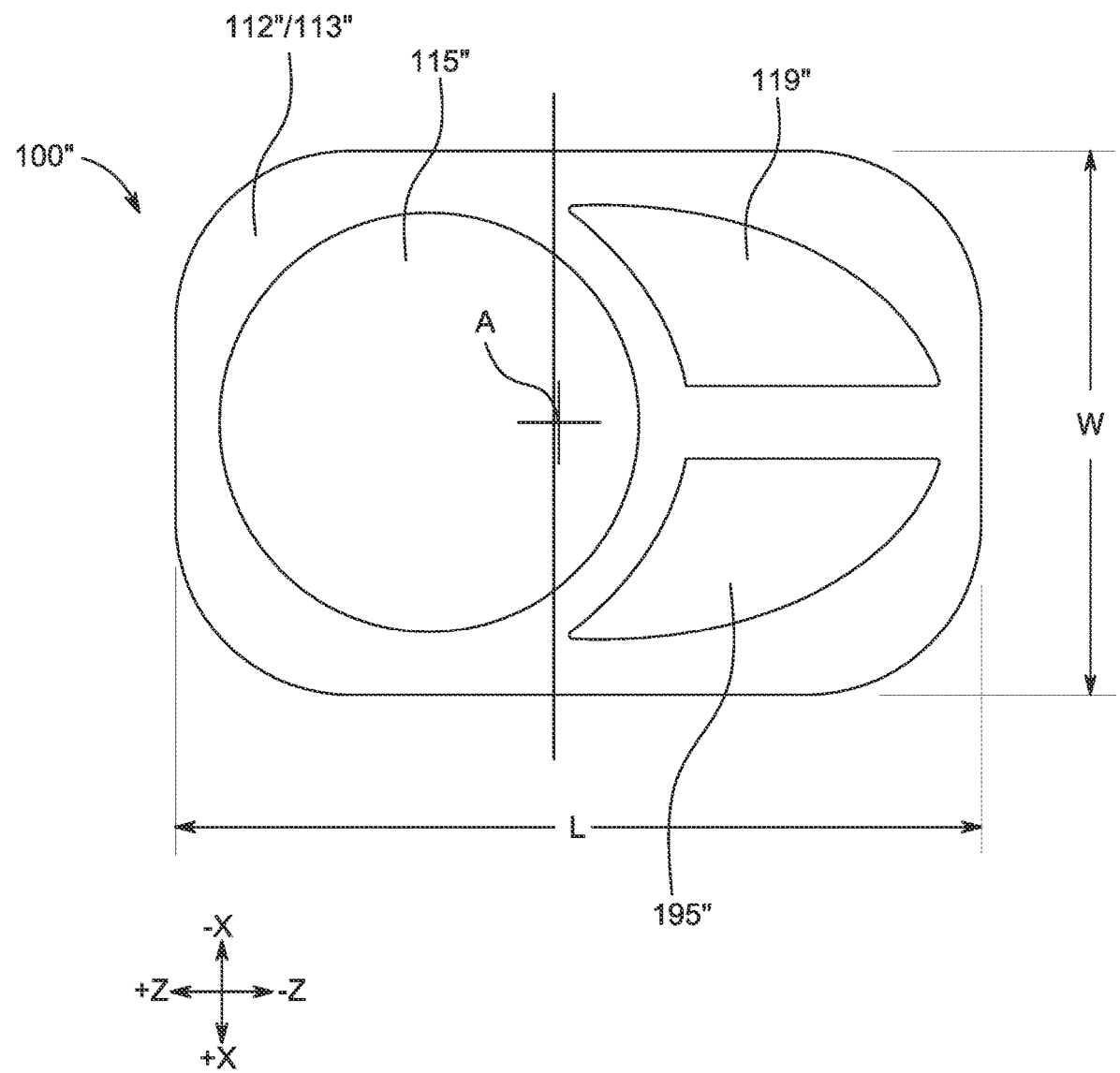
FIG. 11 is a cross-sectional view, similar to FIGS. 3A and 9, of a portion of another pacing intubation assembly, according to some embodiments of the disclosure.

In some embodiments, different passageways of a delivery device assembly may extend parallel and adjacent to one another (e.g., as compared to concentrically with one another, as shown by passageways 115 and 119 of FIGS. 2-4). For example, as shown in FIG. 9, passageways 115', 119', and 195' may be defined by a wall 113' and extend adjacent to one another along a length of a tube 112' of an assembly 100' (e.g., passageway 115' may be used for passing gastric contents, passageway 195' may be used for passing communicative coupling(s) for one or more electrodes 50, and/or passageway 119' may be used as a vent for assistance with gastric decompression, although any other suitable functionalities may be enabled and/or any other suitable number of passageways may be provided). Similarly, as shown in FIG. 11, passageways 115", 119", and 195" may be defined by a wall 113" and extend adjacent to one another along a length of a tube 112" of an assembly 100" (e.g., passageway 115" may be used for passing gastric contents, passageway 195" may be used for passing communicative coupling(s) for one or more electrodes 50, and/or passageway 119" may be used as a vent for assistance with gastric decompression, although any other suitable functionalities may be enabled and/or any other suitable number of passageways may be provided).

Expander subassembly 160 may include any suitable expander component 164 of any suitable number that may provide exterior surface 163 and interior surface 165 extending along any suitable portion or all of the length between first or proximal expander end 161 and second or distal expander end 169. An exemplary expander component 164 may include at least one proximal or first expander opening 162 at or near end 161 and at least one distal or second expander opening 168 at or near end 169. As shown, expander subassembly 160 may be coupled to tube subassembly 110 such that an expander passageway 167 may be provided between interior surface 165 of expander component 164 and along and about exterior surface 118 of tube assembly 110 between ends 161 and 169 of expander component 164. For example, first expander opening 162 may be coupled to and about exterior surface 118 of tube assembly 110 at a first position 103 along the length of tube subassembly 110 using any suitable coupling technique (e.g., adhesive, molding (e.g., blow molding), crimping, etc.) and second expander opening 168 may be coupled to and about exterior surface 118 of tube assembly 110 at a second position 107 along the length of tube subassembly 110 using any suitable coupling technique (e.g., adhesive, molding (e.g., blow molding), crimping, etc.) such that expander passageway 167 may be provided between interior surface 165 of expander component 164 and exterior surface 118 of tube assembly 110 at least partially along the length of expander component 164 between ends 161 and 169. Expander component 164 may be a balloon (e.g., a high volume, low pressure balloon) or any other suitable expander mechanism or component that may be made of any suitable material (e.g., polyurethane, silicone, rubber, polyethylene terephthalate ("PET"), nylon, and/or the like) and/ or that may be at least semi-compliant and that may define a space that may be inflatable by air or any other suitable fluid (e.g., gas or liquid or any other suitable substance that may be able to flow into and/or out of the expander mechanism), such that the space may change shape when pressure therein may change.

Tube wall(s) 113 of subassembly 110 may also provide one or more surfaces 117 of tube subassembly 110 that may define at least one inflation passageway 119 for extending between at least one other proximal or third tube or inflation opening 104 that may provide access to inflation passageway 119 (e.g., fluid communication between inflation passageway 119 and an ambient environment of body structure 112 of subassembly 110) at or near end 101 of assembly 100 and at least one distal or fourth tube or inflation opening 106 that may provide access to passageway 119 (e.g., fluid communication between inflation passageway 119 and an ambient environment of body structure 112 of subassembly 110) at a position along the length of assembly 100 distal of opening 104 (e.g., between positions 103 and 107 along the length of subassembly 110), where opening 106 may be operative to fluidly couple inflation passageway 119 of tube subassembly 110 to expander passageway 167 of expander subassembly 160 (e.g., between positions 103 and 107 along the length of subassembly 110). For example, as shown in FIGS. 3 and 3A-4, inflation passageway 119 may be a single passageway extending concentrically about a longitudinal axis of tube subassembly 110 (e.g., axis A) and/or concentrically about passageway 115, although, in other embodiments, inflation passageway 119 may be provided by one or two or more distinct passageways, each of which may extend along and adjacent passageway 115 but not entirely about passageway 115. In some embodiments, at least one opening 104 may not be provided at end 101 of assembly 100 but may instead be provided along and/or through a side surface of tube wall(s) 113 proximal to end 101. As shown in FIGS. 3 and 3A-4, two or more tube openings 106 may be provided through tube wall(s) 113 of tube subassembly 110 (e.g., between surfaces 117 and 118), each of which may be operative to fluidly couple inflation passageway 119 of tube subassembly 110 to expander passageway 167 of expander subassembly 160 (e.g., a first tube opening 106 may be positioned distally near end 161 of expander subassembly 160 while a second tube opening 106 may be positioned proximately near end 169 of expander subassembly 160), while, in other embodiments, only a single tube opening 106 may be provided for coupling passageways 119 and 167.

Any suitable fluid (e.g., air or a liquid or a combination thereof) may be injected (e.g., by operator O using any suitable fluid delivery system (not shown)) through at least one opening 104, into and through passageway 119, then out of passageway 119 through at least one tube opening 106, and then into expander passageway 167 for at least partially inflating expander component 164 about tube subassembly 110 for reconfiguring expander subassembly 160 from a natural or relaxed or un-inflated state (e.g., when no external forces of assembly 100 are being applied to expander component 164 (e.g., as shown in FIG. 3)) into an unnatural or tensioned or at least partially inflated state (e.g., when the injected fluid within expander passageway 167 applies forces to expander component 164 (e.g., as shown in FIG. 4)), which may reconfigure assembly 100 from an insertion state (e.g., as shown in FIGS. 2 and 3) into an expanded state (e.g., as shown in FIGS. 2A and 4). Any suitable volume of such injected fluid may be retained within the combined space defined by fluidly coupled passageways 119 and 167, for example, by capping opening 104. Passageway 119 may be of a fixed volume when body structure 112 may be any suitable rigidity to prevent a collapse of the shape of passageway 119, while the volume of passageway 167 may change based on the amount of fluid retained within the combined space of fluidly coupled passageways 119 and 167. Additionally or alternatively, any suitable fluid (e.g., air or liquid) may be removed (e.g., by operator O using any suitable fluid removal system (not shown)) from expander passageway 167 through at least one tube opening 106, into and through passageway 119, then out of passageway 119 through at least one opening 104 for at least partially deflating expander component 164 about tube subassembly 110 for reconfiguring expander subassembly 160 from an unnatural or tensioned or at least partially inflated state (e.g., when the fluid within expander passageway 167 to be removed applies forces to expander component 164 (e.g., as shown in FIG. 4)) into a natural or relaxed or un-inflated state (e.g., when no fluid within expander passageway 167 applies force to expander component 164 (e.g., as shown in FIG. 3)), which may reconfigure assembly 100 from an expanded state (e.g., as shown in FIGS. 2A and 4) into a removal state (e.g., as shown in FIGS. 2D and 3). Expander subassembly 160 may be coupled to tube subassembly 110 and configured such that expander subassembly 160 (e.g., expander component 164) may be expanded to an equilibrium geometry of a particular unnatural or tensioned or at least partially inflated state of FIG. 4 when a particular amount (e.g., volume (e.g., a volume of 30 cubic centimeters or 50 cubic centimeters or any other suitable amount)) of fluid is injected into assembly 100 through opening 104 and retained within assembly 100 (e.g., within passageways 119 and 167) but when no external force may be applied to expander subassembly 160 (e.g., by patient 1 (e.g., by constricting walls 13 of patient passageway 15)). Such a particular inflated state of expander subassembly 160 may define a structure of any suitable particular equilibrium geometry. For example, as shown in FIG. 4, the particular equilibrium geometry of a particular inflated state of expander subassembly 160 may include a proximal or first expander component section 166a, an intermediate or second expander component section 166b, and a distal or third expander component section 166c, where first expander component section 166a may extend between position 103 and a section 105 along a length ELA of tube subassembly 110 with a maximum cross-sectional dimension (e.g., diameter) EDA, where second expander component section 166b may extend along section 105 along a length ELB of tube subassembly 110 with a maximum cross-sectional dimension (e.g., diameter) EDB, and where third expander component section 166c may extend between section 105 and position 107 along a length ELC of tube subassembly 110 with a maximum cross-sectional dimension (e.g., diameter) EDC. Expander subassembly 160 may be manufactured and/or coupled to tube subassembly 110 and/or inflated in any suitable manner(s) such that the equilibrium geometry of a particular inflated state of expander subassembly 160 may be operative to retain the portion of patient 1 at opening 91 of target space 95 between first expander component section 166a and third expander component section 166c (e.g., along second expander component section 166b) when assembly 100 is in its expanded state and appropriately positioned within patient 1. In some embodiments, ELA may be about 3-7 centimeters and/or ELC may be about 2-4 centimeters and/or ELB may be about 0.5-5 centimeters. Expander component section 166a may include a tooth-shape and/or a cylindrical shape or disc shaped or any other suitable shape along length ELA (e.g., when expanded), and/or expander component section 166c may be spherical or disc shaped or any other suitable shape along length ELC (e.g., when expanded) to minimize its volume, where EDC may be about 5-7 centimeters while ELC may be about 2-4 centimeters in the equilibrium expanded state of expander assembly 160. In some embodiments, as shown, the geometry of a particular inflated state of one, some, or each expander component section of expander subassembly 160 may be symmetrical or asymmetrical about longitudinal axis A of tube subassembly 110. For example, a maximum cross-sectional dimension (e.g., diameter) EDA1 of first expander component section 166a between a first (e.g., top) side of tube subassembly 110 and expander component 164 may be the same as or different than a maximum cross-sectional dimension (e.g., diameter) EDA2 of first expander component section 166a between a second (e.g., bottom) side of tube subassembly 110 and expander component 164 (e.g., opposite sides with respect to longitudinal axis A), and/or a maximum cross-sectional dimension (e.g., diameter) EDB1 of second expander component section 166b between a first (e.g., top) side of tube subassembly 110 and expander component 164 may be the same as or different than a maximum cross-sectional dimension (e.g., diameter) EDB2 of second expander component section 166b between a second (e.g., bottom) side of tube subassembly 110 and expander component 164 (e.g., opposite sides with respect to longitudinal axis A), and/or a maximum cross-sectional dimension (e.g., diameter) EDC1 of third expander component section 166c between a first (e.g., top) side of tube subassembly 110 and expander component 164 may be the same as or different than a maximum cross-sectional dimension (e.g., diameter) EDC2 of third expander component section 166c between a second (e.g., bottom) side of tube subassembly 110 and expander component 164 (e.g., opposite sides with respect to longitudinal axis A). In some embodiments, second expander component section 166b may be prevented from expanding beyond a particular cross-sectional dimension of its equilibrium geometry due to the structural composition of expander component 164 (e.g., despite at least a portion of first expander component section 166a and/or at least a portion of third expander component section 166c being able to expand beyond a particular cross-sectional dimension of its equilibrium geometry). Alternatively, any suitable mechanism 159, such as a rigid band of material, may be positioned about expander component 164 along at least a portion of second expander component section 166b to prevent second expander component section 166b from expanding beyond maximum cross-sectional dimension (e.g., diameter) EDB of the equilibrium geometry of FIG. 4 while still allowing a portion of expander passageway 167 to extend through second expander component section 166*b* between expander component 164 and surface 118 of tube subassembly 110, where EDB may be about 0.5-1.5 centimeters in the equilibrium expanded state of expander assembly 160. First expander component section 166*a* may have any suitable pressure (e.g., no greater than 40 mmHg for a particular size patient) when in the equilibrium expanded state of expander assembly 160, such as a pressure operative to retain assembly 160 in a desired functional position within patient 1 while also enabling walls 13 of passageway 15 to naturally contract and expand (e.g., to enable patient 1 to safely breath). Therefore, first expander component section 166*a* and third expander component section 166*c* may define distinct portions of expander passageway 167, even when fluidly coupled via a portion of expander passageway 167 defined by second expander component section 166*b*.

In some embodiments, as shown, assembly 100 may also include a supplemental tube passageway 195 that may be defined by at least a portion of one or more walls 113 of tube subassembly 110 that may be provided to treat (e.g., extract material from and/or inject material into) a supplemental region of patient 1 that may be proximal to target 95 and proximal to expander subassembly 160 when assembly 100 is in its expanded state in a functional position within patient 1. For example, as shown, supplemental tube passageway 195 may extend from a proximal end 191 to at least one distal end 199. A proximal opening 192 for passageway 195 may be provided at or near proximal end 191 and a distal opening 198 for passageway 195 may be provided at or near distal end 199. Fluid may be injected into patient 1 (e.g., by operator O) through passageway 195 from opening 192 to opening 198 and/or fluid may be removed from patient 1 (e.g., by operator O) through passageway 195 from opening 198 to opening 192 (e.g., as a suction process). As shown, at least a portion of passageway 195 may be provided adjacent to passageway 119 and/or passageway 115.

Various materials may be used for various elements of an assembly 100, which may vary based on the procedure and/or patient in which assembly 100 is to be used. As just one example, when assembly 100 may be used for a nasogastric intubation procedure, tube subassembly 110 may be made of polyurethane (e.g., a thermoplastic polyurethane elastomer), silicone, polyvinyl chloride, or rubber, or the like and/or may be a molded piece and/or extruded piece or formed in any other suitable manner, expander subassembly 160 may be a molded piece and/or extruded piece and/or may be made of silicone, polyurethane, rubber, thermoplastic elastomers, or the like and/or may be coupled to tube subassembly 110 via any suitable type of mechanism or crimp or bond or adhesive (e.g., cyanoacrylate or silicone glue). One or more of any or all portions of expander subassembly 160 and tube subassembly 110, and/or the like of assembly 100 may be provided with an alkaline coating on one or both of its interior and exterior walls, such that when material (e.g., food or acidic stomach contents) travels through such components, the acidity of the material may get neutralized. Additionally or alternatively, one or more of any or all portions of expander subassembly 160 and tube subassembly 110, and/or the like of assembly 100 may be at least partially X-ray visible such that an operator may ensure that it is properly placed within patient 1 for a particular procedure.

Assembly 100 may be used to treat a patient in any suitable manner. In some embodiments, while expander subassembly 160 may be in a natural or relaxed or uninflated state (e.g., while the geometry of expander 164 may be similar to the geometry of surface 118 of structure 112), distal end 109 of assembly 100 may be initially inserted into patient 1 and fed into passageway 15 or further through passageway 15, through openings 19/91, and into target space 95. The length of assembly 100 necessary to enable distal end 109 to be positioned within space 95 or passageway 15 when preferred, while proximal end 101 may be accessible to an operator may vary based on the size of patient 1. When a particular length (e.g., 65 centimeters) of assembly 100 has been inserted (e.g., in the direction of arrow I) for a given patient such that an operator may believe distal end 109 is within or close to space 95, or at any other suitable moment, the operator may attempt to determine the location of expander 164 with respect to space 95. In some embodiments, an initial volume of fluid may be injected into passageway 167 via passageway 119 for expanding a portion of passageway 167 to better differentiate the geometry of at least a portion of expander 164 from the geometry of structure 112, and then any suitable technique may be used to detect the location of expander 164 within patient 1. For example, one or more of any or all portions of expander subassembly 160 or tube subassembly 110 may be at least partially X-ray visible (e.g., using a Barium marker dye on a portion of expander 164) such that an operator may ensure that it is properly placed within patient 1 for a particular procedure. This technique may be used even when expander subassembly 160 may be in a natural or relaxed or un-inflated state. The operator may detect the location of expander 164 and further insert assembly 100 into patient 1 until expander 164 is at least partially positioned within space 95 or another suitable target. In some embodiments, the operator may position the entirety of expander 164 within space 95.

Any suitable internal electrode(s) 50 may be incorporated into and/or otherwise provided by or coupled to delivery device assembly 100 for enabling the insertion of the electrode(s) into patient 1 and functional positioning of the electrode(s) within patient 1. For example, as shown a first internal electrode 50*a* may be incorporated into or coupled to a portion (e.g., interior, exterior, or middle portion) of wall(s) 113 of tube subassembly 110 distally beyond expander 164 (e.g., mounted to an external surface of wall 113 (e.g., as a ring shape or at least partial circumferential ring or twisted shape), mounted within wall 113 (e.g., as a ring shape or at least partial circumferential ring or twisted shape (see, e.g., an electrode 50*a*')), etc.) and/or a second internal electrode 50*b* may be incorporated into or coupled to a portion (e.g., interior, exterior, or middle portion) of expander 164 (e.g., as a ring shape or at least partial circumferential ring or twisted shape or coil shape) and/or a third internal electrode 50*c* may be incorporated into or coupled to a portion (e.g., interior, exterior, or middle portion) of wall(s) 113 of tube subassembly 110 proximally before expander 164 (e.g., mounted to an external surface of wall 113 (e.g., as a ring shape or at least partial circumferential ring or twisted shape), mounted within wall 113 (e.g., as a ring shape or at least partial circumferential ring or twisted shape), etc.). For example, a wire (e.g., any suitable bus similar to bus 38) or any other suitable communicative coupling may be at least partially embedded within a tube wall of delivery device 100 (e.g., tube wall 113 and/or through passageway 195 and/or passageway 119 and/or passageway 115) and may then exit to an external surface of the delivery device at a level of internal electrode 50 for communicatively coupling electrode 50 and device 30 (see, e.g., communicative coupler 51*c* that may extend through passageway 195 (e.g., from pacing device 30) to electrode 50*c* (e.g., for communicating signal(s) 40), although any other suitable communicative coupler(s) may be provided through any suitable passageway(s) for extending through assembly 100 along at least a portion of subassembly 110 between any suitable electrode 50 and out from a proximal portion of assembly 100 for coupling with any suitable pacing device). Such an exposed medium (e.g., metal) may then sit on top of (e.g., at an external portion of) a tube or expander of the delivery device. This may be provided as any suitable design (e.g., a coil (e.g., a simple coil design)) that may be configured to anchor on an end of the electrode portion. For example, a coil shape may allow it to expand and contract about the tube (e.g., a cross-sectional area of the electrode extending about the tube (e.g., about a cross-sectional periphery of the tube (see, e.g., FIG. 9)) may be configured to expand and contract about the tube and/or along a length of the tube) with an expander (e.g., balloon), but a more complex interlocking design may also be used for such a purpose (e.g., a coil electrode (see, e.g., FIG. 14), a braid electrode (see, e.g., FIG. 13), a spiral cut tubular electrode (see, e.g., FIG. 15), and/or the like may be positioned about any suitable expander and/or about any suitable portion of a tubular assembly that may bend or flex. When an internal electrode is positioned in, on, or about an expander (e.g., expander 164) or is an integral part of an expander, expansion of such an expander within a patient may help to ensure substantial or maximal contact of the electrode or adjacent tube structure with the esophageal mucosa or other useful portion(s) of the patient during use. An electrode may be coupled (e.g., at one or both ends or along a significant portion or the entirety of its length) to a flexible tube wall or expander using any suitable technique(s) in any suitable manner, including, but not limited to, glue, solder, mechanical compression (e.g., swaging), reflowing of material of assembly 100 (e.g., reflowing (e.g., heating or melting) polyurethane or other material of tube wall 113 or applying more of such material over a portion of the electrode, anchoring an electrode portion (e.g., an end) with an electrode band (see, e.g., FIG. 13 and/or FIG. 14), such as a band that may freely slide with respect to a tube during expander reconfiguration, and/or the like.

Figure 7:
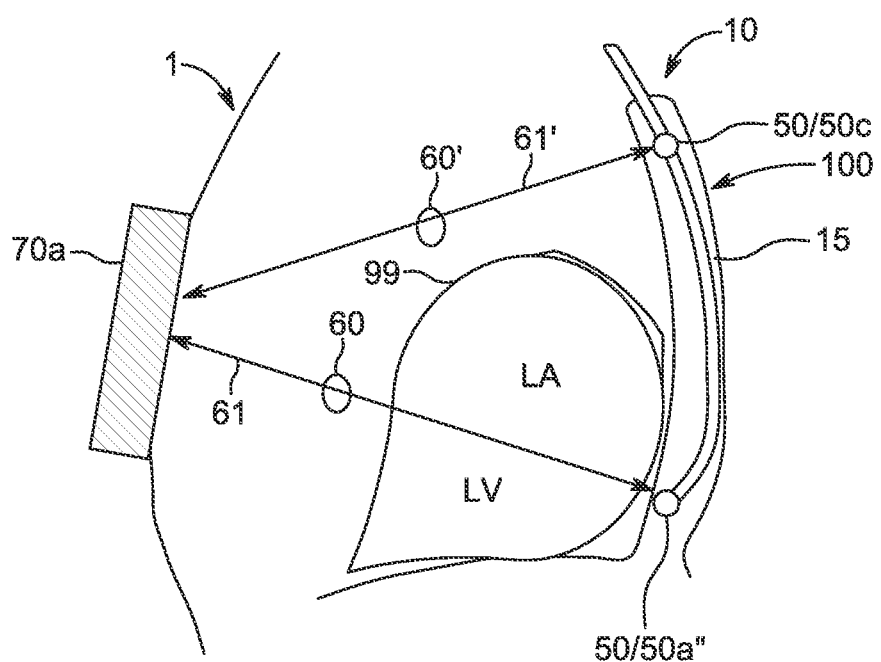
FIG. 7 is another cross-sectional view of the patient with the pacing intubation assembly in another functional state, according to some embodiments of the disclosure.
Figure 8:
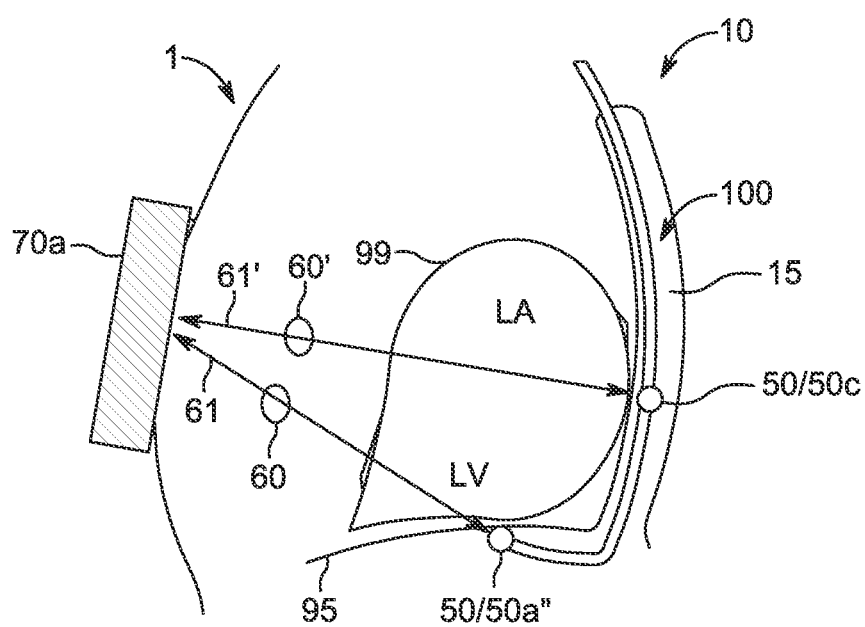
FIG. 8 is another cross-sectional view of the patient with the pacing intubation assembly in another functional state, according to some embodiments of the disclosure.

As shown in FIGS. 5-8, heart 99 of patient 1 can be induced to beat by passing electrical current (e.g., signal(s) 60) through heart muscle 99 of patient 1 (e.g., from electrode(s) 50 to electrode(s) 70). For example, a useful electrical pulse (e.g., signal(s) 40) may be initiated by pacing device 30 and communicated to one or more electrodes 50 (e.g., via any suitable signal coupling component(s) 51, such as one or more wires that may be at least partially embedded in any suitable wall(s) or other portion(s) of delivery device assembly 100). Electrode(s) 50 may be positioned by delivery device assembly 100 to be in contact with or at least adjacent the lining of the esophagus or trachea or any other suitable passageway 15 (e.g., through inflation of expander 164 and/or through other positioning and/or reconfiguring of assembly 100). The electrical pulse 40 may be conducted as a pulse 60 via one or more internal electrode(s) 50 and through the esophagus (e.g., passageway wall 13 of passageway 15 of patient 1 (e.g., when one or more electrode(s) 50 are positioned therein (see, e.g., FIG. 7 (e.g., with each one of electrodes 50a" and 50c as an esothoracic pacing electrode)))) and/or stomach (e.g., wall 93 of target 95 (e.g., when at least one electrode 50 is positioned therein (see, e.g., FIG. 8 (e.g., electrode 50a" may be positioned as a gastrothoracic pacing electrode while electrode 50c may be positioned as an esothoracic pacing electrode)))) as well as cardiac muscle 99 (e.g., heart (e.g., left atrium ("LA") and/or left ventricle ("LV"), etc.)) of patient 1, anteriorly toward any suitable external electrode(s) 70 (e.g., an adhesive chest pad external electrode 70a) that may be placed on the front of the patient's chest (e.g., exterior chest wall 3 of patient 1) overlying the heart. This may induce "capture," which may trigger a coordinated squeeze of the heart. For example, as shown in FIG. 7, assembly 100 may be positioned within patient 1 such that electrode 50" may be positioned lower down within passageway 15 whereby pulse 60 may be conducted from electrode 50" towards electrode 70a along a path 61 via heart 99 (e.g., to induce capture), and such that electrode 50c may be positioned higher up within passageway 15 whereby pulse 60' may be conducted from electrode 50c towards electrode 70a along a path 61' that is not via heart 99 (e.g., so as not to induce capture), whereby pulse 60' may be the same as pulse 60 when electrode 50c and electrode 50a" are coupled in parallel for receiving the same signal 40 from coupler 51 (see, e.g., electrodes 50d-50d"" of FIG. 12). However, as shown in FIG. 8, assembly 100 may be positioned further down within patient 1 such that electrode 50" may be positioned within target 95 whereby pulse 60 may be conducted from electrode 50" towards electrode 70a along a new path 61 that is still via heart 99 (e.g., to induce capture), and such that electrode 50c may be positioned lower down within passageway 15 whereby pulse 60' may be conducted from electrode 50c towards electrode 70a along a new path 61' that is now via heart 99 (e.g., so as to induce capture), whereby pulse 60' may be the same as pulse 60 when electrode 50c and electrode 50a" are coupled in parallel for receiving the same signal 40 from coupler 51 (see, e.g., electrodes 50d-50d" of FIG. 12). Positioning an electrode 50 in the stomach may enable electrical capture by the heart (e.g., of signal(s) 60) at lower currents. However, given the variable size and shape of the stomach compared to the narrower esophagus, positioning an electrode in the stomach is often more difficult and provides less opportunity for more reliable contact with and capture of patient tissue with an electrode in the stomach as compared to the esophagus. As such, an electrode array with at least one electrode based in the esophagus may be preferred in some situations as it may enable a more consistent positioning of electrode (s) relative to the heart (e.g., in practice, an electrode in a stomach can get under the heart but can't reliably stay in that position as the stomach is a bigger variable space, so it may be harder to anchor an electrode to a tissue wall of the stomach, although suctioning technique may be useful (see, e.g., FIG. 21)). An electrode 70 may be positioned in any suitable position along an exterior of the patient (e.g., using adhesive), such as chest 3 with one or more electrodes 70a, back 7 with one or more electrodes 70b, and/or the like. However, an electrode 70b on back 7 may not be useful for many applications with electrode(s) 50 of apparatus 100, as this would direct current from the esophagus backward away from the heart and would not yield desirable pacing/cardiac stimulation results.

Various features may be provided for enabling the functional and efficient use of system 10. For example, any suitable hydrophilic coating may be incorporated into delivery device assembly 100 (e.g., along exterior surface(s) of tube or body structure 112 and/or expander 164 and/or any electrode(s) 50 and/or the like) to allow for easier passage thereof through the nose, mouth, pharynx, esophagus, and/or the like of the patient, including, but not limited to, polyvinylpyrrolidone ("PVP"), polyurethanes, polyacrylic acid ("PAA"), polyethylene oxide ("PEO"), polysaccharide materials, and/or the like, which may be applied to the entire length of the tube or any suitable portion(s) thereof. Body structure 112 of tube subassembly 110 may be made of polyurethane, silicone, and/or any other suitable material(s) that may be configured to retain an appropriate flexibility and stiffness to function as a nasogastric and/or orogastric tube for allowing it to travel through the pharynx and enter the stomach or any other suitable end target. Body structure 112 may be made at least partially of electrically insulative material (e.g., a plastic), such that any communicative coupler(s) (e.g., coupler 51c) and/or electrode(s) (e.g., electrodes 50a, 50b, 50c, etc.) may be insulated from one another (e.g., where desired). Graduated markings (e.g., see, e.g., markings 112m of FIG. 21) may be provided along any suitable portion(s) of the length of delivery device assembly 100 that may allow for titration of catheter depth, to ensure optimal positioning thereof for intubation and/or pulsing. A radio-opaque lining may be provided that may make visualization easy on bedside X-ray films (e.g., any suitable X-ray attenuating material may be attached to any suitable surface(s) or impregnated in any suitable surface(s) of any suitable wall(s) of any suitable tube(s) or other suitable component(s) of the delivery device such that such portion(s) of the device may be clearly seen on X-ray (e.g., a distal end of the tube to determine when it may be residing within the patient's stomach or any other suitable target)) and/or a radio-opaque marking may be provided at or near any internal electrode(s) 50 to allow for adjustment of electrode placement after X-ray films (e.g., the electrode may be metal and may be easily seen on X-ray with or without such marking). An external electrode 70 may be provided as a purpose built and sized chest pad electrode that may work in conjunction with an internal (e.g., esophageal) catheter electrode. An external electrode (e.g., chest electrode) may be designed with a specific necessary impedance to ensure optimal capture while not over stimulating chest muscles. The size and shape of an external electrode (e.g., chest electrode) may be optimized to ensure the most efficient way to provide electrical capture and transmission of electrical current. In some embodiments, system 10 may be configured such that it may be integrated with a 3, 6, 12 or other suitable number lead EKG system to enable the ability to provide "on demand" pacing. For example, the electrodes may be configured to have both the ability to administer current for pacing, defibrillation, cardioversion, and/or the like while also serving as electrodes that can sense the native electrical activity of the heart. This may allow the system to detect the patient's natural heartbeat and provide pacing impulses when the native heart rate drops below a rate desired by the user and/or when any other event of interest occurs. A defibrillation coil may be integrated into any internal electrode(s) 50 to allow for cardioversion or defibrillation. While an additional coil may be added, in other embodiments, an electrode may be designed in a way such that it may administer pacing currents as well as cardioversion and defibrillation currents (e.g., for ventricular fibrillation, supraventricular tachycardia ("SVT"), ventricular tachycardia, atrial fibrillation, and/or the like). A channel in a catheter wall and proximal port may be provided to allow the infiltration of any suitable conductive gel that may be moved out from apertures of such a channel (e.g., distal opening 198 of supplemental tube passageway 195) at the level of the internal electrode (e.g., electrode 50c) to improve conduction of electrical impulses (e.g., system 10 may be configured with the ability to provide topical anesthetic through a channel in the catheter and administer topical anesthetic at the level of the internal electrode (e.g., via distal opening 198 of supplemental tube passageway 195)). A unique electrode shape of internal electrode 50 may be utilized that may be flexible and that may allow for comfortable passage through the nose or other opening 11 of the patient. A coil or braid shape of an electrode can be purpose designed so that it may not be rigid (or too rigid) and/or so that it may be able to make any suitable turn as the tube or other suitable delivery device component(s) of assembly 100 may pass from the nose down into the esophagus or via and into any other suitable patient areas. In some embodiments, system 10 may be configured with the capability to provide overdrive pacing through a pulse modulator (e.g., of device 30). For example, the system may be configured to pace the heart at high rates in order to overcome an atrial dysrhythmia.

As mentioned, a center or other portion of tube subassembly 110 of delivery assembly 100 may provide a catheter or tube or body structure 112 that may be hollow or otherwise include a passageway 115 therethrough, where body structure 112 may include one or more distal fenestrations or openings 108 at or near a distal end 109 as well as one or more proximal fenestrations or openings 102 at or near proximal end 101 to enable gastric decompression or any other suitable procedure(s) in a patient. While assembly 100 may be shown in FIGS. 3 and 3A-4 to include three channels along and within portion(s) thereof (i.e., passageway 115 (e.g., for intubation) and passageway 119 (e.g., for inflation/deflation of an expander passageway 167) and passageway 195 (e.g., for material injection/extraction)), it is to be understood that assembly 100 may be provided with any suitable number of passageways or channels for any suitable uses, including, but not limited to, a central large lumen to allow for the removal of gastric contents or the insertion of material (e.g., medication, free water, tube feeds, etc.), a second channel to act as a vacuum line to ensure more compliant decompression of the stomach when continuous suction is applied to the apparatus, a third lumen that may protect and/or guide one or more electrical wires or other suitable communicative couplings (e.g., for conducting signal(s) 40 between pacing device 30 and one or more electrodes 50 coupled to assembly 100), one or more additional lumens that may be integrated to accommodate the capability of introducing electroconductive gel or medication or other suitable material(s) to the outer surface of the tube at the level (e.g., portion of length of tube at which one or more electrodes may be coupled or otherwise provided), and/or the like.

Electrode 50 may be made of any suitable materials, including, but not limited to, stainless steel, copper, and/or other materials that may be configured to conduct electric material while maintaining optimal biocompatibility. An exterior surface of electrode 50 may be smooth or textured to ensure better electrical contact within patient 1 (e.g., when a portion of the electrode may be exposed to the patient (e.g., an exterior surface of electrode 50a or electrode 50b or electrode 50c (e.g., not electrode 50a' that may be contained within body structure 112))). Electrode 50 may be configured such that it may not hinder the flexibility of body structure 112, which may help ensuring its function and use (e.g., as a gastric decompression device). For example, an electrode 50 that may be coupled to and delivered within a patient by assembly 100 may include any suitable configuration, including, but not limited to, a series of discrete metal bands, a braid of metal wire, a coil of wire, and/or the like.

Figure 10:
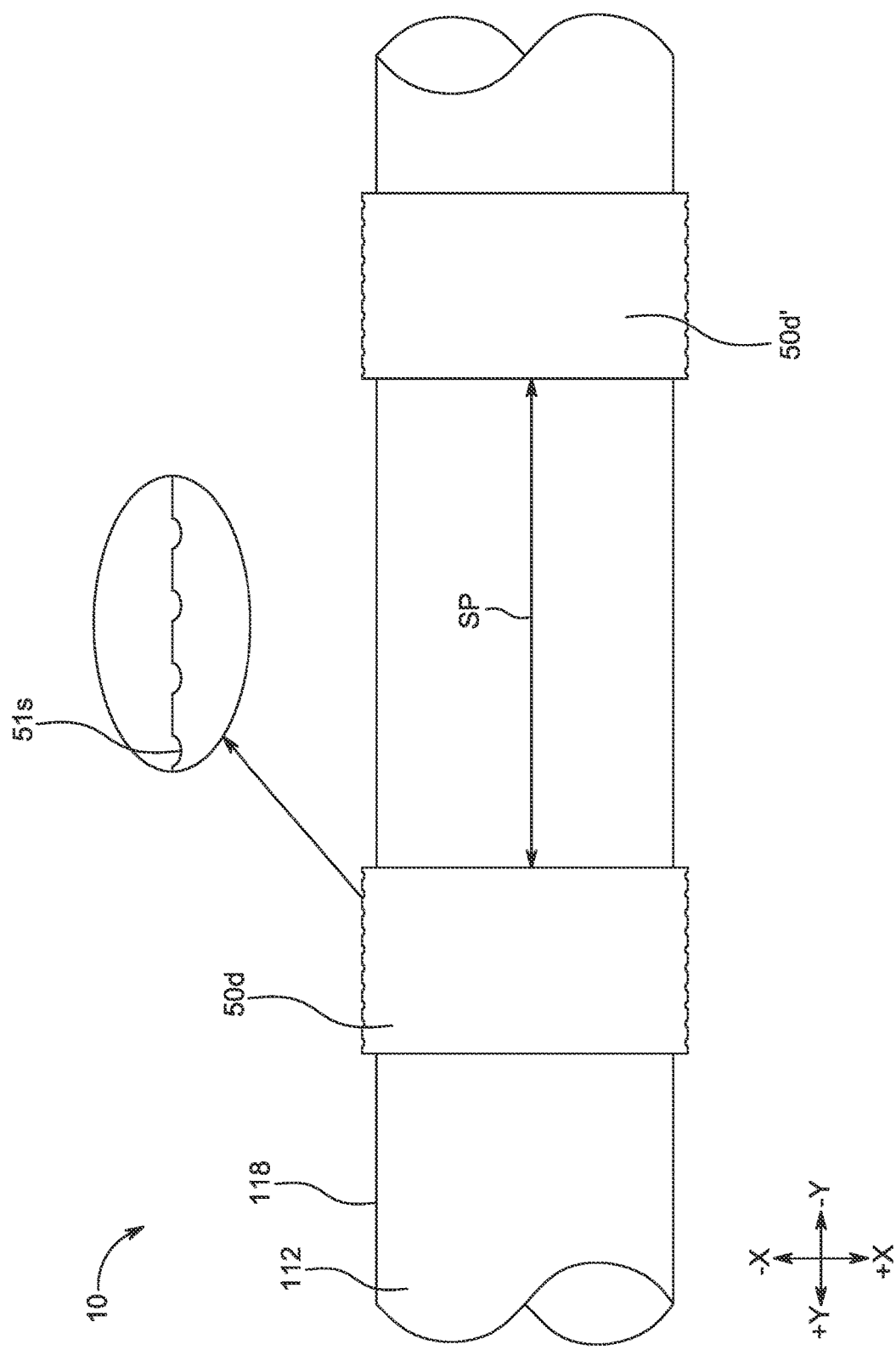
FIG. 10 is a side elevational view of a portion of another pacing intubation assembly, according to some embodiments of the disclosure.
Figure 12:
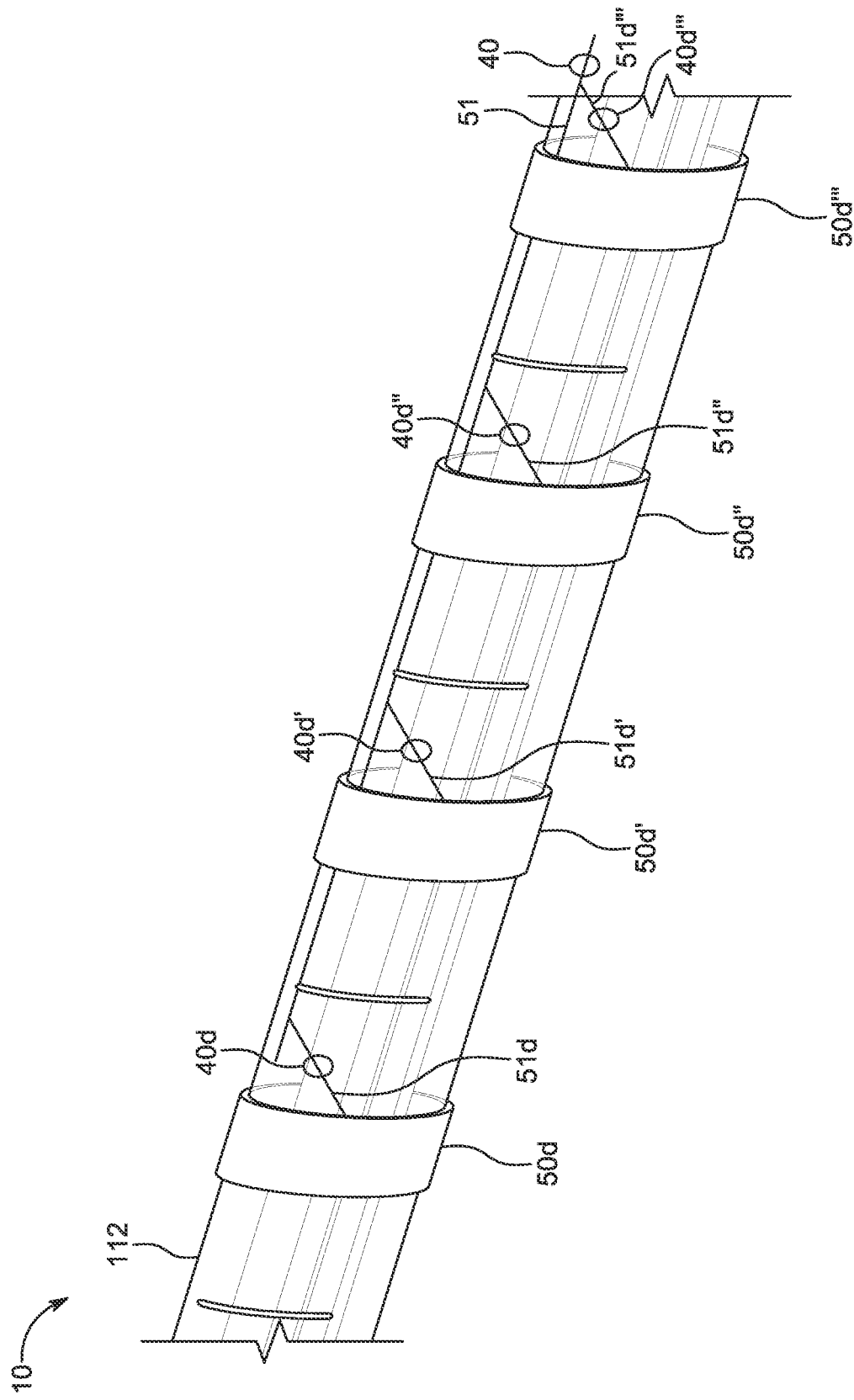
FIG. 12 is a perspective view of a portion of a pacing intubation assembly, according to some embodiments of the disclosure.

In some embodiments, an electrode 50 may be a conductive (e.g., metal (e.g., stainless steel)) band that may extend about an entirety or a significant portion of a cross-sectional periphery of body structure 112 of assembly 100 (see, e.g., electrode 50a, electrode 50a'', and electrode 50c of FIGS. 3 and 3A-4 and electrodes 50d-50d''' of FIGS. 10 and 12) or about an entirety or a significant portion of a cross-sectional periphery of expander 164 of assembly 100 (see, e.g., electrode 50*b* of FIGS. 3 and 3A-4). As shown, electrode 50*a* may be at least partially embedded into an exterior surface 118 of wall 113 of structure 112, while electrode 50*a*' may be embedded within wall 113, while electrode 50*a*" and one, some, or each of electrodes 50*d*-50*d*''' may be positioned about and coupled to exterior surface 118 of wall 113. In some embodiments, two or more electrodes 50 may be provided as discrete bands that may be spaced far enough apart from each other along the length of tube structure 112 to ensure flexibility of tube structure 112 despite the potentially more rigid bands (e.g., by at least a spacing distance SP between electrodes 50*d* and 50*d*'). The number of such electrodes may be any suitable number, such as 2, 3, 4, 5, 6, 7, or more bands. As shown in FIG. 12, any two or more internal electrodes (e.g., each one of electrodes 50*d*-50*d*''') provided by a delivery assembly 100 may be electrically coupled in parallel to a coupler 51 such that the same signal 40 may be communicated by coupler 51 between pacing device 30 and each of the internal electrodes electrically coupled in parallel. Particularly, as shown in FIG. 12, a first parallel coupler branch 51*d* of coupler 51 may electrically couple coupler 51 to electrode 50*d* such that signal 40*d* may be communicated along branch 51*d* to electrode 50*d*, a second parallel coupler branch 51*d*' of coupler 51 may electrically couple coupler 51 to electrode 50*d*' such that signal 40*d*' may be communicated along branch 51*d*' to electrode 50*d*', a third parallel coupler branch 51*d*" of coupler 51 may electrically couple coupler 51 to electrode 50*d*" such that signal 40*d*" may be communicated along branch 51*d*" to electrode 50*d*", and a fourth parallel coupler branch 51*d*''' of coupler 51 may electrically couple coupler 51 to electrode 50*d*''' such that signal 40*d*''' may be communicated along branch 51*d*''' to electrode 50*d*''', where signals 40, 40*d*, 40*d*', 40*d*", and 40*d*''' may be the same signal when communicated along coupler 51 from pacing device 30 to electrodes 40*d*-40*d*'''. Parallel coupler branches may extend from a single coupler 51 at any suitable length(s) along coupler 51 (e.g., from a portion or portions of coupler 51 at or near the electrodes, at or near proximate end 101 of assembly 100, or even at or near a proximate end of coupler 51 (e.g., at or near a coupler connector 56*a*)). Any two distinct electrodes of the disclosure may be electrically coupled in parallel (e.g., a first braid electrode 50*e* and a second coil electrode 50*f* may be electrically coupled in parallel, a first expander electrode 50*b* and a second spiral cut electrode 50*g* may be electrically coupled in parallel, etc.).

Each individual electrode may be configured to have one or more beveled and/or rounded edges (see, e.g., rounded edges of electrode 50*d*' of FIG. 10) to ensure non-traumatic passage of assembly 100 through any suitable passageway 15 of patient 1 (e.g., the nasal or oral pharynx and/or esophagus). Such band electrodes may be of varying thickness, in order to maintain a slim profile but also ensure good contact with any suitable internal wall of patient 1 (e.g., esophageal wall 13). Any electrode 50 may include one or more exterior portions with textured elements (e.g., serrations, undulations, non-flat surface shapes, etc.) that may promote friction or retention of contact between the electrode and an interior wall of the patient (e.g., wall 13, wall 93, etc.). For example, as shown in FIG. 10, an exterior surface of electrode 50*d* may include any suitable serrations or undulations or non-flat surface shapes or other features 51*s* (e.g., along the length of the tube (as shown) and/or about a cross-sectional periphery of the tube), which may be configured to increase the contact surface area of the electrode with the tissue of the patient (e.g., with tissue of patient wall 13 and/or wall 93) and/or help the catheter anchor well and "bite" into the patient tissue, without any significantly sharp edges that may irritate a patient's tissue. Feature(s) 51*s* may include a groove or undulation or soft serration(s) in any suitable exterior wall(s) of any suitable electrode(s) 50 and/or any suitable roughened texture on a smaller/micro level (e.g., non-smooth but not overly coarse), so as to balance amount of bite with any irritation that may be caused to the patient tissue. By using shallow and smooth channels 51*s* along an exposed surface of an internal electrode 50, this effect may be achieved. For example, a spiral type milling may be made along an exposed surface of an electrode to create the grooves. The grooves may be shallow enough so that they do not traumatize the patient tissue but may increase the total surface area of the exposed electrode that may be operative to come in contact with the soft/compliant esophageal mucosa or other suitable patient tissue.

In some embodiments, a cross-section of a catheter tube of assembly 100 may be any suitable shape other than circular (e.g., circular, as may be shown in FIGS. 2, 3A, and 3B). Instead, a cross-section of at least a portion or the entirety of a catheter tube of assembly 100 may be elliptical (see, e.g., assembly 100' of FIG. 9, where its cross-sectional length L may be greater than its cross-sectional width W), rectangular (e.g., with curved corners (see, e.g., assembly 100" of FIG. 11, where its cross-sectional length L may be greater than its cross-sectional width W)), and/or the like. Such non-round or non-circular cross-sectional portions of tube structures of delivery device assemblies may augment the way in which the tube structures may lie within a patient (e.g., within passageway 15 and/or target 95) and may increase contact areas of the assemblies with respect to patient tissue. In such embodiments, a band electrode may be disposed about such a cross-section and may be similarly shaped (e.g., elliptical electrode 50' of FIG. 9, rectangular with curved corners electrode of FIG. 11 (not shown)).

Figure 16:
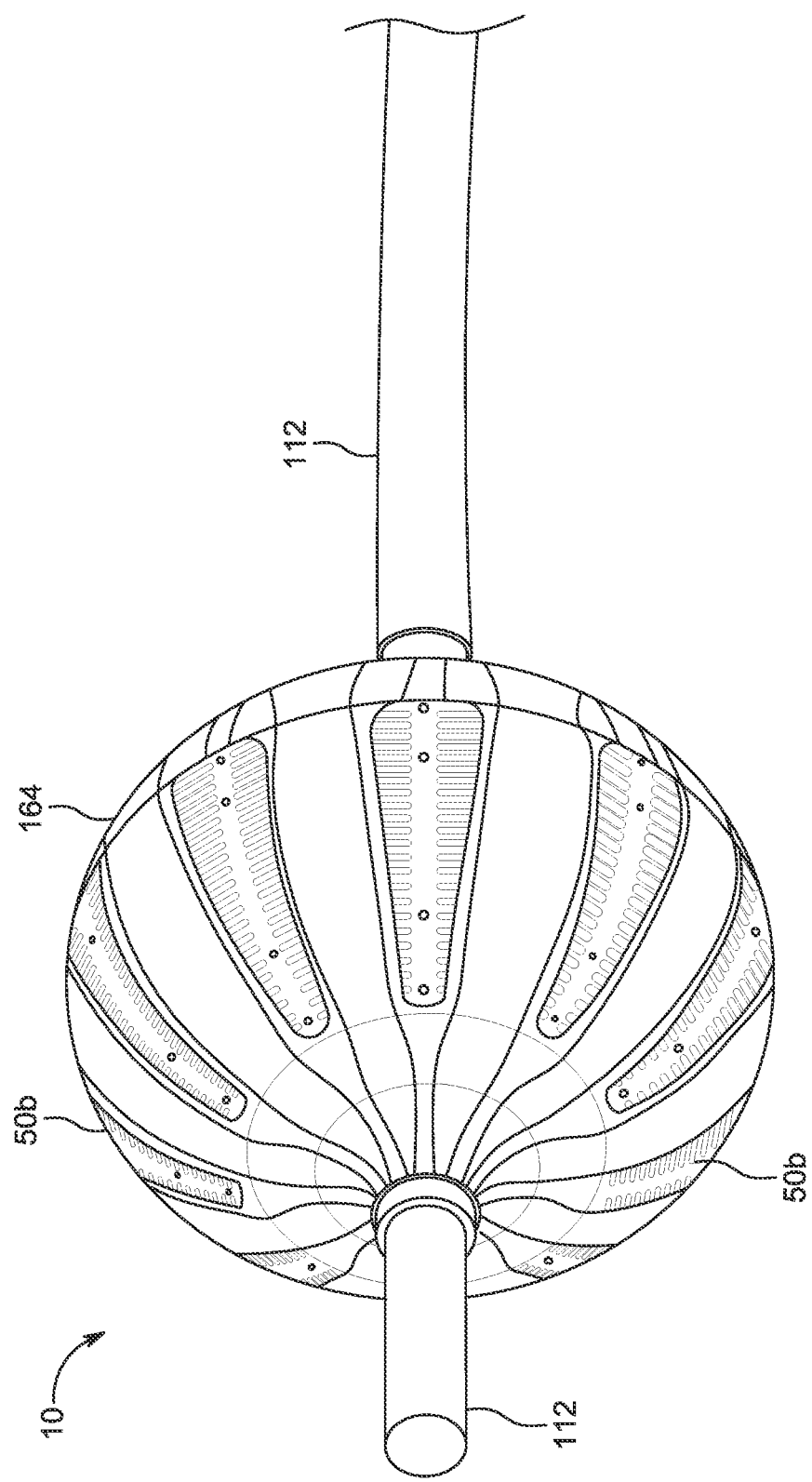
FIG. 16 is a perspective view of a portion of a pacing intubation assembly, according to some embodiments of the disclosure.
Figure 17:
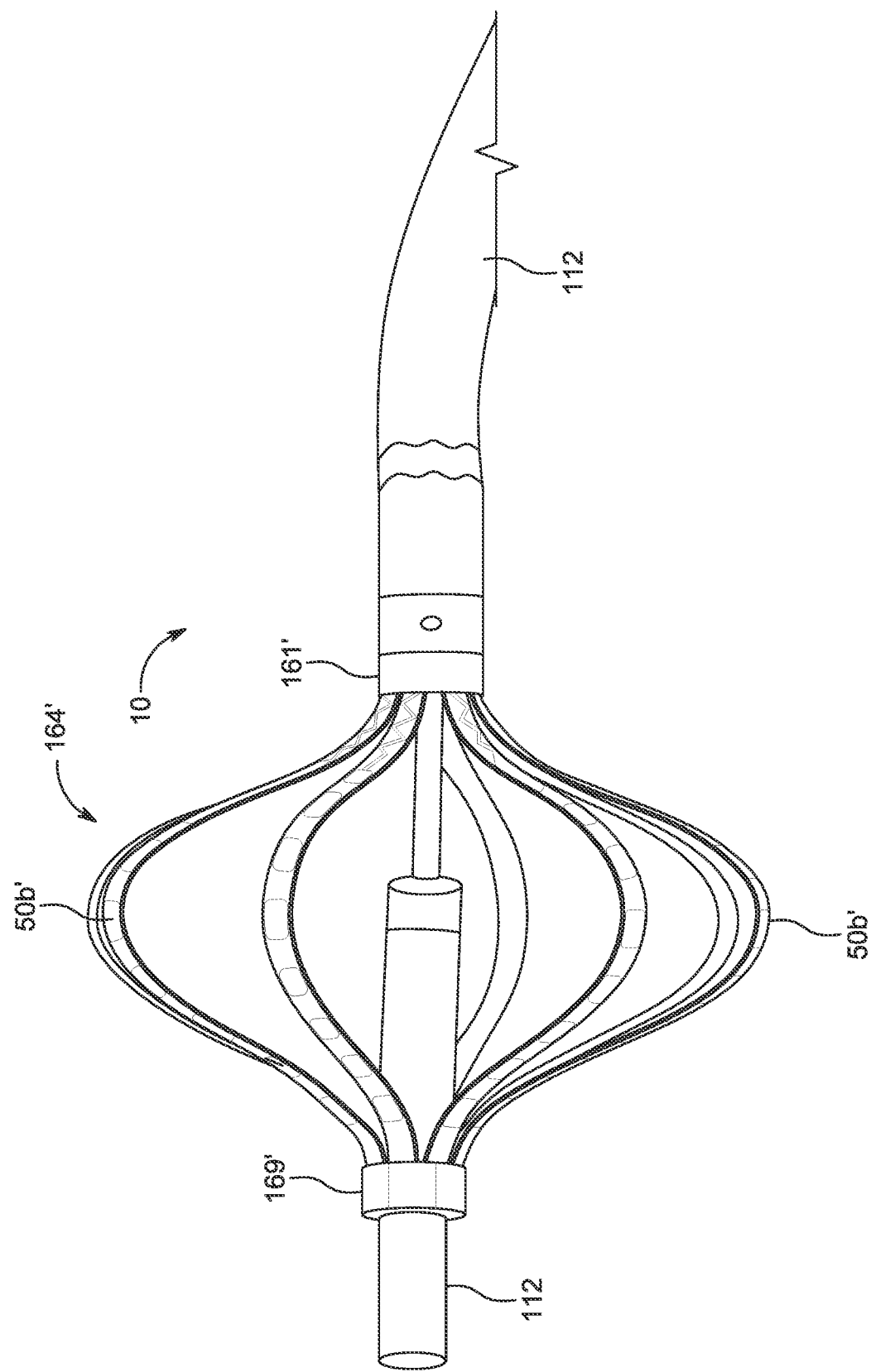
FIG. 17 is a side elevational view of a portion of a pacing intubation assembly, according to some embodiments of the disclosure.
Figure 18:
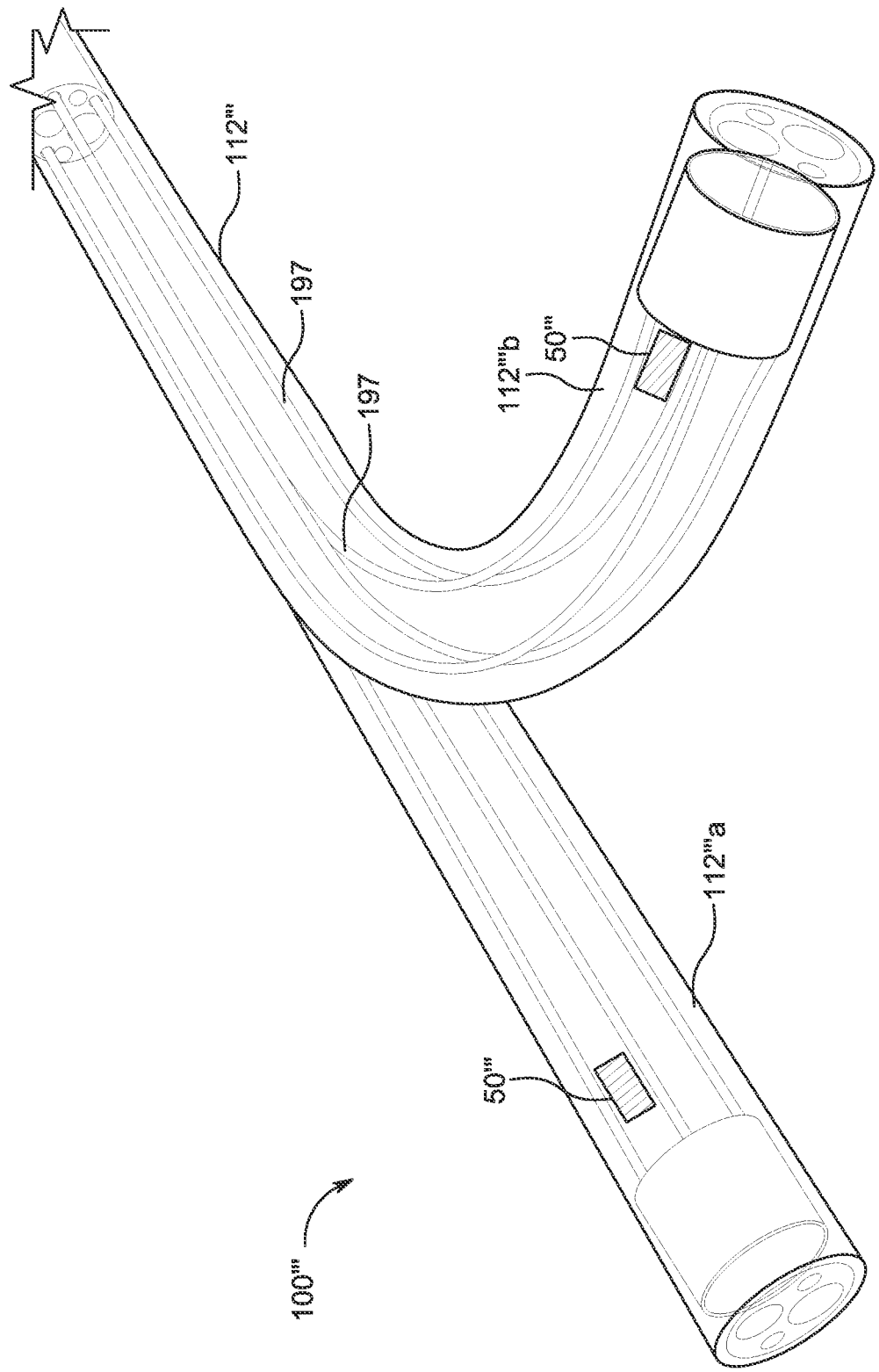
FIG. 18 is a perspective view of a portion of a pacing intubation assembly in different configurations, according to some embodiments of the disclosure.
Figure 19:
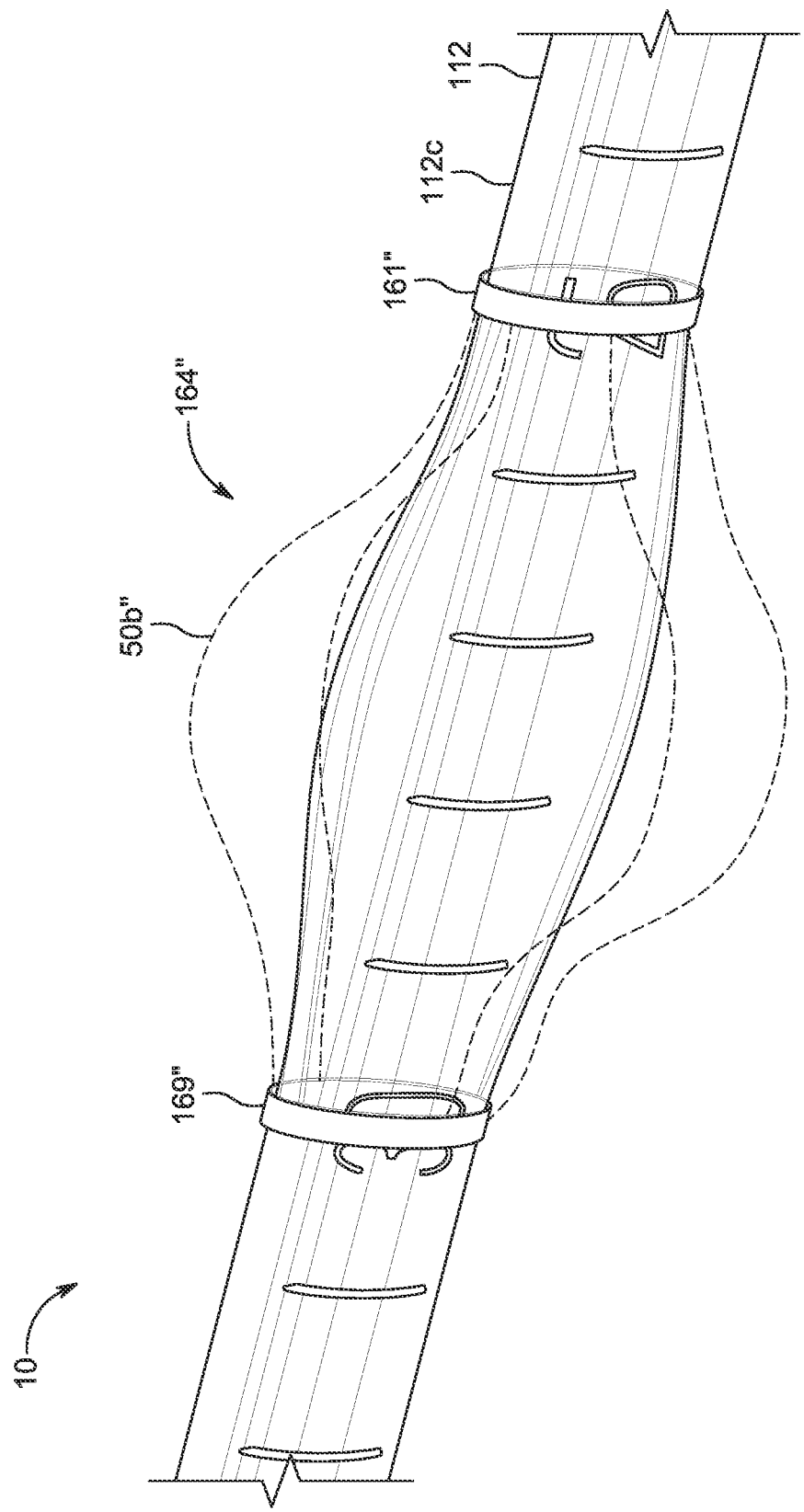
FIG. 19 is a perspective view of a portion of a pacing intubation assembly, according to some embodiments of the disclosure.
Figure 20:
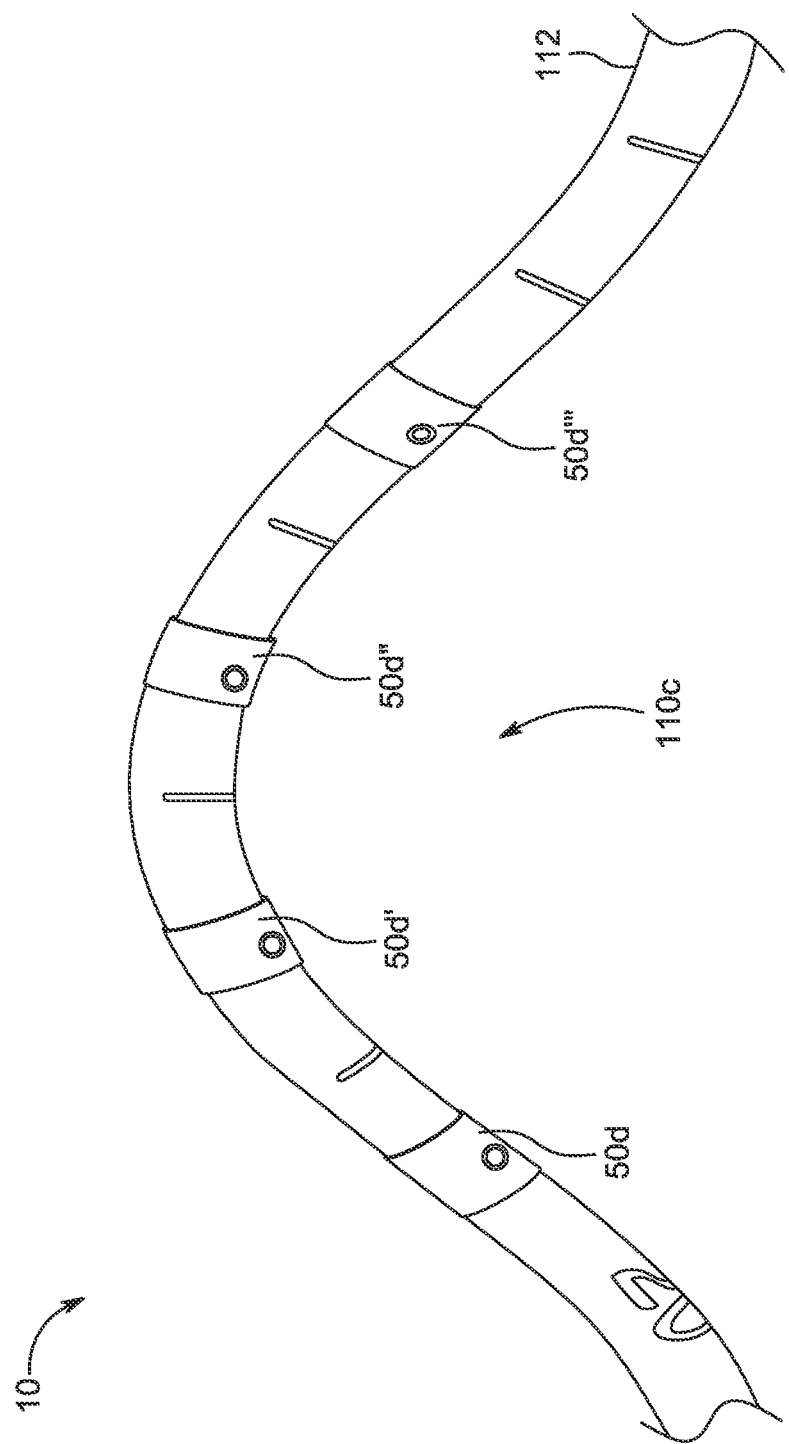
FIG. 20 is a perspective view of a portion of a pacing intubation assembly, according to some embodiments of the disclosure.
Figure 21:
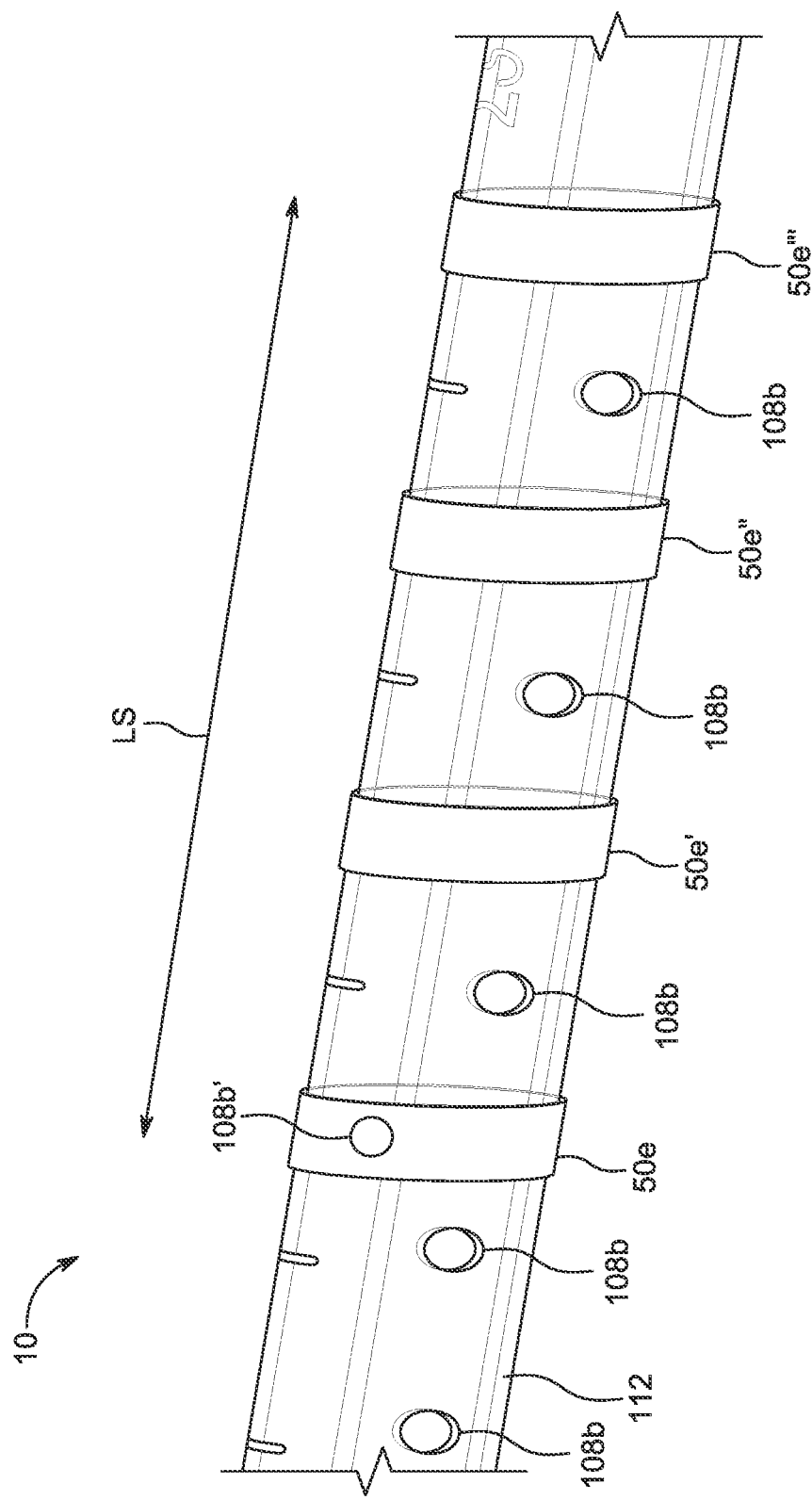
FIG. 21 is a perspective view of a portion of a pacing intubation assembly, according to some embodiments of the disclosure.

Features to augment or enhance contact between a patient's internal tissue (e.g., esophageal wall) and a delivery device assembly and/or its coupled internal electrode(s) may include, but are not limited to, an induced curve of a tube of the assembly at the level of an electrode (see, e.g., assembly 100 with an induced curve 110*c* between electrodes 50*d* and 50*d*''' of FIG. 20, which may be less acute than shown, and which may be induced through any suitable mechanism(s) (e.g., heat set and reconfigurable elements, cables that can be pushed and pulled with respect to different side portions of the tube, mechanical expansion, and/or the like) to push a portion of the section against patient tissue), an expanding balloon (see, e.g., electrode(s) 50*b* coupled to expander 164 of FIG. 16), a mechanically expanding electrode structure (see, e.g., electrode(s) 50*b* of an expander 164' of FIG. 17, where expander 164' may be expanded or contracted by increasing or decreasing the distance between ends 161' and 169' of expander 164' (e.g., using any suitable control mechanism of the assembly that may be utilized by an operator when expander 164' is properly positioned within the patient)), steerable tube structures of device delivery assemblies using any suitable mechanisms (see, e.g., a steerable tube 112''' of an assembly 100''' of FIG. 18 steerable in any suitable manner (e.g., using cables 197 that can be pushed and pulled with respect to different side portions of the tube) between a first configuration 112'''*a* and a second configuration 112'''*b* with any suitable electrode(s) 50''' coupled thereto), any suitable heat set (e.g., nickel titanium or nitinol heat set) structure(s) that may be released or allowed to expand when properly positioned within a patient (e.g., electrode(s) 50b" coupled to or provided by a structure of an expander 164" of FIG. 19, where expander 164" may be a nitinol heat set structure or any other structure that may be expanded to its natural state (e.g., as shown in broken line) from a deformed state (e.g., shown in solid line) or deformed from its natural state to a deformed state by releasing the structure from a sheath or movable tube or constraining the structure between ends 161" and 169" in such a sheath or movable tube (e.g., a tube cover 112c that may move distally with respect to structure 164" to cover and deform structure 164" and move proximally with respect to structure 164" to allow structure to expand to its natural state of FIG. 19) or it may be self-expanding heat set structure that may expand when exposed to the heat internal to the patient), fenestration(s) through a tube structure adjacent or proximal to or between or also through one or more electrodes that may induce light suction against the patient's internal wall to promote contact of electrodes with the wall (see, e.g., fenestrations or openings 108b through tube structure 112 adjacent one or more electrodes and/or between one or more electrodes coupled to structure 112 (e.g., electrodes 50e-50e'") and/or openings 108b' through one or more of the electrodes 50 and the tube structure (e.g., an opening 108b through the tube structure may at least partially align with an opening 108b' through an electrode (e.g., suction may be provided through an exterior surface portion of the electrode to even further promote contact of that electrode exterior surface with interior patient tissue)), as shown in FIG. 21), and/or the like. An opening 108b through the tube structure and an opening 108b' through an electrode structure may align in any suitable manner, such as when the electrode is positioned on an exterior surface of the tube structure (e.g., electrode 50a"), at an exterior surface of the tube structure (e.g., electrode 50a), within the tube structure (e.g., electrode 50a'), or in any other suitable manner. In addition to or as an alternative to providing a suctioning force therethrough for holding an internal electrode against or close to internal tissue of a patient, openings 108b and/or opening(s) 108b's may be used (e.g., prior to suctioning) to expel any suitable fluid therefrom (e.g., introducing electroconductive gel or medication or other suitable material(s) to the outer surface of the tube at the level (e.g., portion of length of tube at which one or more electrodes may be coupled or otherwise provided)).

Figure 13:
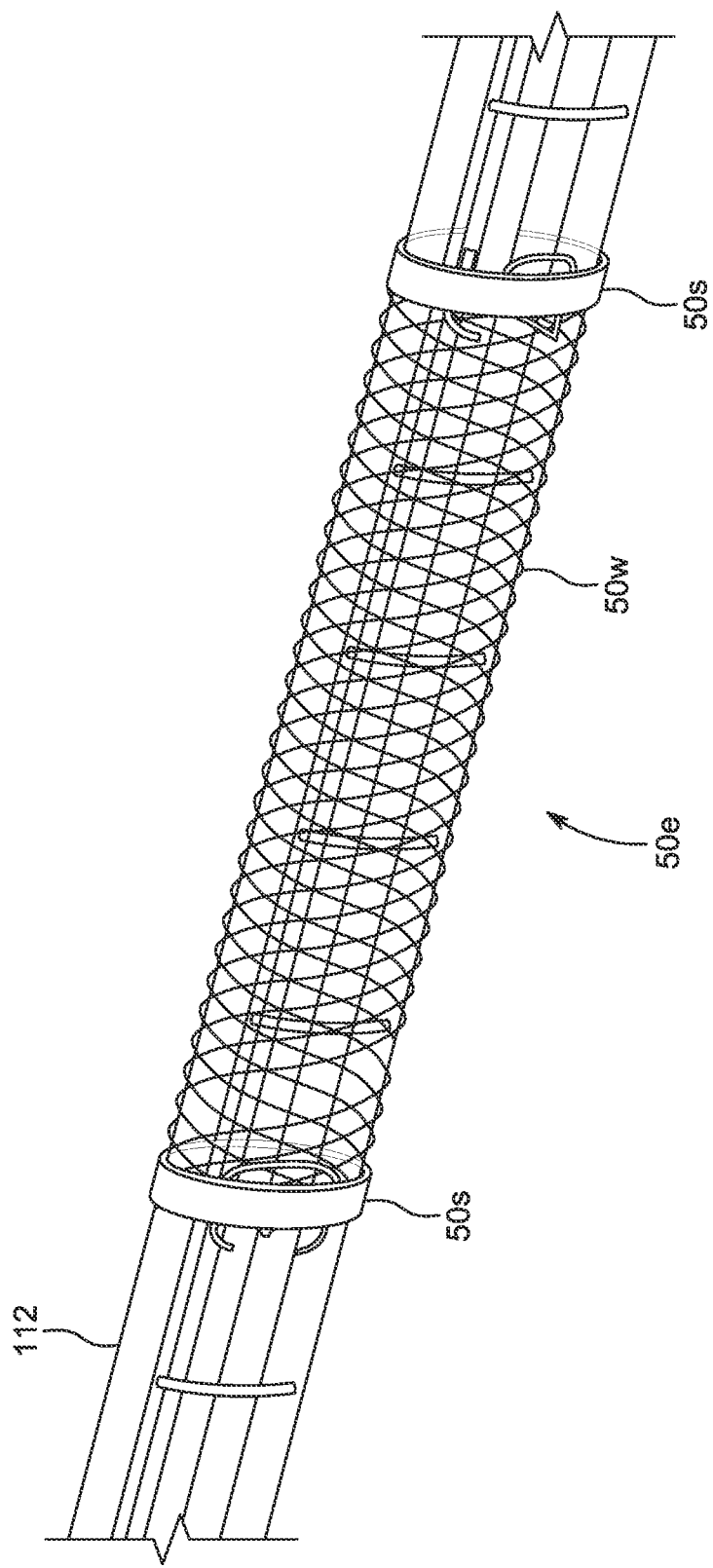
FIG. 13 is a perspective view of a portion of a pacing intubation assembly, according to some embodiments of the disclosure.

In some embodiments, an electrode 50 may be a braided metal wire or multiple wires braided over exterior surface 118 of wall 113 of tube structure 112. For example, an electrode may be provided by the integration of braided metal wire (e.g., multiple wires braided over the tube (e.g., in a particular (e.g., central) section)). Such wire(s) may be flat or rounded in cross-section. Such a wire may be anchored on each end to assembly 100 (e.g., exterior surface 118 of wall 113 of tube structure 112) by a reflow process or build up process (e.g., of the tube material) or adhesive or metal band(s) to ensure the ends are secure and the profile of the assembly may remain substantially smooth. For example, one or more wires 50w may be braided over tube structure 112 between containment bands 50s that may anchor respective ends of wire(s) 50w to tube structure 112 for providing an electrode 50e as shown in FIG. 13.

Figure 14:
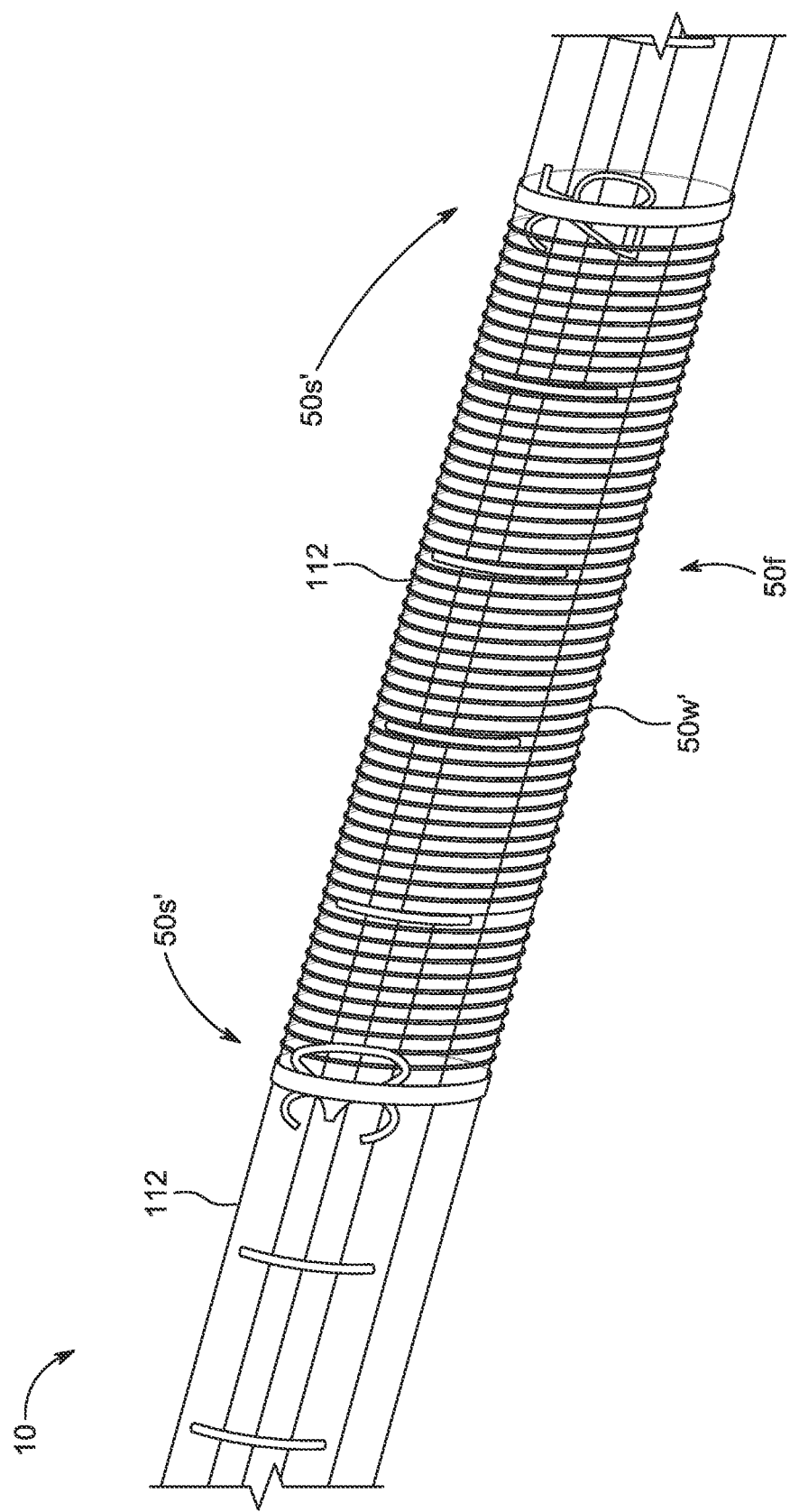
FIG. 14 is a perspective view of a portion of a pacing intubation assembly, according to some embodiments of the disclosure.
Figure 15:
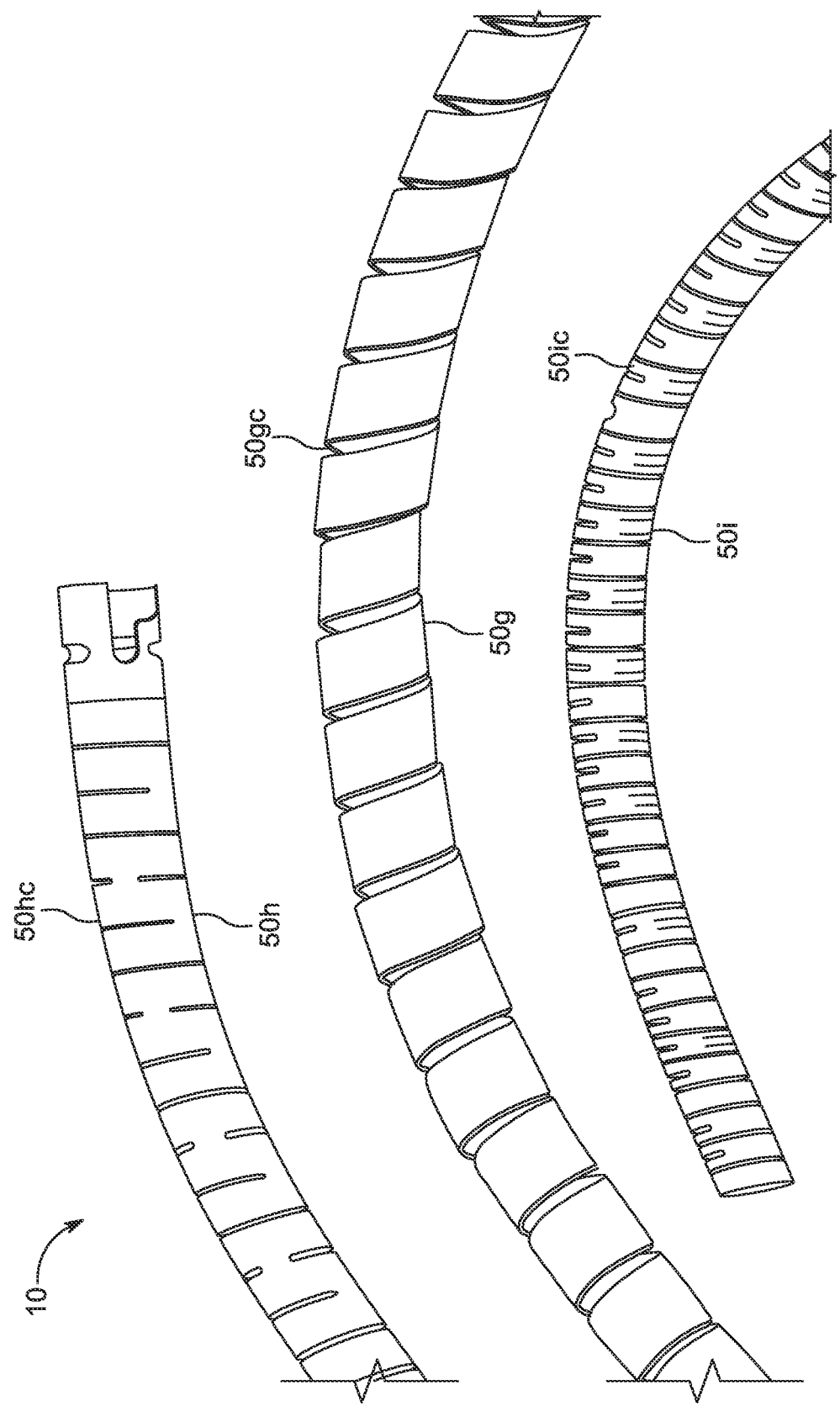
FIG. 15 is a perspective view of a portion of pacing intubation assemblies, according to some embodiments of the disclosure.

In some embodiments, an electrode 50 may be a rounded coil of wire over exterior surface 118 of wall 113 of tube structure 112. For example, an electrode may be provided by the integration of a coil of metal wire. Such a single wire may rounded in cross-section. Such a wire may be anchored on each end to assembly 100 (e.g., exterior surface 118 of wall 113 of tube structure 112) by a reflow process or build up process (e.g., of the tube material) or adhesive or metal bands to ensure the ends are secure and the profile of assembly may remain substantially smooth. For example, a wire 50w' may be coiled over tube structure 112 (e.g., in any suitable number of coil windings about the tube) between containment bands 50s' that may anchor respective ends of wire 50w' to tube structure 112 for providing an electrode 50f as shown in FIG. 14.

In some embodiments, an electrode 50 may be formed by cutting a hollow tube (e.g., a hollow metal tube) in any suitable manner such that the resulting structure may be slipped over a tube of assembly 100 (e.g., over the exterior of tube 112). For example, a single spiral 50gc may be laser cut from a proximal portion to a distal portion of a hollow metal tube in order to form an electrode 50g that may be more flexible and expandable and retractable about a tube of assembly 100. Alternatively, more complex designs 50hc may be laser cut between a proximal portion and a distal portion of a hollow metal tube in order to form an electrode 50h that may be more flexible and expandable and retractable about a tube of assembly 100. Alternatively, even more complex designs 50ic may be laser cut between a proximal portion and a distal portion of a hollow metal tube in order to form an electrode 50i that may be more flexible and expandable and retractable about a tube of assembly 100.

Expansion and contraction of certain types of electrode 50 may induce certain capture of tissue by the electrode and/or assembly 100 (e.g., to hold one or more electrodes against the patient tissue during use of the assembly (e.g., for pacing)). For example, expansion and contraction of electrode 50e of FIG. 13, electrode 50f of FIG. 14, electrode 50g of FIG. 15, electrode 50h of FIG. 15, electrode 50i of FIG. 15, electrode 50b' of FIG. 17, electrode 50b" of FIG. 19, and/or the like (e.g., through expansion and contraction of an underlying expander and/or any other suitable mechanism to cause such expansion and contraction of such an electrode) may create widening and shrinking areas between electrode portions (e.g., between adjacent coil windings of wire 50w' of electrode 50f, between adjacent braid portions of wire 50 of electrode 50e, between different exterior surface portions of the metal tube separated by spiral 50gc of electrode 50g, between different electrode strips of electrode 50b' of FIG. 17, and/or between different electrode strips of electrode 50b" of FIG. 19).

Therefore, one or more internal electrodes 50 may be coupled to or otherwise formed integral with any suitable tube subassembly 110 of any suitable delivery device assembly 100 of system 10, thereby allowing the tube subassembly 110 and internal electrode(s) 50 to be placed in an operative position within a patient 1 simultaneously. System 10 may include one or more internal electrode(s) 50 that may be uniquely designed specifically for integration of cardiac stimulation from the esophagus and retention of naso/orogastric tube function and placement of delivery device assembly 100. Internal electrode(s) 50 may be designed to ensure flexibility and ease of passage into and out from the patient. External electrode(s) 70 (e.g., external chest pad or electrode 70a) may be easily detachable from patient 1 to ensure easy replacement of electrode(s) 70 while not also requiring replacement of electrode(s) 50 (e.g., so that assembly 100 does not need to be removed from the patient or exchanged every time a pad 70 is replaced or adjusted). An array of two or more internal electrodes 50 along a delivery device assembly 100 may be designed in size and distribution in order to accommodate for the natural variation in movement that may occur with the use of a naso/orogastric tube while still maintaining the capability of electrical cardiac stimulation. For example, an array of 3-5 electrodes linearly distributed along a length of tube assembly 112 of at least 5 centimeters (e.g., length LS spanned by electrodes 50*e*-50*e*''' of FIG. 21 may be at least 5 centimeters) may be operative to account for the natural variation in electrode movement as a patient extends and flexes their neck while assembly 100 may be positioned within the patient for use (e.g., the position of FIG. 7 or FIG. 8). For example, by using a band electrode that may extend about an entire or substantially an entire cross-sectional periphery of a tube structure, a portion of the electrode may be able to contact patient tissue or at least be facing a patient's heart regardless of the rotational orientation of that cross-sectional periphery (e.g., rotation about axis A and/or Y-axis of FIGS. 2C and 3B). A band electrode (e.g., band electrode 50*d* or band electrode 50*e*) may extend entirely about the periphery of a tube assembly (e.g., a ring or uninterrupted structure about a tube's periphery) or may extend substantially but not entirely about the periphery of the tube assembly such that the electrode's cross-section may expand and contract (e.g., a C-shaped band rather than an O-shaped band).

Another particular example of a transesophageal ventricular pacing system may be shown by system 10'''' of FIGS. 22 and 22A-22C, which may include a delivery device assembly 100'''' that may be configured to deliver any suitable number of internal electrodes 50 (e.g., electrodes 50*d*, 50*d*', 50*d*'', and 50*d*''') into a functional position within a patient for use with any suitable pacing device that may be electrically coupled to internal electrode(s) 50 by any suitable internal electrode coupler(s) 51 and to any suitable external electrode(s) by any suitable external electrode coupler(s). Assembly 100'''' may extend between a proximal or first assembly end 101'''' and a distal or second assembly end 109''''. Assembly 100'''' may include at least one tube or tube subassembly 110'''' providing a body structure 112'''' (e.g., catheter or tube) that may extend between ends 101'''' and 109'''', while any suitable hub 196'''' may be provided about or for providing any suitable passageway ends at or near end 101''''. Tube subassembly 110'''' may include at least one tube wall 113'''' that may define at least one internal or intubation lumen or passageway 115'''' extending within and along at least a portion of assembly 100''''. For example, tube wall(s) 113'''' that may provide one or more surfaces 111'''' that may define passageway 115''''. Wall 113'''' may also include at least one proximal or first tube opening 102'' that may provide access to passageway 115'''' (e.g., fluid communication between passageway 115'''' and an ambient environment of assembly 100'''') at or near end 101'''' of assembly 100'''' and at least one distal or second tube opening 108*b*'''' that may provide access to passageway 115'''' (e.g., fluid communication between passageway 115'''' and an ambient environment of assembly 100'''') at or near end 109'''' of assembly 100'''' (e.g., one or more side wall openings (e.g., 8 distinct openings 108*b*'''' or 4 ring shaped openings 108*b*'''' of FIG. 22)) may be provided through wall 113'''' along a side of body structure 112'''' (e.g., proximal of distal end 109'''')). Passageway 115'''' may be used for any suitable functionality (e.g., for passing gastric contents between opening(s) 102'''' and opening(s) 108*b*'''' when at least one opening 108*b*'''' is positioned appropriately within a patient (e.g., within the patient's esophagus or stomach)). Tube wall(s) 113'''' of subassembly 110'''' may also provide one or more surfaces 117'''' of tube subassembly 110'''' that may define at least one vent passageway 119''' for extending between at least one other proximal or third tube or vent opening 104'''' that may provide access to vent passageway 119'''' (e.g., fluid communication between vent passageway 119'''' and an ambient environment of body structure 112'''' of subassembly 110'''') at or near end 101'''' of assembly 100'''' and at least one distal or fourth tube or vent opening 106'' that may provide access to passageway 119'''' (e.g., fluid communication between vent passageway 119'''' and an ambient environment of body structure 112'''' of subassembly 110'') at a position along the length of assembly 100'''' distal of opening 104'''' (e.g., through a side wall portion of wall 113'''' adjacent end 109''), where opening 106'''' may be operative to fluidly couple vent passageway 119'''' of tube subassembly 110'''' to an ambient environment of opening 106'''' (e.g., within a patient when assembly 100'''' positioned appropriately). Passageway 119'''' may be used for any suitable functionality (e.g., as a vent for assistance with gastric decompression between opening(s) 104'''' and opening(s) 106'''' when at least one opening 106'''' is positioned appropriately within a patient (e.g., within the patient's esophagus or stomach)). In some embodiments, as shown, assembly 100'''' may also include a supplemental tube passageway 195'''' that may be defined by at least a portion of one or more walls 113'''' of tube subassembly 110 that may be provided to treat (e.g., extract material from and/or inject material into) a supplemental region of a patient and/or pass any suitable electrode coupler(s) 51 through a portion of assembly 100'''' (e.g., passageway 195'''' may be insulative) for eventual coupling with one or more internal electrodes 50. Supplemental tube passageway 195'''' may extend from a proximal end 191'''' to at least one or more distal ends 199 (e.g., one at or near a respective internal electrode). A proximal opening 192'''' for passageway 195'''' may be provided at or near proximal end 191'''' and a distal opening 198'''' for passageway 195'''' may be provided at or near distal end 199''. Fluid may be injected through passageway 195'''' and out from one or more distal openings 198'''' (e.g., conductive gel near an internal electrode) and/or one or more couplers 51 may extend through passageway 195'''' at least from between an opening 192'''' and an opening 198'''' for coupling to an internal electrode 50.

An opening 108*b*'''' may have any suitable maximum cross-sectional width OCW, such as in a range between 0.2 and 2.0 millimeters or about or equal to 1.0 millimeter, and any suitable maximum cross-sectional length OCL, such as in a range between 3.5 and 5.5 millimeters or about or equal to 4.5 millimeters, although any other suitable dimensions may be possible. A most distal opening 108*b*'''' may be any suitable distance DDE from distal end 109'''', such as in a range between 11.0 and 13.0 millimeters or about or equal to 12.0 millimeters, although any other suitable dimensions may be possible. Adjacent distal openings 108*b*'''' may be any suitable distance DDS apart from each other (e.g., from distal tip of one to distal tip of other, as shown), such as in a range between 11.0 and 13.0 millimeters or about or equal to 12.0 millimeters, although any other suitable dimensions may be possible. A most distal internal electrode 50 may be any suitable distance DDC from distal end 109'''', such as in a range between 120.0 and 180.0 millimeters or about or equal to 150.0 millimeters, although any other suitable dimensions may be possible. Therefore, a most distal electrode 50*d* may be any suitable distance EOP from a most proximal opening 108*b*'''', such as in a range between 82.0 and 112.0 millimeters or about or equal to 97.5 millimeters, although any other suitable dimensions may be possible (e.g., such that suction from an opening 108*b*'''' may promote holding electrode 50*d* against or adjacent nearby internal patient tissue). Adjacent internal electrodes may be any suitable distance DCS apart from each other, such as in a range between 7.0 and 13.0 millimeters or between 9.0 and 11.0 millimeters or about or equal to 10.0 millimeters, although any other suitable dimensions may be possible. An internal electrode may have any suitable width IEW, such as in a range between 3.04 and 3.24 millimeters or about or equal to 3.14 millimeters, although any other suitable dimensions may be possible. An internal electrode may have any suitable cross-sectional thickness IET, such as in a range between 0.20 and 0.30 millimeters or about or equal to 0.25 millimeters, although any other suitable dimensions may be possible. An internal electrode may have any suitable cross-sectional outer diameter or height IEH, such as in a range between 5.10 and 7.10 millimeters or about or equal to 6.10 millimeters, although any other suitable dimensions may be possible. A tube 112"" may have any suitable cross-sectional outer diameter or height TEH when an electrode 50 is positioned thereabout, such as in a range between 4.592 and 6.592 millimeters or about or equal to 5.592 millimeters, although any other suitable dimensions may be possible, while tube 112"" may have any other suitable cross-sectional outer diameter or height TEH' when an electrode 50 is not positioned thereabout, such as in a range between 5.0 and 7.0 millimeters or about or equal to 6.0 millimeters, although any other suitable dimensions may be possible (e.g., whereby a band electrode may be operative to compress the tube by any suitable dimension). Tube 112"" may have any suitable length TL between end 101"" and end 109"", such as in a range between 75.0 and 95.0 centimeters or about or equal to 85.0 centimeters, although any other suitable dimensions may be possible. Passageway 119"" and/or passageway 195"" may include any suitable cross-sectional shape, including a shape that may accommodate a maximum cross-sectional diameter SCD, such as in a range between 0.82 and 1.02 millimeters or about or equal to 0.92 millimeters, although any other suitable dimensions may be possible (e.g., where SCD may be at least slightly bigger than any maximum diameter of any coupling 51). Passageway 115"" may include any suitable cross-sectional shape, including a shape that may accommodate a maximum cross-sectional diameter MCD, such as in a range between 2.53 and 2.93 millimeters or about or equal to 2.73 millimeters, although any other suitable dimensions may be possible (e.g., where MCD may be at least slightly bigger than any maximum diameter of any gastric contents to be passed therethrough). A linear distribution of an electrode array of at least 40 millimeters (e.g., an array spanning electrodes 50d-50d"") may be operative to account for any natural variation in electrode movement as a patient extends and flexes their next while the delivery assembly is positioned within the patient.

One or more of electrode(s) 50 and/or electrode(s) 70 may be any suitable type of electrode, including a unipolar electrode, a bipolar electrode, a point source electrode, a lead tip electrode, a cathode electrode, an anode electrode, a low impedance electrode (e.g., an R2 pad (e.g., 5 ohms)), a high impedance electrode (e.g., a Zoll pad (e.g., 250 ohms)), and/or the like, and any suitable pulsing may be carried out (e.g., duration of current pulses (e.g., 1-50 msec, 20 msec, etc.)) and/or mean threshold current (e.g., 11-50 mA, 16 mA, 45 mA, etc.) and/or the like).

A delivery device may be provided with one or more internal electrodes configured for enabling unipolar esophageal pacing of a patient or with two or more internal electrodes configured for enabling bipolar esophageal pacing of a patient. In either a unipolar or a bipolar system, a pacing signal or current (e.g., signal 40 or signal 80) is provided by a pacing device (e.g., device 30) to a first electrode (e.g., a positive electrode or current passing electrode or cathode) that then attempts to distribute the pacing signal or current to a second electrode (e.g., a negative electrode or ground electrode or current receiving electrode or anode) via a path that preferably pass through a portion of a patient's heart. A bipolar esophageal pacing system may integrate both the current passing electrode and the current receiving electrode (e.g., both the cathode and anode, both the positive electrode and the negative or ground electrode, etc.) on the delivery device assembly (e.g., a catheter positioned within the esophagus of the patient), while a unipolar esophageal pacing system may integrate one type of electrode (e.g., a single electrode or two or more electrodes coupled in parallel), usually the current passing electrode (e.g., the cathode, the positive electrode, etc.), on the delivery device assembly (e.g., a catheter positioned within the esophagus of the patient) and may position the other electrode type, usually the current receiving electrode (e.g., the anode, the negative or ground electrode, etc.), on the exterior chest wall of the patient (e.g., in the form of a chest wall pad electrode). In most embodiments of this disclosure, a delivery assembly provided with one or more internal electrodes may be utilized in a unipolar esophageal pacing system (e.g., as unipolar designs may have a distinct advantage of being able to pace the heart ventricles reliably whereas bipolar designs have been proven to be ineffective at this). Such a unipolar esophageal pacing system may be configured to include any suitable features to better integrate the unipolar design and internal electrode(s) with the functionality of a delivery assembly (e.g., an indwelling naso/orogastric tube assembly), including, but not limited to, (1) multiple internal electrodes (e.g., two or more internal electrodes (e.g., positive electrodes) that may be electrically coupled in parallel for receiving the same signal from a port or connector of a pacing device) that may be positioned in different positions along the delivery assembly such that the different electrodes may distribute current equally (e.g., provide equal voltage potential) between each internal electrode and an external (e.g., ground) electrode (e.g., in order to help minimize the effect of patient movement while the delivery assembly is positioned within the patient and increase chances of capture), (2) features that may augment or enhance contact (e.g., maintain contact and/or promote retention) between a patient's internal tissue (e.g., esophageal wall) and a delivery assembly and/or its coupled internal electrode(s) (e.g., to maintain a particular position of one or more internal electrodes with respect to a particular portion of the patient's internal tissue), (3) features that may allow for a safe and seamless integration of the delivery assembly and associated electrode(s) with various types of pulse generators (e.g., different types of pacing devices 30 (e.g., biphasic pulse generators, monophasic pulse generators, etc. (e.g., biphasic defibrillators, monophasic defibrillators, etc.))), (4) features that may allow for a larger internal electrode array to integrate in such a way as to maintain the flexibility needed for a tube of the delivery assembly (e.g., braid electrode(s), coil electrode(s), expander electrode(s), multiple band electrodes electrically coupled in parallel, and/or the like may be coupled to and delivered into the patient by a delivery assembly tube that may be configured to make any suitable flexible turns in a nasopharynx or other suitable internal portion(s) of a patient), and/or the like.

In some embodiments, a unipolar esophageal pacing system of the disclosure may be used with a pacing device or defibrillator configured to provide monophasic defibrillation. For example, system 10 of FIG. 1 may be configured as a unipolar esophageal pacing system, where pacing device 30 may be configured as a monophasic pulse generator for repeatedly sending a high energy monophasic electrical pulse 40 (e.g., a monophasic (e.g., one phase) current or electrical impulses or signals) to a positive electrode or to a group of positive electrodes electrically coupled to one another in parallel via any suitable coupler(s) 51 (e.g., to internal electrode(s) 50 provided by delivery assembly 100 within patient 1), and each internal electrode(s) may pass the signal to a negative or ground electrode (e.g., external electrode 70) via any suitable path 61 (e.g., preferably via heart 99 of patient 1 when assembly 100 is appropriately positioned within the patient). As shown in FIG. 1, pacing device 30 may include a first device port or connector 36a and a second device port or connector 36b, coupler 51 may extend between a first coupler connector 56a and a second coupler connector 56b, and coupler 71 may extend between a first coupler connector 76a and a second coupler connector 76b. First coupler connector 56a of coupler 51 may be configured to be electrically coupled to, if not also physically coupled to, first device connector 36a of pacing device 30, while second coupler connector 56b of coupler 51 may be configured to be electrically coupled to, if not also physically coupled to, an internal electrode connector 56b' of one, some, or each internal electrode 50, such that any suitable signal 40 (e.g., a monophasic electrical pulse) may be communicated from pacing device 30 to one, some, or each internal electrode 50 via connector 36a, connector 56a, coupler 51, connector 56b, and any connector(s) 56b'. First coupler connector 76a of coupler 71 may be configured to be electrically coupled to, if not also physically coupled to, second device connector 36b of pacing device 30, while second coupler connector 76b of coupler 71 may be configured to be electrically coupled to, if not also physically coupled to, an external electrode connector 76b' of external electrode 70, such that any suitable signal 80 may be communicated between electrode 70 and pacing device 30 via connector 76b', connector 76b, coupler 71, connector 76a, and connector 36b. Each coupler connector, each device connector, and/or each electrode connector may be any suitable connector type for enabling any suitable electrical if not also any suitable physical coupling between itself and an associated connector of another system component (e.g., a male connector, female connector, genderless connector, etc. with any suitable type(s) and/or number of pins or other suitable features). In some embodiments, a coupling between two connectors may be configured to be removable (e.g., easily coupled and decoupled by an end user (e.g., operator O), such as an R2 connector coupling (e.g., between connector 76a and connector 36b)), or a coupling between two connectors may be configured to be permanent (e.g., not easily coupled and decoupled by an end user (e.g., operator O), such as a soldered connection (e.g., between connector 56b (e.g., a wire end of parallel coupler branch 51d of coupler 51 of FIG. 12) and connector 56b' (e.g., a solder pad portion of an electrode (e.g., an interior surface portion of electrode 50d that may be soldered to a wire end of parallel coupler branch 51d of coupler 51 of FIG. 12)))). An exterior electrode 70 may be provided as a chest pad electrode 70a, which may include a pad with an adhesive outer edge and an electroconductive center with conductive metal. Electrode 70 may be removably coupled to connector 76b of coupler 71 (e.g., connectors 76b and 76b' may be a coupling that is detachable by an end user) and/or connector 76a of coupler 71 may be removably coupled to connector 36b of pacing device 30 (e.g., connectors 76a and 36b may be a coupling that is detachable by an end user), whereby electrode 70, with or without lead(s) or coupler 71, may be easily replaced with respect to the rest of the system (e.g., electrode 70 may be replaced while delivery device 100 and any internal electrode(s) 50 may remain in patient 1).

As mentioned, two or more different internal electrodes provided by a delivery assembly into a patient may be electrically coupled in parallel to the same coupler 51 (e.g., for providing the same signal 40 to each of such internal electrodes (see, e.g., electrodes 50d-50d'''' of FIG. 12). In other embodiments, two or more different internal electrodes provided by a delivery assembly into a patient may be electrically coupled to respective different couplers (e.g., for providing different signals to the different internal electrodes (e.g., from different ports of a pacing device)). In yet other embodiments, two or more different internal electrodes provided by a delivery assembly into a patient may be electrically coupled in series, where a first electrode (e.g., electrode 50e'''' may be electrically coupled to a coupler 51, while electrode 50e'' may be electrically coupled in series to electrode 50e''' and is only electrically coupled to coupler 51 via electrode 50e'''). If two or more internal electrodes are coupled in series, then a current would simply move off the internal electrode closest to the external electrode (e.g., by using the path of least resistance), whereby the voltage potential between the different electrodes would be uneven and, therefore, the current distribution (e.g., between the external electrode and the internal electrode) would be uneven as well. However, by coupling two or more internal electrodes in parallel, the voltage potential at each parallel internal electrode between the internal electrode and the external electrode would be the same (e.g., constant) and the system may have more uniform current flow between the electrodes. This may result in each electrode having a more predictable pacing profile, whereby, as the patient may move (e.g., flexes their neck up and down) while the delivery assembly positions the internal electrodes within the patient, different internal electrodes can take up pacing as the current from different electrodes may be traversing the heart (e.g., at the same time or at different times (see, e.g., FIGS. 7 and 8)). Therefore, two or more internal electrodes may be supplied current in parallel to ensure even distribution of current across the electrode array. An advantage may be that, as a delivery assembly remains in a patient for a long period of time, it may be relied on to provide continuous and reliable pacing (e.g., for up to 72 hours or more), such that, by having a design feature that builds in internal electrode redundancy, whereby small movements of the electrodes (e.g., due to patient movement of their internal tissue or operator movement of the assembly) may not cause the patient's heart to lose capture, the system may be more reliable and effective (e.g., at least one if not two or more captures may occur despite movement of the internal electrodes with respect to the patient (see, e.g., FIGS. 7 and 8)).

For many years, external defibrillators often relied on monophasic (e.g., one phase) current or electrical impulses, where electrical pulses are quickly sent from one electrode to the other in one direction. However, more recently, biphasic pulse generators have become more widely used. Today, biphasic current has largely replaced monophasic as the superior method, so much so that monophasic pacing devices are rarely manufactured anymore. Therefore, in some embodiments, a unipolar esophageal pacing system of the disclosure may be used with a pacing device or defibrillator (e.g., bedside monitor or signal generator) configured to provide biphasic current. For example, system 10 of FIG. 1 may be configured as a unipolar esophageal pacing system, where pacing device 30 may be configured as a biphasic pulse generator for alternating between (1) sending a first biphasic electrical pulse 40 (e.g., a first (e.g., one phase) current or electrical impulse or signal (e.g., from connector 36a)) to a first electrode or to a group of first electrodes electrically coupled to one another in parallel via any suitable coupler(s) 51 (e.g., to internal electrode(s) 50 provided by delivery assembly 100 within patient 1) where the first electrode(s) may pass the signal to a second electrode (e.g., external electrode 70) via any suitable path 61 (e.g., preferably via heart 99 of patient 1 when assembly 100 with electrode(s) 50 is appropriately positioned within the patient) and (2) sending a second biphasic electrical pulse 80 (e.g., a second (e.g., one phase) current or electrical impulse or signal (e.g., from connector 36b)) to a second electrode or to a group of second electrodes electrically coupled to one another in parallel via any suitable coupler(s) 71 (e.g., to external electrode 70) where the second electrode may pass the signal to a first electrode or group of first electrodes (e.g., internal electrode(s) 50) via any suitable path 61 (e.g., preferably via heart 99 of patient 1 when assembly 100 with electrode(s) 50 is appropriately positioned within the patient). However, such biphasic current flow is often used to provide pacing and/or cardioversion/defibrillation electrical impulses between two different external electrodes 70 (e.g., via two chest pad electrodes) rather than between an external electrode 70 and two or more internal electrodes 50 (e.g., esophageal electrode(s) positioned within a patient's esophagus and/or stomach). For example, rather than a monophasic current moving only from a first type of electrode (or group of a first type of electrodes in parallel) to a second type of electrode (e.g., ideally from esophagus internal electrode(s) through the heart then into a chest pad electrode), a biphasic current may travel from the first type of electrode to the second type of electrode, then switch polarity, and travel back from the second type of electrode to the first type of electrode. With a unipolar system, this biphasic operation can result in too much skeletal muscle activation on the passing of the signal back from the external electrode to the internal electrode(s) (e.g., when the current originates at the external electrode), which can be uncomfortable for the patient (e.g., such a signal may activate fibers in the patient's interior wall and may cause twitching).

Figure 1B:
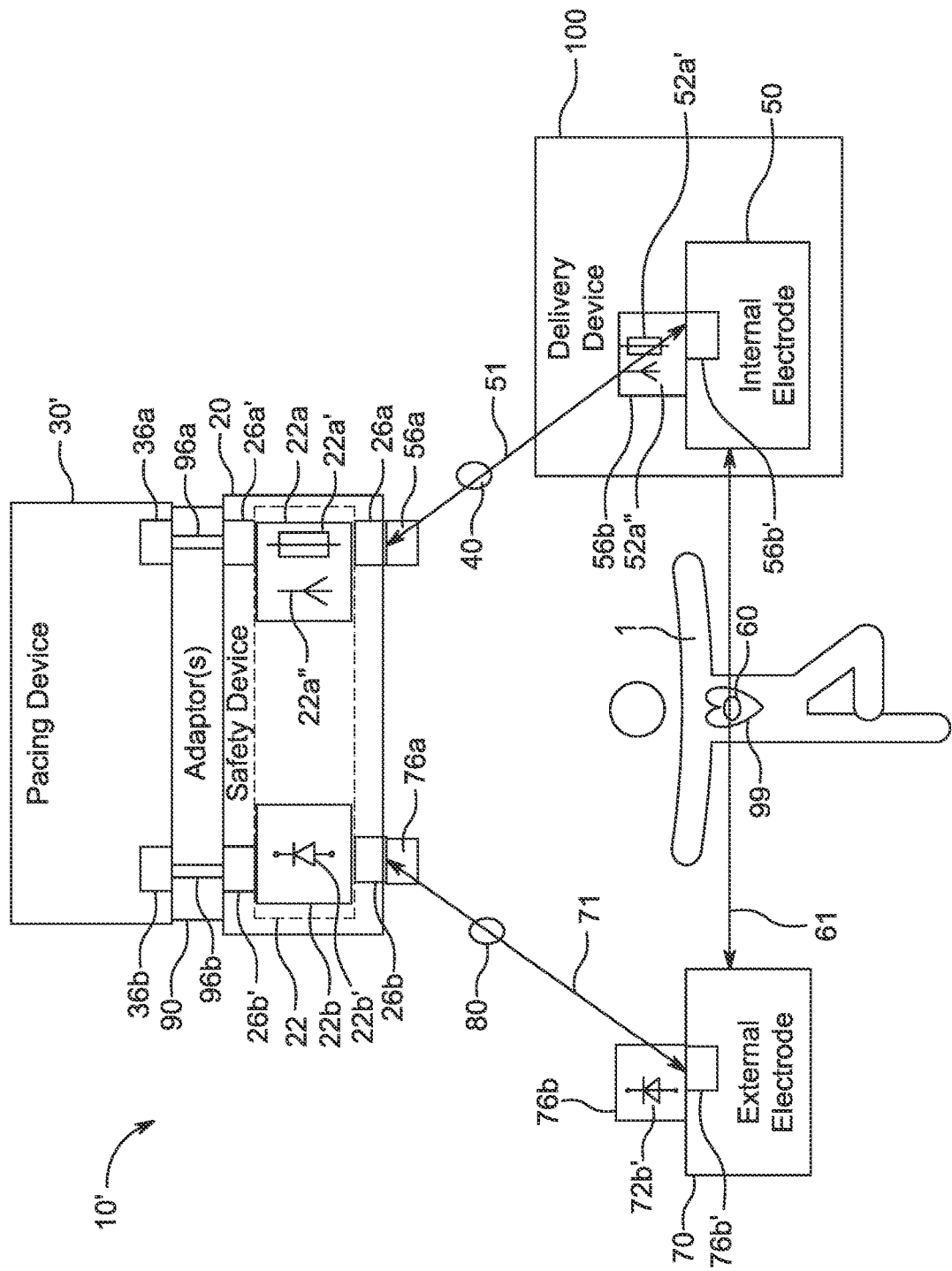
FIG. 1B is a schematic diagram illustrating a pacing intubation system with a safety connector device, according to some embodiments of the disclosure.

Therefore, in some embodiments, a system (e.g., a transesophageal ventricular pacing system) may be provided with a safety device or assembly that may provide an interface between any suitable electrode(s) of the system and a pacing device (e.g., defibrillator (e.g., bedside monitor or signal generator)), so that the safety device may protect a patient in certain circumstances (e.g., if the pacing device were configured to provide biphasic defibrillation). For example, as shown in FIG. 1B, a system 10' may be similar to system 10 of FIG. 1, but may include a safety device or assembly 20 and the pacing device may be a particular pacing device 30' configured to provide biphasic defibrillation or unknown defibrillation (e.g., device 30' may be a biphasic pacing device rather than a monophasic pacing device, or device 30' may be a monophasic pacing device or a pacing device of an unknown type). Safety device 20 may provide an interface between any suitable electrode(s) of system 10' and pacing device 30'. In some embodiments, a unipolar esophageal pacing system of the disclosure may be used with a pacing device or defibrillator configured to provide biphasic defibrillation or unknown defibrillation. For example, system 10' of FIG. 1B may be configured as a unipolar esophageal pacing system, where pacing device 30' may be configured as a monophasic pulse generator for repeatedly sending a high energy monophasic electrical pulse 40 (e.g., a monophasic (e.g., one phase) current or electrical impulse or signal) to a positive electrode or to a group of positive electrodes electrically coupled to one another in parallel via any suitable coupler(s) 51 (e.g., to internal electrode(s) 50 provided by delivery assembly 100 within patient 1), and each internal electrode(s) may pass the signal to a negative or ground electrode (e.g., external electrode 70) via any suitable path 61 (e.g., preferably via heart 99 of patient 1 when assembly 100 is appropriately positioned within the patient), or where pacing device 30' may be configured as a biphasic pulse generator for alternating between (1) sending a first biphasic electrical pulse 40 (e.g., a first (e.g., one phase) current or electrical impulse or signal (e.g., from connector 36a)) to a first electrode or to a group of first electrodes electrically coupled to one another in parallel via any suitable coupler(s) 51 (e.g., to internal electrode(s) 50 provided by delivery assembly 100 within patient 1) where the first electrode(s) may pass the signal to a second electrode (e.g., external electrode 70) via any suitable path 61 (e.g., preferably via heart 99 of patient 1 when assembly 100 with electrode(s) 50 is appropriately positioned within the patient) and (2) sending a second biphasic electrical pulse 80 (e.g., a second (e.g., one phase) current or electrical impulse or signal (e.g., from connector 36b)) to a second electrode or to a group of second electrodes electrically coupled to one another in parallel via any suitable coupler(s) 71 (e.g., to external electrode 70) where the second electrode may pass the signal to a first electrode or group of first electrodes (e.g., internal electrode(s) 50) via any suitable path 61 (e.g., preferably via heart 99 of patient 1 when assembly 100 with electrode(s) 50 is appropriately positioned within the patient). However, due to system 10' of FIG. 1B being configured as a unipolar esophageal pacing system, safety device 20 may be provided to prevent any such second biphasic electrical pulse 80 (e.g., a second (e.g., one phase) current or electrical impulse or signal) being provided from device 30' (e.g., from connector 36b) to a second electrode or to a group of second electrodes electrically coupled to one another in parallel via any suitable coupler(s) 71 (e.g., to external electrode 70) where the second electrode may pass the signal to a first electrode or group of first electrodes (e.g., internal electrode(s) 50) via any suitable path 61, such that patient 1 might be protected. Therefore, as shown in FIG. 1B, safety device 20 may include a first safety device port or connector 26a' that may be electrically coupled (e.g., removably coupled) to first pacing device connector 36a of pacing device 30' (e.g., either directly or via any suitable adaptor coupler 96a (e.g., of any suitable adaptor device 90) that may be configured to enable an electrical coupling between any suitable connector 36a and any suitable connector 26a'). Safety device 20 may also include a second safety device port or connector 26b' that may be electrically coupled (e.g., removably coupled) to second pacing device connector 36b of pacing device 30' (e.g., either directly or via any suitable adaptor coupler 96b (e.g., of any suitable adaptor device 90) that may be configured to enable an electrical coupling between any suitable connector 36b and any suitable connector 26b'). Different adaptors 96 and/or different adaptor devices 90 may be provided with safety device 20 (e.g., by a supplier of safety device 20 or otherwise) depending on the type of pacing device being coupled to the safety device. Safety device 20 may also include a first safety electrode port or connector 26a and a second safety electrode port or connector 26b. Moreover, safety device 20 may include any suitable safety circuitry assembly 22 functionally coupled between at least one safety device connector and at least one safety electrode connector (e.g., between connector(s) 26a'/26b' and connector (s) 26*a*/26*b*) for enabling any suitable safety functionality on a signal passed through safety device 20 (e.g., first safety circuitry 22*a* of safety circuitry assembly 22 may be functionally coupled between first safety device connector 26*a*' and first safety electrode connector 26*a* and/or second safety circuitry 22*b* of safety circuitry assembly 22 may be functionally coupled between second safety device connector 26*b*' and second safety electrode connector 26*b* to carry out any suitable safety functionalities or otherwise on any signal(s) to be communicated through safety device 20). First coupler connector 56*a* of coupler 51 may be configured to be electrically coupled to, if not also physically coupled to, first safety electrode connector 26*a* of safety device 20, while second coupler connector 56*b* of coupler 51 may be configured to be electrically coupled to, if not also physically coupled to, an internal electrode connector 56*b*' of one, some, or each internal electrode 50, such that any suitable signal 40 may be communicated between pacing device 30 to one, some, or each internal electrode 50 via connector 36*a*, connector 26*a*' (e.g., directly or via adaptor 96*a*), first safety circuitry 22*a*, connector 26*a*, connector 56*a*, coupler 51, connector 56*b*, and any connector(s) 56*b*'. First coupler connector 76*a* of coupler 71 may be configured to be electrically coupled to, if not also physically coupled to, second safety electrode connector 26*b* of safety device 20, while second coupler connector 76*b* of coupler 71 may be configured to be electrically coupled to, if not also physically coupled to, an external electrode connector 76*b*' of external electrode 70, such that any suitable signal 80 may be communicated between electrode 70 and pacing device 30 via connector 76*b*', connector 76*b*, coupler 71, connector 76*a*, connector 26*b*, second safety circuitry 22*b*, connector 26*b*', and connector 36*b* (e.g. directly or via adaptor 96*b*). Each coupler connector, each device connector, each safety electrode connector, each safety device connector, each adaptor coupler, and/or each electrode connector may be any suitable connector type for enabling any suitable electrical if not also any suitable physical coupling between itself and an associated connector of another system component (e.g., a male connector, female connector, genderless connector, etc. with any suitable type(s) and/or number of pins or other suitable features). In some embodiments, a coupling between two such connectors of system 10' may be configured to be removable (e.g., easily coupled and decoupled by an end user (e.g., operator O)), or a coupling between two such connectors of system 10' may be configured to be permanent (e.g., not easily coupled and decoupled by an end user (e.g., operator O)). External electrode(s) 70 (e.g., external chest pad or electrode 70*a*) may be easily detachable from patient 1 to ensure easy replacement of electrode(s) 70 while not also requiring replacement of electrode(s) 50 (e.g., so that assembly 100 does not need to be removed from the patient or exchanged every time a pad 70 is replaced or adjusted). The system may be designed in a way that the external pad can be exchanged without having to remove the internal catheter (e.g., allow assembly 100 to stay inside the patient longer but allow electrode 70 to be removed and replaced (e.g., safety device 20 may be configured to allow distinct couplings of couplings 51 and 71 (e.g., a coupling between connector 76*a* and 26*b* may be removed or replaced without changing any coupling between connector 56*a* and connector 26*a* (e.g., connectors 56*a* and 26*b* may be distinct and not in the same housing)))).

Safety circuitry 22 may be configured to protect patient 1 from any dangerous signal(s) that may be output by pacing device 30' (e.g., when system 10' is a transesophageal ventricular pacing system). For example, in order to protect patient 1 during use of system 10' when pacing device 30' is known to be biphasic or is of an unknown configuration, safety circuitry 22 may include any suitable first safety circuitry 22*a* that may be configured to prevent a signal 40 with a current above any suitable maximum current or energy threshold from being communicated from pacing device 30' from device connector 36*a* to any internal electrode 50 (e.g., via adaptor 96 and/or safety device 20 and coupler 51). Such first safety circuitry 22*a* include any suitable current limiter or circuit breaker or fuse (e.g., fuse 22*a*') and may be set to prevent signal 40 with a current above any suitable maximum energy threshold from being communicated to an internal electrode 50 (e.g., a maximum energy threshold of 100 Joules (e.g., 100 Volt Amperes) or any other suitable threshold above which may cause harm to patient 1 during use of system 10' (e.g., a transcutaneous system may often start at 100 Joules and anything more can be damaging if used in an esophageal based electrode configuration)). This may limit the passed signal to anything at or below the predetermined or set threshold. In other embodiments, as also shown in FIG. 1B, rather than utilizing such first safety circuitry 22*a* within a safety device 20, similar first safety circuitry (e.g., fuse 52*a*') may be provided by coupler 51 (e.g., within connector 56*b*), which may obviate the need for at least circuitry 22*a* if not also safety device 20, such that connector 56*a* may be coupled directly to connector 36*a*. Similarly, coupler parallel splitting circuitry may be provided anywhere within system 10' to enable a single signal 40 provided by connector 36*a* of pacing device 30' to be coupled to multiple internal electrodes 50 in parallel (e.g., by a coupler parallel splitter 22*a*'' that may be provided by first safety circuitry 22*a* for splitting any signal at connector 26*a*' from connector 36*a* into two or more connectors 26*a* to be coupled to respective connectors 56*a* of respective couplers 51 for respective electrodes 50 to be coupled in parallel, or by a coupler parallel splitter 52*a*'' that may be provided by coupler 51 (e.g., within connector 56*b* (see, e.g., FIG. 12)). Additionally or alternatively to first safety circuitry 22*a*, in order to protect patient 1 during use of system 10' when pacing device 30' is known to be biphasic or is of an unknown configuration, safety circuitry 22 may include any suitable second safety circuitry 22*b* that may be configured to prevent any suitable signal 80 (e.g., a second biphasic electrical pulse 80 (e.g., a second (e.g., one phase) current or electrical impulse or signal)) from being communicated from pacing device 30' from connector 36*b* to any electrode 70 (e.g., via adaptor 96 and/or safety device 20 and coupler 71). Such second safety circuitry 22*b* include any suitable circuitry operative to enable only unidirectional current flow, such as a diode 22*b*', such that current may only be enabled to flow from connector 26*b* to connector 26*b*' (e.g., from electrode 70 to connector 36*b* of pacing device 30') and not also from connector 26*b*' to connector 26*b* (e.g., from connector 36*b* of pacing device 30' to electrode 70), which may prevent a positive biphasic signal from being passed from pacing device 30' to electrode 70 and then through patient 1, which may cause harm to patient 1 during use of system 10' (e.g., diode 22*b*' may be used to convert a biphasic signal to a monophasic one (e.g., to prevent a positive signal from being sent from the pacing device to an external electrode (e.g., as signal 80), but not necessarily to prevent a negative signal from being sent from the pacing device to an internal electrode (e.g., as signal 40))). In other embodiments, as also shown in FIG. 1B, rather than utilizing such second safety circuitry 22*b* within a safety device 20, similar second safety circuitry (e.g., diode 72*b*') may be provided by coupler 71 (e.g., within connector 76*b*), which may obviate the need for at least circuitry 22*b* if not also safety device 20, such that connector 76*a* may be coupled directly to connector 36*b*.

Therefore, any suitable safety circuitry may be provided by a safety device assembly 20 and/or by particular safety circuitry(ies) in particular couplers of system 10' in order to protect patient 1 using delivery apparatus 100 as a unipolar arrangement regardless of whether pacing device 30' is a monophasic or biphasic signal generator. Therefore, system 10' enables safe integration of a unipolar esophageal catheter with a standard bedside monitor (e.g., a standard transcutaneous pulse generator) by protecting each internal electrode from too high energy and/or avoiding application of a biphasic current to an external electrode for passage to an internal electrode. Without such safety considerations, such a catheter system might only be safely used with a transvenous pulse generator that is only monophasic. Therefore, transesophageal system 10 and/or system 10' may enable more effective and lower current cardioversion and defibrillation capability as compared to non-unipolar designs (e.g., a conventional pacing device 30' may be successfully integrated for pacing a patient at low currents (e.g., 35 mA (e.g., lower than transcutaneous pacing)), where fuse 22*a*' and/or fuse 52*a*' may be used to prevent higher current energy. This may allow for better tolerated cardiac-pacing and safety for the patients. The transesophageal system may enable safer defibrillation capability for personnel working on the patient by having a lower risk of transmission of defibrillation current compared to transcutaneous systems. Transesophageal system 10 and/or system 10' may be configured to provide ECG monitoring while simultaneously pacing the heart. Therefore, transesophageal system 10 and/or system 10' may be configured to integrate the functionality of a unipolar esophageal cardiac pacer/defibrillator and a gastric decompression tube, while including purpose built features to augment its integrated functionality, including, but not limited to, flexible electrode arrays, an array of internal electrodes that accounts for movement of the patient's neck as the array is likely to stay in the patient for long periods of time, features that allow for smoother passage of the electrodes through the pharyngeal mucosa (e.g., beveled edges), and/or features that allow the system to better/safely integrate with bedside pulse generators that are used primarily for transcutaneous pacing. Unlike transcutaneous pacing that may be a temporary method of pacing the heart (e.g., using two or more external electrodes to deliver electrical impulses to the heart through the skin), transesophageal pacing may be a less temporary method by using at least one internal electrode positioned with a patient's esophagus or stomach to deliver electrical impulses to the heart. The unipolar transesophageal system is purpose designed with novel features to function as a nasogastric/orogastric tube and unipolar esophageal pacing/defibrillation system.

One, some, or all of the processes described with respect to FIGS. 1-22C may each be implemented by software, but may also be implemented in hardware, firmware, or any combination of software, hardware, and firmware. Instructions for performing these processes may also be embodied as machine- or computer-readable code recorded on a machine- or computer-readable medium. In some embodiments, the computer-readable medium may be a non-transitory computer-readable medium. Examples of such a non-transitory computer-readable medium include but are not limited to a read-only memory, a random-access memory, a flash memory, a CD-ROM, a DVD, a magnetic tape, a removable memory card, and a data storage device (e.g., memory 33 of a device 30). In other embodiments, the computer-readable medium may be a transitory computer-readable medium. In such embodiments, the transitory computer-readable medium can be distributed over network-coupled computer systems so that the computer-readable code is stored and executed in a distributed fashion. For example, such a transitory computer-readable medium may be communicated from a central network controller device to a router device or from a data device to any network device. Such a transitory computer-readable medium may embody computer-readable code, instructions, data structures, program modules, or other data in a modulated data signal, such as a carrier wave or other transport mechanism, and may include any information delivery media. A modulated data signal may be a signal that has one or more of its characteristics set or changed in such a manner as to encode information in the signal.

Any, each, or at least one module or component or subsystem of the disclosure may be provided as a software construct, firmware construct, one or more hardware components, or a combination thereof. For example, any, each, or at least one module or component or subsystem of system 1 may be described in the general context of computer-executable instructions, such as program modules, that may be executed by one or more computers or other devices. Generally, a program module may include one or more routines, programs, objects, components, and/or data structures that may perform one or more particular tasks or that may implement one or more particular abstract data types. The number, configuration, functionality, and interconnection of the modules and components and subsystems of system 1 are only illustrative, and that the number, configuration, functionality, and interconnection of existing modules, components, and/or subsystems may be modified or omitted, additional modules, components, and/or subsystems may be added, and the interconnection of certain modules, components, and/or subsystems may be altered.

As may be used in this specification and any claims of this application, the terms "base station," "receiver," "computer," "server," "processor," and "memory" may all refer to electronic or other technological devices. These terms exclude people or groups of people. For the purposes of the specification, the terms "display" or "displaying" means displaying on an electronic device.

As may be used herein, the terms "computer," "personal computer," "device," "computing device," "router device," and "controller device" may refer to any programmable computer system that is known or that will be developed in the future. In certain embodiments, a computer will be coupled to a network, such as described herein. A computer system may be configured with processor-executable software instructions to perform the processes described herein. Such computing devices may be mobile devices, such as a mobile telephone, data assistant, tablet computer, or other such mobile device. Alternatively, such computing devices may not be mobile (e.g., in at least certain use cases), such as in the case of server computers, desktop computing systems, or systems integrated with non-mobile components.

As may be used herein, the terms "component," "module," and "system," are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a server and the server may be a component. One or more components may reside within a process and/or thread of execution and a component may be localized on one computer and/or distributed between two or more computers.

The predicate words "configured to," "operable to," "operative to," and "programmed to" do not imply any particular tangible or intangible modification of a subject, but, rather, are intended to be used interchangeably. In one or more implementations, a processor configured to monitor and control an operation or a component may also mean the processor being programmed to monitor and control the operation or the processor being operable to monitor and control the operation or the processor being operative to monitor and control the operation. Likewise, a processor configured to execute code can be construed as a processor programmed to execute code or operable to execute code or operative to execute code.

As used herein, the term "based on" may be used to describe one or more factors that may affect a determination. However, this term does not exclude the possibility that additional factors may affect the determination. For example, a determination may be solely based on specified factors or based on the specified factors as well as other, unspecified factors. The phrase "determine A based on B" specifies that B is a factor that is used to determine A or that affects the determination of A. However, this phrase does not exclude that the determination of A may also be based on some other factor, such as C. This phrase is also intended to cover an embodiment in which A may be determined based solely on B. As used herein, the phrase "based on" may be synonymous with the phrase "based at least in part on."

As used herein, the phrase "in response to" may be used to describe one or more factors that trigger an effect. This phrase does not exclude the possibility that additional factors may affect or otherwise trigger the effect. For example, an effect may be solely in response to those factors, or may be in response to the specified factors as well as other, unspecified factors. The phrase "perform A in response to B" specifies that B is a factor that triggers the performance of A. However, this phrase does not foreclose that performing A may also be in response to some other factor, such as C. This phrase is also intended to cover an embodiment in which A is performed solely in response to B.

Phrases such as an aspect, the aspect, another aspect, some aspects, one or more aspects, an implementation, the implementation, another implementation, some implementations, one or more implementations, an embodiment, the embodiment, another embodiment, some implementations, one or more implementations, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

The word "exemplary" is used herein to mean "serving as an example, instance, or illustration". Any embodiment described herein as "exemplary" or as an "example" is not necessarily to be construed as preferred or advantageous over other implementations. Furthermore, to the extent that the term "include," "have," or the like is used in the description or the claims, such term is intended to be inclusive in a manner similar to the term "comprise" as "comprise" is interpreted when employed as a transitional word in a claim.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. The term "and/or" as used herein refers to and encompasses any and all possible combinations of one or more of the associated listed items. As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" may each refer to only A, only B, or only C; any combination of A, B, and C; and/or at least one of each of A, B, and C. The terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof. When used in the claims, the term "or" is used as an inclusive or and not as an exclusive or. For example, the phrase "at least one of x, y, or z" means any one of x, y, and z, as well as any combination thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for".

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but are to be accorded the full scope consistent with the language claims, wherein reference to an element in the singular is not intended to mean "one and only one" unless specifically so stated, but rather "one or more". Unless specifically stated otherwise, the term "some" refers to one or more. Pronouns in the masculine (e.g., his) include the feminine and neuter/neutral gender (e.g., her and its and they) and vice versa. Headings and subheadings, if any, are used for convenience only and do not limit the subject disclosure.

While there have been described esophageal cardiac stimulation and gastric decompression assemblies and methods for using and making the same, many changes may be made therein without departing from the spirit and scope of the subject matter described herein in any way. Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements. It is also to be understood that various directional and orientational terms, such as "left" and "right," "up" and "down," "front" and "back" and "rear," "top" and "bottom" and "side," "above" and "below," "length" and "width" and "thickness" and "diameter" and "cross-section" and "longitudinal," "X-" and "Y-" and "Z-," and/or the like, may be used herein only for convenience, and that no fixed or absolute directional or orientational limitations are intended by the use of these terms. For example, the components of an apparatus can have any desired orientation. If reoriented, different directional or orientational terms may need to be used in their description, but that will not alter their fundamental nature as within the scope and spirit of the disclosure.

Therefore, those skilled in the art will appreciate that the concepts of the disclosure can be practiced by other than the described embodiments, which are presented for purposes of illustration rather than of limitation.

What is claimed is:

1. An esophageal intubation assembly comprising:
    a catheter comprising:
        a body structure extending along a body structure length from a proximal body end to a distal body end;
        a passageway extending within the body structure and along at least a portion of the body structure length from a proximal passageway end to a distal passageway end;
        a proximal passageway opening passing through the body structure at a proximal passageway opening location for fluidly coupling the passageway with an ambient environment of the body structure at the proximal passageway opening location; and
        a distal passageway opening passing through the body structure at a distal passageway opening location for fluidly coupling the passageway with an ambient environment of the body structure at the distal passageway opening location, wherein the distal passageway opening location is distal of the proximal passageway opening location along the body structure length; and
    cardiac stimulation circuitry comprising:
        a first electrode coupled to the body structure at a first electrode location;
        a second electrode coupled to the body structure at a second electrode location; and
        a communicative coupler assembly that electrically couples the first electrode and the second electrode in parallel, wherein:
            the second electrode comprises an electrode opening passing through an exterior surface portion of the second electrode; and
            at least a portion of the electrode opening aligns with at least a portion of the distal passageway opening for passing fluid therebetween.

2. The esophageal intubation assembly of claim 1, wherein:
    the first electrode location is distal of the proximal passageway opening location along the body structure length;
    the second electrode location is distal of the proximal passageway opening location along the body structure length; and
    the first electrode location is distal of the distal passageway opening location along the body structure length.

3. The esophageal intubation assembly of claim 1, wherein:
    the first electrode location is distal of the proximal passageway opening location along the body structure length;
    the second electrode location is distal of the proximal passageway opening location along the body structure length; and
    the first electrode location is proximal of the distal passageway opening location along the body structure length.

4. The esophageal intubation assembly of claim 1, wherein:
    a portion of the body structure extending along an inducible portion of the body structure length is inducible into a curve; and
    the portion of the body structure comprises at least one of the following:
        the first electrode location; or
        the second electrode location.

5. The esophageal intubation assembly of claim 1, wherein the first electrode comprises a coil wire extending about and along the body structure.

6. The esophageal intubation assembly of claim 1, wherein the first electrode comprises a plurality of wires braided about and along the body structure.

7. The esophageal intubation assembly of claim 1, wherein the first electrode is coupled to an exterior surface of the body structure.

8. The esophageal intubation assembly of claim 1, wherein the first electrode is positioned at least partially within a wall of the body structure.

9. The esophageal intubation assembly of claim 1, wherein the first electrode location and the second electrode location are spaced along the body structure length by a distance that is at least 7 millimeters.

10. The esophageal intubation assembly of claim 1, wherein the first electrode location and the second electrode location are spaced apart along the body structure length by a distance that is between 7.0 millimeters and 13.0 millimeters.

11. The esophageal intubation assembly of claim 10, wherein:
    the first electrode comprises a first metal band that extends about a first periphery of the body structure; and
    the second electrode comprises a second metal band that extends about a second periphery of the body structure.

12. The esophageal intubation assembly of claim 1, wherein the communicative coupler assembly comprises a coupler connector that is electrically coupled to the first electrode and the second electrode in parallel.

13. The esophageal intubation assembly of claim 12, wherein the coupler connector is configured to be removably coupled to a device connector of a pacing device.

14. The esophageal intubation assembly of claim 1, wherein a portion of the communicative coupler assembly extends within the body structure and along at least another portion of the body structure length.

15. An esophageal intubation assembly for use with a pacing device that comprises a first pacing device connector and a second pacing device connector, the assembly comprising:
   a catheter comprising:
      a body structure extending along a body structure length from a proximal body end to a distal body end;
      a passageway extending within the body structure and along at least a portion of the body structure length from a proximal passageway end to a distal passageway end;
      a proximal passageway opening passing through the body structure at a proximal passageway opening location for fluidly coupling the passageway with an ambient environment of the body structure at the proximal passageway opening location; and
      a distal passageway opening passing through the body structure at a distal passageway opening location for fluidly coupling the passageway with an ambient environment of the body structure at the distal passageway opening location, wherein the distal passageway opening location is distal of the proximal passageway opening location along the body structure length;
   a safety device comprising:
      a first safety device connector configured to be removably coupled to the first pacing device connector;
      a second safety device connector configured to be removably coupled to the second pacing device connector;
      a third safety device connector;
      a fourth safety device connector;
      first safety circuitry electrically coupled between the first safety device connector and the third safety device connector; and
      second safety circuitry electrically coupled between the second safety device connector and the fourth safety device connector; and
   cardiac stimulation circuitry comprising:
      a first electrode coupled to the body structure;
      a first communicative coupler assembly electrically coupling the first electrode to a first coupler connector, wherein the first coupler connector is configured to be coupled to the third safety device connector;
      a second electrode; and
      a second communicative coupler assembly electrically coupling the second electrode to a second coupler connector, wherein:
         the second coupler connector is configured to be coupled to the fourth safety device connector;
         the first safety circuitry comprises a fuse configured to prevent a signal with an energy above a particular energy threshold from passing from the first safety device connector to the third safety device connector; and
         the second safety circuitry comprises a diode configured to prevent current from flowing from the second safety device connector to the fourth safety device connector.

16. The esophageal intubation assembly of claim 15, wherein the pacing device is a biphasic pacing device.

17. The esophageal intubation assembly of claim 16, wherein the esophageal intubation assembly is configured with the pacing device as a unipolar esophageal pacing system.

* * * * *